United States Patent
Goss et al.

(10) Patent No.: US 12,214,013 B2
(45) Date of Patent: Feb. 4, 2025

(54) METHODS OF TREATMENT OF ARTHRITIS AND/OR PSORIASIS WITH PHARMACEUTICAL FORMULATIONS OF ETANERCEPT

(71) Applicant: AMGEN INC., Thousand Oaks, CA (US)

(72) Inventors: Monica Goss, Newbury Park, CA (US); Nicole Ball, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 36 days.

(21) Appl. No.: 17/933,055

(22) Filed: Sep. 16, 2022

(65) Prior Publication Data
US 2023/0080571 A1 Mar. 16, 2023

Related U.S. Application Data

(60) Division of application No. 16/144,120, filed on Sep. 27, 2018, now Pat. No. 11,491,223, which is a division of application No. 15/958,261, filed on Apr. 20, 2018, now Pat. No. 10,307,483, which is a continuation of application No. 15/788,762, filed on Oct. 19, 2017, now abandoned.

(60) Provisional application No. 62/411,458, filed on Oct. 21, 2016.

(51) Int. Cl.
| | | |
|---|---|---|
| *A61P 19/02* | (2006.01) | |
| *A61K 9/00* | (2006.01) | |
| *A61K 9/08* | (2006.01) | |
| *A61K 38/17* | (2006.01) | |
| *A61K 39/395* | (2006.01) | |
| *A61K 47/02* | (2006.01) | |
| *A61K 47/18* | (2017.01) | |
| *A61K 47/26* | (2006.01) | |
| *A61K 47/68* | (2017.01) | |
| *A61P 17/06* | (2006.01) | |
| *A61P 29/00* | (2006.01) | |
| *C07K 14/715* | (2006.01) | |
| *C07K 19/00* | (2006.01) | |

(52) U.S. Cl.
CPC ........ *A61K 38/1793* (2013.01); *A61K 9/0019* (2013.01); *A61K 9/08* (2013.01); *A61K 39/39591* (2013.01); *A61K 47/02* (2013.01); *A61K 47/183* (2013.01); *A61K 47/26* (2013.01); *A61K 47/68* (2017.08); *A61P 17/06* (2018.01); *A61P 19/02* (2018.01); *A61P 29/00* (2018.01); *C07K 14/7151* (2013.01); *C07K 19/00* (2013.01); *C07K 2319/30* (2013.01); *C07K 2319/32* (2013.01)

(58) Field of Classification Search
CPC .............. A61K 38/1793; A61K 47/183; C07K 14/7151; C07K 2319/30; A61P 17/06; A61P 19/02; A61P 29/00
See application file for complete search history.

(56) References Cited

U.S. PATENT DOCUMENTS

| | | |
|---|---|---|
| 4,322,403 A | 3/1982 | Bunnig |
| 4,396,608 A | 8/1983 | Tenold |
| 4,597,966 A | 7/1986 | Zolton et al. |
| 4,681,713 A | 7/1987 | Miyagi et al. |
| 4,849,508 A | 7/1989 | Magnin et al. |
| 4,876,088 A | 10/1989 | Hirao et al. |
| 4,877,866 A | 10/1989 | Rudnick et al. |
| 5,110,910 A | 5/1992 | Tsay |
| 5,177,194 A | 1/1993 | Sarno et al. |
| 5,256,571 A | 10/1993 | Hurley et al. |
| 5,298,410 A | 3/1994 | Phillips et al. |
| 5,484,892 A | 1/1996 | Tedder |
| 5,580,856 A | 12/1996 | Pestrelski et al. |
| 5,608,038 A | 3/1997 | Eibl et al. |
| 5,691,312 A | 11/1997 | Paques |
| 5,702,699 A | 12/1997 | Hanisch et al. |
| 5,717,072 A | 2/1998 | Mosley et al. |
| 5,789,554 A | 8/1998 | Leung et al. |
| 5,945,098 A | 8/1999 | Sarno et al. |
| 6,004,555 A | 12/1999 | Thorpe et al. |
| RE36,755 E | 6/2000 | Smith et al. |
| 6,090,382 A | 7/2000 | Salfeld et al. |
| 6,093,324 A | 7/2000 | Bertolini |
| 6,171,586 B1 | 1/2001 | Lam et al. |
| 6,252,055 B1 | 6/2001 | Relton |
| 6,281,336 B1 | 8/2001 | Laursen et al. |
| 6,436,897 B2 | 8/2002 | Danko et al. |
| 6,610,206 B1 | 8/2003 | Callan et al. |
| 6,673,347 B1 | 1/2004 | Offord et al. |
| 6,696,056 B1 | 2/2004 | Cheung et al. |
| 6,875,848 B2 | 4/2005 | Ristol Debart et al. |

(Continued)

FOREIGN PATENT DOCUMENTS

| | | |
|---|---|---|
| CA | 2 474 943 | 8/2003 |
| EP | 0 025 275 | 3/1981 |

(Continued)

OTHER PUBLICATIONS

Corrected Notice of Allowability for U.S. Appl. No. 13/797,622 in 6 pages, dated Feb. 8, 2023.

(Continued)

*Primary Examiner* — Zachary C Howard
(74) *Attorney, Agent, or Firm* — KNOBBE, MARTENS, OLSON & BEAR, LLP

(57) ABSTRACT

The invention relates to the formulation of pharmaceutical compositions of etanercept. The invention also relates to methods of removing buffer and of formulating pharmaceutical compositions of etanercept.

48 Claims, 9 Drawing Sheets
Specification includes a Sequence Listing.

(56) References Cited

U.S. PATENT DOCUMENTS

| | | |
|---|---|---|
| 7,122,641 B2 | 10/2006 | Vendantham et al. |
| 7,157,557 B2 | 1/2007 | Sassenfeld et al. |
| 7,294,481 B1 | 11/2007 | Fung |
| 7,300,773 B2 | 11/2007 | Drapeau et al. |
| 7,364,736 B2 | 4/2008 | Boyle et al. |
| 7,452,695 B2 | 11/2008 | Van Ness et al. |
| 7,648,702 B2 | 1/2010 | Gombotz et al. |
| 7,666,413 B2 | 2/2010 | Liu et al. |
| 7,718,776 B2 | 5/2010 | Boyle et al. |
| 7,879,331 B2 | 2/2011 | Zurlo et al. |
| 7,915,225 B2 | 3/2011 | Finck |
| 8,034,906 B2 | 10/2011 | Borhani et al. |
| 8,052,645 B2 | 11/2011 | Slate et al. |
| 8,063,182 B1 | 11/2011 | Brockhaus et al. |
| 8,119,604 B2 | 2/2012 | Gombotz et al. |
| 8,119,605 B2 | 2/2012 | Finck |
| 8,163,522 B1 | 4/2012 | Brockhaus et al. |
| 8,177,749 B2 | 5/2012 | Slate et al. |
| 8,410,060 B2 | 4/2013 | Kazama et al. |
| 8,420,081 B2 | 4/2013 | Fraunhofer et al. |
| 8,597,709 B2 | 12/2013 | Gahler et al. |
| 8,722,631 B2 | 5/2014 | Finck |
| 8,821,865 B2 | 9/2014 | Neu et al. |
| 8,828,947 B2 | 9/2014 | Gombotz et al. |
| 8,871,201 B2 | 10/2014 | Li et al. |
| 8,883,146 B2 | 11/2014 | Fraunhofer et al. |
| 8,920,374 B2 | 12/2014 | Bokelman et al. |
| 8,945,564 B2 | 2/2015 | Lu et al. |
| 9,085,619 B2 | 7/2015 | Fraunhofer et al. |
| 9,114,166 B2 | 8/2015 | Krause et al. |
| 9,182,410 B1 | 11/2015 | Rupprechter et al. |
| 9,302,002 B2 | 4/2016 | Manning et al. |
| 9,452,138 B2 | 9/2016 | Trollsas et al. |
| 9,453,067 B2 | 9/2016 | Deutel et al. |
| 9,518,111 B2 | 12/2016 | Gombotz et al. |
| 9,616,173 B2 | 4/2017 | Slate et al. |
| 9,649,383 B2 | 5/2017 | Kashi et al. |
| 9,700,595 B2 | 7/2017 | Lee et al. |
| 9,763,976 B1 | 9/2017 | Obagi et al. |
| 10,307,483 B2 | 6/2019 | Goss et al. |
| 11,491,223 B2 | 11/2022 | Goss et al. |
| 11,607,451 B2 | 3/2023 | Gokarn et al. |
| 2001/0021380 A1 | 9/2001 | Phuenneke |
| 2003/0138417 A1 | 7/2003 | Kaisheva et al. |
| 2003/0138421 A1 | 7/2003 | Van de Winkel et al. |
| 2003/0143603 A1 | 7/2003 | Giles-Komar et al. |
| 2003/0180253 A1 | 9/2003 | Chen et al. |
| 2003/0180287 A1 | 9/2003 | Gombotz et al. |
| 2003/0190316 A1 | 10/2003 | Kakuta et al. |
| 2003/0202975 A1 | 10/2003 | Tedder |
| 2003/0206898 A1 | 11/2003 | Fischkoff et al. |
| 2003/0235686 A1 | 12/2003 | Caspari et al. |
| 2004/0033228 A1 | 2/2004 | Krause et al. |
| 2004/0038878 A1 | 2/2004 | Tanikawa et al. |
| 2004/0071702 A1 | 4/2004 | Van de Winkel et al. |
| 2004/0126373 A1 | 7/2004 | Banerjee et al. |
| 2004/0136990 A1 | 7/2004 | Banerjee et al. |
| 2004/0181033 A1 | 9/2004 | Han et al. |
| 2004/0197324 A1 | 10/2004 | Liu et al. |
| 2004/0202655 A1 | 10/2004 | Morton et al. |
| 2004/0228913 A1 | 11/2004 | Kumar et al. |
| 2005/0214278 A1 | 9/2005 | Kabuta et al. |
| 2006/0127395 A1 | 7/2006 | Arvinte et al. |
| 2006/0149042 A1 | 7/2006 | Konstantinov et al. |
| 2006/0153846 A1 | 7/2006 | Krause et al. |
| 2006/0182740 A1 | 8/2006 | Yang et al. |
| 2007/0065567 A1 | 3/2007 | Segall et al. |
| 2007/0071675 A1 | 3/2007 | Wu et al. |
| 2007/0172475 A1 | 7/2007 | Matheus et al. |
| 2007/0202051 A1 | 8/2007 | Schuschnig |
| 2007/0269463 A1 | 11/2007 | Donovan |
| 2008/0003220 A1 | 1/2008 | Gokarn |
| 2008/0071097 A1 | 3/2008 | Taugerbeck et al. |
| 2008/0161242 A1 | 7/2008 | Randolph et al. |
| 2008/0213282 A1 | 9/2008 | Jacob et al. |
| 2008/0286280 A1 | 11/2008 | Kallmeyer et al. |
| 2008/0311078 A1 | 12/2008 | Gokarn et al. |
| 2010/0137213 A1 | 6/2010 | Fernandez et al. |
| 2011/0060290 A1 | 3/2011 | Bonk et al. |
| 2011/0070227 A1 | 3/2011 | Novotney-Barry et al. |
| 2011/0171217 A1 | 7/2011 | Badkar |
| 2011/0224616 A1 | 9/2011 | Slate et al. |
| 2012/0028877 A1 | 2/2012 | Gokarn et al. |
| 2012/0265142 A1 | 4/2012 | Slate et al. |
| 2013/0023825 A1 | 1/2013 | Edwards et al. |
| 2013/0273066 A1 | 10/2013 | Gokarn et al. |
| 2013/0273067 A1 | 10/2013 | Gokarn et al. |
| 2014/0072560 A1 | 3/2014 | Arakawa et al. |
| 2014/0199303 A1 | 7/2014 | Choi et al. |
| 2014/0255400 A1 | 9/2014 | Maloney et al. |
| 2015/0045729 A1 | 2/2015 | Denzer et al. |
| 2015/0118249 A1 | 4/2015 | Leach et al. |
| 2015/0283241 A1 | 10/2015 | Deepak et al. |
| 2015/0313996 A1 | 11/2015 | Park et al. |
| 2016/0022914 A1 | 1/2016 | Mounce et al. |
| 2016/0106844 A1 | 4/2016 | Bañado et al. |
| 2016/0120751 A1 | 5/2016 | Mounce et al. |
| 2016/0319011 A1 | 11/2016 | Gokarn et al. |
| 2016/0339102 A1 | 11/2016 | Gokarn et al. |
| 2016/0362484 A1 | 12/2016 | Gokarn et al. |
| 2016/0362485 A1 | 12/2016 | Gokarn et al. |
| 2016/0362486 A1 | 12/2016 | Gokarn et al. |
| 2016/0367665 A1 | 12/2016 | Gokarn et al. |
| 2016/0367666 A1 | 12/2016 | Gokarn et al. |
| 2017/0051039 A1 | 2/2017 | Gombotz et al. |
| 2017/0143828 A1 | 5/2017 | Fraunhofer et al. |
| 2017/0348225 A1 | 12/2017 | Freitag et al. |
| 2017/0368170 A1 | 12/2017 | Gokarn et al. |
| 2018/0110856 A1 | 4/2018 | Goss et al. |
| 2019/0144523 A1 | 5/2019 | Gombotz et al. |
| 2019/0292237 A1 | 9/2019 | Gombotz et al. |
| 2021/0007991 A1 | 1/2021 | Manning et al. |

FOREIGN PATENT DOCUMENTS

| | | |
|---|---|---|
| EP | 0 025 321 | 3/1981 |
| EP | 0 025 719 | 3/1981 |
| EP | 0 490 549 | 6/1992 |
| EP | 0 614 666 | 9/1994 |
| EP | 0 619 324 | 10/1994 |
| EP | 0 665 019 | 8/1995 |
| EP | 0 893 450 | 1/1999 |
| EP | 1 304 376 | 4/2003 |
| EP | 1 314 437 | 5/2003 |
| EP | 1 475 101 | 11/2004 |
| EP | 0 909 564 | 6/2006 |
| EP | 2 926 834 | 10/2015 |
| JP | S61-218528 | 9/1986 |
| JP | S63-145237 | 6/1988 |
| JP | S63-192724 | 8/1988 |
| JP | H06-256222 | 9/1994 |
| JP | 2002-539770 | 11/2002 |
| JP | 2004-532262 | 10/2004 |
| JP | 2005-027671 | 2/2005 |
| JP | 2005-506963 | 3/2005 |
| JP | 2015-519382 A | 7/2015 |
| KR | 10-2016-0068946 | 6/2016 |
| WO | WO 92/02616 | 2/1992 |
| WO | WO 97/29131 | 8/1997 |
| WO | WO 97/40850 | 11/1997 |
| WO | WO 98/01555 | 1/1998 |
| WO | WO 98/03550 | 1/1998 |
| WO | WO 98/22136 | 5/1998 |
| WO | WO 00/29004 | 5/2000 |
| WO | WO 00/46240 | 8/2000 |
| WO | WO 00/061177 | 10/2000 |
| WO | WO 00/062790 | 10/2000 |
| WO | WO 01/24814 | 4/2001 |
| WO | WO 01/43773 | 6/2001 |
| WO | WO 01/44472 | 6/2001 |
| WO | WO 01/58473 | 8/2001 |
| WO | WO 01/60397 | 8/2001 |
| WO | WO 02/08417 | 1/2002 |
| WO | WO 02/13860 | 2/2002 |

(56) References Cited

FOREIGN PATENT DOCUMENTS

| WO | WO 02/30463 | 4/2002 |
|---|---|---|
| WO | WO 02/47721 | 6/2002 |
| WO | WO 02/051979 | 7/2002 |
| WO | WO 02/053596 | 7/2002 |
| WO | WO 02/096457 | 12/2002 |
| WO | WO 03/001563 | 1/2003 |
| WO | WO 03/002713 | 1/2003 |
| WO | WO 03/017935 | 3/2003 |
| WO | WO 03/024388 | 3/2003 |
| WO | WO 03/068260 | 8/2003 |
| WO | WO 03/093320 | 11/2003 |
| WO | WO 03/102132 | 12/2003 |
| WO | WO 2004/001007 | 12/2003 |
| WO | WO 2004/016286 | 2/2004 |
| WO | WO 2004/083248 | 9/2004 |
| WO | WO 2004/110490 | 12/2004 |
| WO | WO 2005/035572 | 4/2005 |
| WO | WO 2005/047331 | 5/2005 |
| WO | WO 2005/049078 | 6/2005 |
| WO | WO 2005/095454 | 10/2005 |
| WO | WO 2005/112893 | 12/2005 |
| WO | WO 2006/003999 | 1/2006 |
| WO | WO 2006/024497 | 3/2006 |
| WO | WO 2006/031560 | 3/2006 |
| WO | WO 2006/064373 | 6/2006 |
| WO | WO 2006/138181 | 12/2006 |
| WO | WO 2007/124082 | 11/2007 |
| WO | WO 2008/079290 | 7/2008 |
| WO | WO 2008/132616 | 11/2008 |
| WO | WO 2009/073569 | 6/2009 |
| WO | WO 2010/102241 | 9/2010 |
| WO | WO 2013/186230 A1 | 12/2013 |
| WO | WO 2014/008393 | 1/2014 |
| WO | WO 2014/064637 | 5/2014 |
| WO | WO 2014/078627 | 5/2014 |
| WO | WO 2014/177548 | 11/2014 |
| WO | WO 2016/033496 | 3/2016 |
| WO | WO 2016/033507 | 3/2016 |
| WO | WO 2016/149139 | 9/2016 |
| WO | WO 2018/075818 | 4/2018 |

OTHER PUBLICATIONS

Corrected Notice of Allowability for U.S. Appl. No. 13/797,622 in 8 pages, dated Jan. 11, 2023.
Hearing Notice for Indian Application No. IN 201917015635 with English translation in 3 pages, dated Oct. 20, 2023.
Office Action for Chinese Application No. CN 202210152416.X with English translation in 27 pages, dated Mar. 1, 2023.
Office Action for Japanese Application No. 2021-080160 with English translation in 7 pages, dated Jun. 20, 2023.
Office Action for Japanese Application No. 2021-080160 with English translation in 6 pages, dated Dec. 20, 2022.
Office Action for Japanese Application No. JP 2022-156398 with English translation in 14 pages, dated Sep. 5, 2023.
Office Action for Mexican Application No. MX/a/2019/004580 with English translation in 9 pages, dated Sep. 26, 2023.
Office Action for Singaporean Application No. 11201903521X in 4 pages, dated Jun. 8, 2023.
Summons to Attend Oral Proceedings pursuant to Rule 115(1) EPC and Communication from the Examining Division for European Application No. EP 19217355.7 in 9 pages, dated May 4, 2023.
Claims filed Oct. 25, 2018 in U.S. Appl. No. 16/144,120.
Corrected Notice of Allowability for U.S. Appl. No. 16/144,120 in 3 pages, dated Aug. 8, 2022.
Corrected Notice of Allowability for U.S. Appl. No. 16/144,120 in 3 pages, dated Jul. 27, 2022.
Corrected Notice of Allowability for U.S. Appl. No. 16/144,120 in 3 pages, dated Oct. 12, 2022.
Corrected Notice of Allowability for U.S. Appl. No. 16/144,120 in 3 pages, dated Sep. 14, 2022.

File History of U.S. Appl. No. 16/144,120.
Notice of Allowability for U.S. Appl. No. 16/144,120 in 3 pages, dated Jul. 20, 2023.
Notice of Allowance dated Feb. 25, 2021 in U.S. Appl. No. 16/144,120 in 10 pages.
Notice of Allowance dated Jun. 15, 2021 in U.S. Appl. No. 16/144,120 in 14 pages.
Notice of Allowance dated Nov. 1, 2021 in U.S. Appl. No. 16/144,120 in 10 pages.
Notice of Allowance dated Nov. 5, 2020 in U.S. Appl. No. 16/144,120 in 10 pages.
Notice of Allowance dated Sep. 17, 2020 in U.S. Appl. No. 16/144,120.
Notice of Allowance for U.S. Appl. No. 13/797,622 in 11 pages, dated Oct. 21, 2022.
Notice of Allowance for U.S. Appl. No. 16/144,120 in 11 pages, dated Mar. 4, 2022.
Notice of Allowance for U.S. Appl. No. 16/144,120 in 9 pages, dated Jun. 23, 2022.
Office Action for Chilean Application No. CL 201901053 with English translation in 3 pages, dated Sep. 1, 2022.
Restriction Requirement dated Apr. 20, 2020 in U.S. Appl. No. 16/144,120.
Extended Hearing Notice for Indian Application No. IN 201917015635 with English translation in 3 pages, dated Dec. 22, 2023.
Notice of Allowance for Mexican Application No. MX/a/2019/004580 with English translation in 6 pages, dated Feb. 27, 2024.
Office Action for European Application No. EP 17862991.1 in 5 pages, dated Mar. 5, 2024.
Office Action for Japanese Application No. JP 2022-156398 with English translation in 13 pages, dated Mar. 5, 2024.
U.S. Appl. No. 60/700,265, filed Jul. 18, 2005, Siu et al.
"Adalimumab" Drugs of the Future, 2001, 26: pp. 639-646.
"Development Pharmaceutics for Biotechnological and Biological Products (Annex to Note for Guidance on Development Pharmaceutics)," by Committee for Proprietary Medicinal Products, The European Agency for the Evaluation of Medicinal Products (Oct. 21, 1999).
"Gamimune® N, 5%,—Immune Globulin Intravenous (Human), 5% Solvent/Detergent Treated", Physcians' Desk Reference, 2002, Montvale, N.J., 56th ed., pp. 925-931, filed as Exhibit A33 in the Demand for Invalidation Trial against Japanese Patent No. 6293103.
"Injection Tips, " Humira.com, http://www.humira.com/hu/hustore/cgi-bin/ProdSubEV_Cat_205043_SubCat_210170_NavRoot_205042_NavID_301.htm [http://web.archive.org/web/20050317083331/http://www.humira.com/hu/hustore/cgi-bin/ProdSubEV_Cat_205043_SubCat_210170_NavRoot_205042_NavID_301.htm (Archived Mar. 17, 2005). It is noted that this item refers to a webpage and may have been available in some form at an earlier point in time.
"Note for Guidance on Development Pharmaceutics," by the Committee for Proprietary Medicinal Products (CPMP), The European Agency for the Evaluation of Medicinal Products (Jan. 28, 1998).
"Summary Review for Regulatory Action," by Sarah Yim, Division of Pulmonary, Allergy, and Rheumatology Products (U.S. Food & Drug Administration), Humira® (2015).
"Omalizumab" Biodrugs 2002. 15:380 (Exhibit A19).
AbbVie Biotechnology Ltd., "Patent Owner's Preliminary Response," in *Coherus Biosciences Inc.* v. *AbbVie Biotechnology Ltd.*, IPR2016-01018, Paper No. 9 (PTAB Aug. 9, 2016).
Acknowledgement Receipt for U.S. Appl. No. 17/810,225 in 100 pages, dated Jun. 30, 2022.
Acknowledgment of Settlement Agreement dated Jan. 20, 2018 Interference No. 106,057, involving U.S. Appl. No. 13/797,622 and U.S. Appl. No. 13/188,329 and U.S. Pat. No. 8,420,081.
Adalimumab Product Approval Information, http://www.fda.gov/Drugs/DevelopmentApprovalProcess/HowDrugsareDevelopedandApproved?ApprovalApplications/TherapeuticBiologicApplications/ucm080610.htm (accessed Jan. 23, 2017). It is noted that this item refers to a webpage and may have been available in some form at an earlier point in time.
Advisory Action dated Aug. 28, 2017 in U.S. Appl. No. 15/231,490.
Advisory Action Dated Feb. 28, 2007 in U.S. Appl. No. 10/376,576.
Advisory Action dated Sep. 5, 2017 in U.S. Appl. No. 15/232,733.

(56) References Cited

OTHER PUBLICATIONS

Affidavit of Christopher Butler Dated Feb. 21, 2017 in the Patent Trial and Appeal Board, United States Patent and Trademark Office, Petition Nos. PTAB-IPR2017-01008, PTAB-IPR2017-01009.
Affidavit of Marlene S. Bobka Dated Feb. 21, 2017 in the Patent Trial and Appeal Board, United States Patent and Trademark Office, Petition Nos. PTAB-IPR2017-01008, PTAB-IPR2017-01009.
Affidavit of Michael Deas attaching English translation of OCTAGAM® entry (75 008) in Rote Liste 2005 (Cantor Publishers 2005) as Exhibit A, and original German-language Rote Liste 2005 entry 75 008 as Exhibits B and C.
Ahrer et al., "Effects of ultra-/diafiltration conditions on present aggregates in human immunoglobulin G preparations", Journal of Membrane Science, 274: 108-115 (2006).
Akers et al., "Formulation Development of Protein Dosage Forms", Chapter 2, pp. 47-127, 2002.
Alberts, Molecular Biology of the Cell, Fourth Edition, New York, NY: Garland Publishing, Inc., pp. 1363-1384 (2002).
Alves. Antibody conjugation and formulation. Antibody Therapeutics, vol. 2, No. 1, 33-39. (2019).
Amendment Accompanying Request for Continued Examination Dated Feb. 19, 2016 in U.S. Appl. No. 13/797,622.
Amendment and Response to Final Office Action dated Jul. 22, 2015 in U.S. Appl. No. 13/797,622.
Amendment and Response to Final Office Action dated Nov. 17, 2017 in U.S. Appl. No. 15/231,490.
Amendment and Response to Non-Final Office Action dated Apr. 13, 2015 in U.S. Appl. No. 13/797,622.
Amendment and Response to Non-Final Office Action dated Jan. 8, 2016 in U.S. Appl. No. 13/797,622.
Amendment and Response to Non-Final Office Action dated Jun. 26, 2015 in U.S. Appl. No. 13/188,329.
Amendment and Response to Non-Final Office Action dated Mar. 10, 2015 in U.S. Appl. No. 13/188,329.
Amendment and Response to Office Action dated Feb. 7, 2020 in U.S. Appl. No. 13/797,622.
Amendment dated Aug. 24, 2015. U.S. Appl. No. 14/643,844.
Amersham Biosciences, "Ion Exchange Chromatography: Principles and Methods", 1-157 (1999).
Amgen's Supplemental Biologics License Application.
Andrew and Titus, "Fragmentation of Immunoglobulin G", Curr. Protoc. Cell Biol., Chapter 16:Unit 16.4, pp. 16.4.1-16.4.10 (2000).
Antoni et al., "Side effects of anti-TNF therapy: Current knowledge." Clin Exp Rheumatol 2002; 20 (Suppl. 28). S152-S157.
Applicant Initiated Interview Summary dated Feb. 8, 2016 in U.S. Appl. No. 13/188,329.
Applicant Initiated Interview Summary dated Jan. 22, 2016 in U.S. Appl. No. 13/797,622.
Applicant-Initiated Interview Summary dated Nov. 26, 2012 in U.S. Appl. No. 12/325,049.
Application Data Sheet Dated Nov. 28, 2008 in U.S. Appl. No. 12/325,049.
Arakawa et al., "Elution of Antibodies from a Protein—A Column by Aqueous Arginine Solutions", Protein Expr. Purif. 36:244-248 (2004).
Aulton, Michael E. Pharmaceutics: The Science of Dosage Form Design pp. 359-380 (1988).
AVASTIN Label (Feb. 2004).
Avonex® (interferon beta-1a) Label, 1-23 (2001).
Avonex® (interferon beta-1a), Physicians' Desk Reference, PDR 57, Thomson PDR, Montvale, NJ, pp. 1006-1010 (2003).
AvvVie Biotechnology Ltd., "Annex A—The Humira Story," in Opposition Proceeding for EP1406656 (filed on Dec. 22, 2014).
Bahrenburg et al. Buffer-free therapeutic antibody preparations provide a viable alternative to conventionally buffered solutions: From protein buffer capacity prediction to bioprocess applications, Biotechnol. J. 10, 610-622 (2015).
Barnett, et al., "Reduction of Pain and Local Complications When Buffered Lidocaine Solution is Used as a Local Anesthetic in Conjunction with Hyperthermia Treatments: Results of a Randomized Trial," Int'l J. Radiation Oncology Biol. Phys. 23(3), pp. 585-591. 1992.
Barrera, P. et al., "Effects of treatment with a fully human antitumour necrosis factor a monoclonal antibody on the local and systemic homeostasis of interleukin 1 and TNFa in patients with rheumatoid arthritis", Ann. Rheum. Dis., 60: 660-669 (2001).
Bekker et al., "A Single-Dose Placebo-Controlled Study of AMG 162, a Fully Human Monoclonal Antibody to RANKL, in Postmenopausal Women", J. Bone Miner. Res. 19:1059-1066 (2004).
Bellinghausen, I. et al, "Importance of the inducible costimulator molecule for the induction of allergic immune responses and its decreased expression on T helper cells after venom immunotherapy", Immunology, vol. 112(1), pp. 80-86.
Berg et al., "Exploring Proteins" in Biochemistry, 5th edition, pp. 77-116, New York, W H Freeman (copyright date 2002).
Berne, Robert M et al. excerpt, Chapter 20 "Blood Components" in Physiology 3rd Edition pp. 327-338 (1993).
Bexxar® (tositumomab and iodine I 131 tositumomab) Label, 1-49 (2003).
Bexxar® (tositumomab and iodine I 131 tositumomab), Physicians' Desk Reference, PDR 60, pp. 1360-1366 (2006).
Binabaji et al., "Theoretical Analysis of the Ultrafiltration Behavior of Highly Concentrated Protein Solutions", Journal of Membrane Science 494 :216-223 (2015).
Binabaji et al., "Ultrafiltration of Highly Concreated Antibody Solutions: Experiments and Modeling for the Effects of Module and Buffer Conditions", Biotech. Prog. 32:692-701 (2016).
Biochemical Dictionary, 3rd ed., 1998, filed as Exhibit A28 in the Demand for Invalidation Trial against Japanese Patent No. 6293103, in 4 pages (with partial English translation).
Biochemical Dictionary, 3rd ed., 1998, p. 456, filed as Exhibit A41 in the Demand for Invalidation Trial against Japanese Patent No. 5856555, in 3 pages.
Biologics License Application No. 125057/0, Submitted to the FDA on Mar. 28, 2002.
Bjorck et al., Purification and Some Properties of Streptoccal Protein G, a Novel IgG-Biding Reagent J. Immunol. 133:969-74 (1984).
Boes, "Role of Natural and Immune IgM Antibodies in Immune Responses," Mol. Immunol., 37:1141-1149 (2000).
Brazeau, et al., "Current Perspectives on Pain upon Injection of Drugs," J. Pharm. Sci 87(6), pp. 667-677. Jun. 1998.
Brown, Theodore L. et al., excerpt, Chapter 17 "Additional Aspects of Aqueous Equilibria" in Chemistry: The Central Science 8th Edition (2000).
Burton, D.R. et al., Aspects of the Molecular Structure of IgG Subclasses, 19 Monogr. Allergy 7-35 (1986).
Butler & Hamilton, "Quantitation of Specific Antibodies: Methods of Express, Standards, Solid-Phase Considerations, and Specific Applications," Ch. 9 Immunochemistry of Solid-Phase Immunoassay, CRC Press (John E. Butler ed., 1991).
Cada, ed., Adalimumab. Hospital Pharmacy 2003; 38: pp. 568-580.
Campath Label (Aug. 2006).
Campath® (alemtuzumab) Label, 1-14 (2004).
Campath® (alemtuzumab), Physicians' Desk Reference, PDR 57, Thomson PDR, Montvale, NJ, pp. 975-977 (2003).
Carnahan et al., "Epratuzumab, a Humanized Monoclonal Antibody Targeting CD22: Characterization of in Vitro Properties"; Clinical Cancer Research 9:3982s-3990s (2003).
Carpenter, et al., "Rational Design of Stable Lyophilized Protein Formulations: Some Practical Advice," Pharm. Res. 12(8), pp. 969-975. 1997.
Carpenter, J. F. and Manning, M. C., *Pharmaceutical Biotechnology—Rational Design of Stable Protein Formulations—Theory and Practice,* 2002, Kluwer Academic/Plenum Publishers, New York, First Edition, vol. 13 (book submitted in five parts).
Carter, "Improving the Efficacy of Antibody-Based Cancer Therapy", Nat. Rev. Cancer 1:118-129 (2001).
Castellano et al, "The Role of RANK-Ligand Inhibition of Cancer: The Story of Denosumab", The Oncologist 16:136-145 (2011).
Centor RM. Serum Total Carbon Dioxide. In: Walker HK, Hall WD, Hurst JW, editors. Clinical Methods: The History, Physical, and

(56) References Cited

OTHER PUBLICATIONS

Laboratory Examinations. 3rd edition. Boston: Butterworths; 1990. Chapter 196. Available from: https://www.ncbi.nlm.nih.gov/books/NBK308/ (retrieved Oct. 5, 2020).
Chang, B. S. and Hershenson, S., "Practical Approaches to Protein Formulation Development", in Rationale Design of stable Protein formulations—theory and Practice, (J. F. Carpenter and M. C. Manning, eds., Kluwer Academic/Plenum Publishers, New York, pp. 1-25 (2002).
Chang, B. S., "Ten Major Factors in Successful Protein Formulation Development", Integrity Bio, 3 pgs., (2012).
Chen et al., "Influence of histidine on the stability and physical properties of a fully human antibody in aqueous and solid forms," Pharmaceutical Research, Kluwer Academica Publishers, New York, US, vol. 20, No. 12 (Dec. 1, 2003), pp. 1952-1960.
Chen, et al., "Aggregation Pathway of Recombinant Human Keratinocyte Growth Factor and Its Stabilization," Pharm. Res. 11(11), pp. 1581-1587. 1994.
Chi, E. et al., "Physical Stability of Proteins in Aqueous Solution: Mechanism and Driving Forces in Nonnative Protein Aggregation", Pharm. Res. 20: 1325-1336 (2003).
Chong and Wong, "Immunobiologics in the Treatment of Psoriasis", Clin. Immunol. 123:129-138 (2007).
Christensen, "Protein as Buffers", Annals of the New York Academy of Sciences. 133(1). Apr. 1, 1966, pp. 34-40.
Claims filed Feb. 2, 2017 in U.S. Appl. No. 15/423,503 (AbbVie).
Claims filed Jun. 14, 2017 in U.S. Appl. No. 15/228,955.
Claims filed May 24, 2017 in U.S. Appl. No. 15/255,018.
Claims filed May 8, 2017 in U.S. Appl. No. 15/231,490.
Claims filed Oct. 20, 2017 in U.S. Appl. No. 15/227,880.
Claims filed Sep. 1, 2016 in U.S. Appl. No. 15/230,039.
Claims filed Sep. 11, 2017 in U.S. Appl. No. 15/698,045.
Claims filed Sep. 13, 2017 in U.S. Appl. No. 15/232,733.
Claims filed Sep. 7, 2017 in U.S. Appl. No. 15/214,377.
Claims filed Feb. 19, 2016 in U.S. Appl. No. 13/797,622.
Claims filed Jul. 26, 2016 in U.S. Appl. No. 13/188,329.
Claims filed Oct. 26, 2018 in U.S. Appl. No. 15/958,261.
Claims filed Sep. 28, 2018 in U.S. Appl. No. 15/788,762.
Cleland & Langer, "Formulation and Delivery of Proteins and Peptides: Design and Development Strategies," Ch. 1 in Formulation and Delivery of Proteins and Peptides, ACS Symposium Series 567, 1-19 (1994).
Cleland J.L. et al., A Specific Molar 1,27,28 Ratio of Stabilizer to Protein is Required for Storage Stability of a Lyophilized Monoclonal Antibody II, Journal of Pharmaceutical Sciences, American Pharm Assoc., Washington, US, vol. 90, No. 3 (Mar. 1, 2001) pp. 310-321.
Cleland, et al. The Development of Stable Protein Formulations: A Close Look at Protein Aggregation, Deamination and Oxidation, Clinical Reviews in Therapeutic Drug Carrier Systems, 10(4), pp. 307-377 (1993).
Clinical Pharmacology and Biopharmaceutics Review(s), by Center for Drug Evaluation and Research and Center for Biologics Evaluation and Research, Application No. 125057/0, in Approval Package for Humira® (Approved Dec. 31, 2002).
Clinical Pharmacology and Therapeutics, vol. 66, No. 2, pp. 205-209, (1999).
Clowse, et al., Efficacy and Safety of Epratuzumab in Moderately to Severely Active Systemic Lupus Erythematosus Arthritis & Rheumatology. 69:362-375 (2016).
CNJ-016 (Vaccinia Immune Globulin Intravenous) Label (Jan. 2010).
Cohn et al., "Preparation and properties of serum and plasma proteins. IV. A system for the separation into fractions of the protein and lipoprotein components of biological tissues and fluids", Separation Into Fractions of Protein and Lipoprotein Components, vol. 68, pp. 459-475, (Mar. 1946).
Collins, K., "Charge Density-Dependent Strength of Hydration and Biological Structure", Biophysical Journal, vol. 72, Jan. 1997, pp. 65-76.
Content of an Extended Registration of Japanese Patent No. 5840364, filed as Exhibit B47 in the Demand for Invalidation Trial against Japanese Patent No. 5856555, in 2 pages (Available from the Internet Website of the Patent Information Platform https://www.j-platpat.inpit.go.jp/; retrieved Apr. 6, 2021), dated Oct. 23, 2019.
Corrected Notice of Allowability for U.S. Appl. No. 13/797,622 in 6 pages, dated May 5, 2022.
Corrected pp. 87-88 of declaration of Geoffrey Lee, Ph.D. dated Mar. 13, 2017 in Interference No. 106,057, involving U.S. Appl. No. 13/797,622 and U.S. Appl. No. 13/188,329 and U.S. Pat. No. 8,420,081.
Correction and Opinion for U.S. Appl. No. 11/338,138, filed as Exhibit A43 in the Demand for Invalidation Trial against Japanese Patent No. 6293103 in 18 pages, dated Jan. 7, 2009.
Counterargument by Demandant with English translation filed in the Demand for Invalidation Trial against Japanese Patent No. 5856555 in 128 pages, dated Jan. 19, 2022.
Counterargument by the Demandant with English Translation dated Mar. 19, 2021, filed in the Demand for Invalidation Trial against Japanese Patent No. 6293103, in 392 pages.
Curtis et al., Injection-Site Burning and Stinging in Patients With Rheumatoid Arthritis Using Injectable Biologics. Curr Med Res Opin. Jan. 2011; 27: pp. 71-78.
Dani, B. et al., "Pharmaceutics, Preformulation, and Drug Delivery—High Concentration Formulation Feasibility of Human Immunoglobulin G for Subcutaneous Administration", Journal of Pharmaceutical Sciences, Jun. 2007, vol. 96, No. 6, pp. 1504-1517.
Dantal, Intravenous Immunoglobulins: In-Depth Review of Excipients and Acute Kidney Injury Risk, Am. J. Nephrol. 2013; 38; 275-284.
Daugherty, et al., "Formulation and Delivery Issues for Monoclonal Antibody Therapeutics," Advanced Drug Delivery Reviews, May 2006, vol. 58, pp. 686-706.
Davies and Metzger, "Structural Basis of Antibody Function", Annu. Rev. Immunol. 1:87-117 (1983).
Dean, "Lange's Handbook of Chemistry," McGraw-Hill, p. 8.49-8.65 (9th ed. 1999).
Decision Denying Institution of Inter Partes Review, dated Sep. 7, 2017 in the Patent Trial and Appeal Board, United States Patent and Trademark Office, Petition No. PTAB-IPR2017-00822.
Decision Denying Institution of Inter Partes Review, dated Sep. 7, 2017 in the Patent Trial and Appeal Board, United States Patent and Trademark Office, Petition No. PTAB-IPR2017-00823.
Decision Denying Institution of Inter Partes Review, dated Sep. 7, 2017 in the Patent Trial and Appeal Board, United States Patent and Trademark Office, Petition No. PTAB-IPR2017-01008.
Decision Denying Institution of Inter Partes Review, dated Sep. 7, 2017 in the Patent Trial and Appeal Board, United States Patent and Trademark Office, Petition No. PTAB-IPR2017-01009.
Decision—Motions—Board Rule 121(a), dated Sep. 27, 2017 in Interference No. 106,057, involving U.S. Appl. No. 13/797,622 and U.S. Appl. No. 13/188,329 and U.S. Pat. No. 8,420,081.
Decision on whether or not to Approve Amendment filed in the Demand for Invalidation Trial against Japanese Patent No. 6293103 in 9 pages, dated Dec. 1, 2021.
Decision-125(b); Order-Miscellaneous dated Dec. 11, 2017 in Interference No. 106,057, involving U.S. Appl. No. 13/797,622 and U.S. Appl. No. 13/188,329 and U.S. Pat. No. 8,420,081.
Declaration of David D. Sherry, M.D Dated Feb. 26, 2017. in the Patent Trial and Appeal Board, United States Patent and Trademark Office, Petition No. PTAB-IPR2017-01008.
Declaration of David D. Sherry, M.D Dated Feb. 26, 2017. in the Patent Trial and Appeal Board, United States Patent and Trademark Office, Petition No. PTAB-IPR2017-01009.
Declaration of David D. Sherry, M.D. Dated Jan. 31, 2017 in the Patent Trial and Appeal Board, United States Patent and Trademark Office, Petition No. PTAB-IPR2017-00826.
Declaration of David D. Sherry, M.D. Dated Jan. 31, 2017 in the Patent Trial and Appeal Board, United States Patent and Trademark Office, Petition No. PTAB-IPR2017-00827.
Declaration of Dr. R. Matthew Fesinmeyer in Support of Amgen Inc. filed in the Demand for Invalidation Trial against Japanese Patent No. 6293103 in 7 pages, dated Aug. 4, 2021.

(56) References Cited

OTHER PUBLICATIONS

Declaration of Geoffrey Lee, Ph.D. (supplemental), dated Feb. 16, 2017 in Interference No. 106,057, involving U.S. Appl. No. 13/188,329 and U.S. Appl. No. 13/188,329 and U.S. Pat. No. 8,420,081.
Declaration of Interference dated May 18, 2016, in Interference No. 106,057, involving U.S. Pat. No. 8,420,081 and U.S. Appl. No. 13/797,622.
Declaration of Klaus-Peter Radtke, Ph.D. Dated Feb. 28, 2017, in the Patent Trial and Appeal Board, United States Patent and Trademark Office, Petition No. PTAB-IPR2017-01008.
Declaration of Klaus-Peter Radtke, Ph.D. Dated Feb. 28, 2017, in the Patent Trial and Appeal Board, United States Patent and Trademark Office, Petition No. PTAB-IPR2017-01009.
Declaration of Klaus-Peter Radtke, Ph.D. Dated Jan. 31, 2017, in the Patent Trial and Appeal Board, United States Patent and Trademark Office, Petition No. PTAB-IPR2017-00822.
Declaration of Klaus-Peter Radtke, Ph.D. Dated Jan. 31, 2017, in the Patent Trial and Appeal Board, United States Patent and Trademark Office, Petition No. PTAB-IPR2017-00823.
Declaration of Klaus-Peter Radtke, Ph.D. Dated Jan. 31, 2017, in the Patent Trial and Appeal Board, United States Patent and Trademark Office, Petition No. PTAB-IPR2017-00826.
Declaration of Klaus-Peter Radtke, Ph.D. Dated Jan. 31, 2017, in the Patent Trial and Appeal Board, United States Patent and Trademark Office, Petition No. PTAB-IPR2017-00827.
Declaration of Mark C. Manning, Ph.D. dated May 6, 2016 from IPR2017-01008, Ex. 2004.
Declaration of Richard L. Remmele, Jr. dated Jul. 24, 2009 in U.S. Appl. No. 11/784,538, also Ex. 1044 in IPR2017-01823.
Declaration of Richard L. Remmele, Jr. dated Jul. 5, 2016 from IPR2017-01823, Ex.1002.
Demand for Invalidation Trial against Japanese Patent No. 5856555, dated Mar. 31, 2020.
Demand for Invalidation Trial against Japanese Patent No. 6293103, dated Jun. 30, 2020.
Demandant Explanatory Material Slides presented in the Demand for Invalidation Trial against Japanese Patent No. 5856555 in 66 pages, dated May 20, 2021.
Demandant's Petition filed in Demand for Invalidation Trial in Japanese Patent No. 5856555, Dated Dec. 28, 2020 (with English translation).
Demandee (Patentee) Explanatory Material Slides presented in the Demand for Invalidation Trial against Japanese Patent No. 5856555 in 177 pages, dated May 20, 2021.
Deposition Transcript of Geoffrey Lee, Ph.D., dated Mar. 13, 2017 in Interference No. 106,057, involving U.S. Appl. No. 13/797,622 and U.S. Appl. No. 13/188,329 and U.S. Pat. No. 8,420,081.
Description of Evidence by Demandant filed in the Demand for Invalidation Trial against Japanese Patent No. 5856555, dated May 6, 2021, in 15 pages.
Description of Evidence by Demandee filed in the Demand for Invalidation Trial against Japanese Patent No. 5856555, dated Jun. 17, 2021, in 4 pages.
Description of Evidence Dated Dec. 10, 2020 in 14 pages filed in the response to the Demand for Invalidation Trial in Japanese Patent No. 6293103.
Description of Evidence filed in the Demand for Invalidation Trial against Japanese Patent No. 5856555, dated Apr. 8, 2021, in 13 pages.
Description of Evidence in Demand for Invalidation Trial against Japanese Patent No. 5856555, dated Mar. 31, 2020.
Description of Evidences (2) filed in the Demand for Invalidation Trial against Japanese Patent No. 6293103 in 11 pages, dated Mar. 19, 2021.
Description of Evidences (3) filed in the Demand for Invalidation Trial against Japanese Patent No. 6293103 in 8 pages, dated Aug. 6, 2021.
Description of Evidences by Demandee filed in the Demand for Invalidation Trial against Japanese Patent No. 6293103 in 9 pages, dated Aug. 6, 2021.
Description of Evidences in Demand for Invalidation Trial against Japanese Patent No. 6293103, dated Jun. 30, 2020.
DiJoseph et al., "Antibody-Targeted Chemotherapy with CMC-544; a CD22-targeted Immuconjugate of Calichemicin for the Treatment of B-Lymphoid Malignancies", Blood 103:1807-1814 (2004).
Dijoseph, J. et al., "Antibody-targeted chemotherapy of B-cell lymphoma using calicheamicin conjugated to murine or humanized antibody against CD22", Cancer Immunology Immunotherapy, vol. 54, Jan. 2005, pp. 11-24.
Draft Notice of Issues to be Examined dated Feb. 1, 2021, in the Demand for Invalidation Trial against Japanese Patent No. 5856555, in 8 pages.
Egan, "Biotechnology in Drug Research Experimental, Toxicological and Clinical Aspects", Arzneimittelforschung 49:779-790 (1999).
EMBREL (etamercept) label, dated Dec. 2012.
EMBREL (etamercept) label, dated Nov. 2017.
ENBREL® Label (2004).
ENBREL® Label (Nov. 1998).
ENBREL® Label (Sep. 2002).
Endobulin S/D label, text revised Jul. 1999 (with machine translation).
Eurasian Office Action for EA Application No. 201990998 with English translation in 6 pages, dated Dec. 8, 2021.
European Medical Agency. Initial Scientific Discussion for the Approval of Trudexa. Copyright 2004, EMEA.
Executed Transcript of Deposition Transcript of Andrew Zydney dated Jan. 13, 2017 (with errata sheet) in Interference No. 106,057, involving U.S. Appl. No. 13/797,622 and U.S. Appl. No. 13/188,329 and U.S. Pat. No. 8,420,081.
Executed Transcript of Deposition Transcript of Peter Tessier dated Jan. 5, 2017 (with errata sheet) in Interference No. 106,057, involving U.S. Appl. No. 13/797,622 and U.S. Appl. No. 13/188,329 and U.S. Pat. No. 8,420,081.
Exhibit 19 Prescription drug injection for specified bio-derived products in 9 pages, issued Aug. 2018, filed in the response to the Demand for Invalidation Trial in Japanese Patent No. 6293103.
Exhibit 21 Office Action Summary dated Sep. 15, 2008 in U.S. Appl. No. 11/338,138 in 14 pages filed in the response to the Demand for Invalidation Trial in Japanese Patent No. 6293103.
Exhibit 22 Amendment Filed Jan. 24, 2006 in U.S. Appl. No. 11/338,138 in 9 pages filed in the response to the Demand for Invalidation Trial in Japanese Patent No. 6293103.
Exhibit 23 Written notice of reasons for refusal dated Jan. 28, 2020 in 8 pages filed in the response to the Demand for Invalidation Trial in Japanese Patent No. 6293103.
Exhibit 24 Amendment Submitted Jul. 3, 2009 in Japanese Patent Application No. 2002-592966 in 18 pages filed in the response to the Demand for Invalidation Trial in Japanese Patent No. 6293103.
Exhibit 25 Opinion Form Submitted Jul. 3, 2009 in Japanese Patent Application No. 2002-592966 in 12 pages filed in the response to the Demand for Invalidation Trial in Japanese Patent No. 6293103.
Expert Opinion of Prof. Fumio Arisaka, dated Mar. 30, 2020, in Demand for Invalidation Trial against Japanese Patent No. 5856555 (Exhibit A22).
Extended European Search Report dated Apr. 2, 2020 in Application No. 17862991.1.
Extended European Search Report Dated Apr. 26, 2018 in European Application No. EP 17205734.1.
Fayos, et al., "On the Origin of the Thermostabilization of Proteins Induced by Sodium Phosphate," J. Am. Chem. Soc. 127(27), pp. 9690-9691. 2005.
Fesinmeyer, et al., Effect of Ions on Agitation- and Temperature-Induced Aggregation Reactions of antibodies. Pharmaceutical Research, Apr. 2009, vol. 26: pp. 903-913.
Fesinmeyer, RM, Presentation at AAPS National Biotechnology Conference, Jun. 24-27, 2007, San Diego Convention Center.
File History of U.S. Appl. No. 15/958,261.
File History of Int'l Patent Application No. PCT/US2006/022599, filed Jun. 8, 2006.
File History of U.S. Appl. No. 15/214,377, filed Jul. 19, 2016.
File History of U.S. Appl. No. 15/227,880, filed Aug. 3, 2016.
File History of U.S. Appl. No. 15/228,955, filed Aug. 4, 2016.
File History of U.S. Appl. No. 15/230,039, filed Aug. 5, 2016.

(56) References Cited

OTHER PUBLICATIONS

File History of U.S. Appl. No. 15/231,490, filed Aug. 8, 2016.
File History of U.S. Appl. No. 15/232,733, filed Aug. 9, 2016.
File History of U.S. Appl. No. 15/255,018, filed Sep. 1, 2016.
File History of U.S. Appl. No. 15/341,962, filed Nov. 2, 2016.
File History of U.S. Appl. No. 15/698,405.
File History of U.S. Appl. No. 15/788,762.
File History of U.S. Appl. No. 16/246,202, filed Nov. 1, 2019.
File History of U.S. Appl. No. 16/396,352, filed Apr. 26, 2019.
File History of U.S. Appl. No. 13/188,329, filed Jul. 21, 2011.
File History of U.S. Appl. No. 11/917,188, having a 371 (c) date of Jun. 16, 2008.
File History of U.S. Appl. No. 12/325,049, filed Nov. 28, 2008.
File History of U.S. Appl. No. 13/797,622, filed Mar. 12, 2013.
File History of U.S. Appl. No. 13/797,690, filed Mar. 12, 2013.
Final Amendment date Jul. 26, 2016 in U.S. Appl. No. 13/188,329.
Final Office Action Dated May 18, 2017 in U.S. Appl. No. 15/231,490.
Final Rejection dated Feb. 1, 2016 in U.S. Appl. No. 13/797,622.
Finlayson et al., "Reversibility of Human Immunoglobulin G Dimerization", In Lindgren et al, eds., Radiobiologic Investigations, Acta Radiologica, 1971, pp. 114-123.
First Declaration of Peter Tessier, Ph.D., dated Oct. 11, 2016.
Fisher Scientific Safety Data Sheet for Phosphate Buffered Saline Solution (creation date Sep. 22, 2009; Revision Date Apr. 10, 2014).
Flebogamma Label (Jan. 2004).
Fleischmann et al., "Does safety make a difference in selecting the right TNF antagonist?" Arthritis Research & Therapy 2004; vol. 6 Suppl 2 pp. S12-S28.
Fransson et al., Local Tolerance of Subcutaneous Injection. J. Pharm. Pharmacol. 1996: 48, pp. 1012-1015.
Fraunhofer Exhibit List 3 over Fraunhofer's U.S. Pat. No. 8,420,081 dated Oct. 31, 2016 in Interference No. 106,057, involving U.S. Appl. No. 13/797,622 and U.S. Appl. No. 13/188,329 and U.S. Pat. No. 8,420,081.
Fraunhofer Motions List dated Jul. 27, 2016 in Interference No. 106,057, in 23 pages.
Fraunhofer Objections to Evidence 1, Served Feb. 7, 2017 in Interference No. 106,057, involving U.S. Appl. No. 13/797,622 and U.S. Appl. No. 13/188,329 and U.S. Pat. No. 8,420,081.
Fraunhofer Substantive Motion 1 (for judgment based on 35 U.S.C. § 135(b)(1) over Fraunhofer's U.S. Pat. No. 8,420,081) dated Oct. 12, 2016 in Interference No. 106,057, involving U.S. Appl. No. 13/797,622 and U.S. Appl. No. 13/188,329 and U.S. Pat. No. 8,420,081.
Fraunhofer Substantive Motion 2 (for judgment based on 35 U.S.C. § 112 second paragraph) dated Oct. 12, 2016 in Interference No. 106,057, involving U.S. Appl. No. 13/797,622 and U.S. Appl. No. 13/188,329 and U.S. Pat. No. 8,420,081.
Fraunhofer Substantive Motion 3 (to substitute proposed Count A for Count 1) dated Oct. 12, 2016 in Interference No. 106,057, involving U.S. Appl. No. 13/797,622 and U.S. Appl. No. 13/188,329 and U.S. Pat. No. 8,420,081.
Fraunhofer Substantive Motion 4 (to vacate benefit of Gokarn U.S. Appl. No. 13/188,329) dated Oct. 12, 2016 in Interference No. 106,057, involving U.S. Appl. No. 13/797,622 and U.S. Appl. No. 13/188,329 and U.S. Pat. No. 8,420,081.
Fraunhoffer Miscellaneous Motion 5 to Exclude Evidence dated Apr. 5, 2017 in Interference No. 106,057, involving U.S. Appl. No. 13/797,622 and U.S. Appl. No. 13/188,329 and U.S. Pat. No. 8,420,081.
Fraunhoffer Reply 1 dated Mar. 25, 2017 in Interference No. 106,057, involving U.S. Appl. No. 13/797,622 and U.S. Appl. No. 13/188,329 and U.S. Pat. No. 8,420,081.
Fraunhoffer Reply 2 dated Mar. 25, 2017 in Interference No. 106,057, involving U.S. Appl. No. 13/797,622 and U.S. Appl. No. 13/188,329 and U.S. Pat. No. 8,420,081.
Fraunhoffer Reply 3 dated Mar. 25, 2017 in Interference No. 106,057, involving U.S. Appl. No. 13/797,622 and U.S. Appl. No. 13/188,329 and U.S. Pat. No. 8,420,081.
Fraunhoffer Reply 4 dated Mar. 25, 2017 in Interference No. 106,057, involving U.S. Appl. No. 13/797,622 and U.S. Appl. No. 13/188,329 and U.S. Pat. No. 8,420,081.
Fraunhoffer Reply 5 dated Apr. 25, 2017 in Interference No. 106,057, involving U.S. Appl. No. 13/797,622 and U.S. Appl. No. 13/188,329 and U.S. Pat. No. 8,420,081.
Frenken et al., "Identification of the Component Part in an Epoetin Alfa Preparation that Causes Pain After Subcutaneous Injection." American J. Kidney Dis. 1992; 22: pp. 553-556.
Gallagher, E. et al, Reliability and Validity of a Visual Analog Scale for acute Abdominal Pain in the Ed., American Journal of Emergency Medicine, pp. 287-290, (2002).
Gamimune Label (Oct. 2005).
Gamimune® label (1986) (Exhibit A8).
Gammagard Liquid Label (Apr. 2005).
Gammagard S/D, Immune Globulin Intravenous (Human) label, initial US Approval 1994, revised 2014.
Gamunex Label (Nov. 2005).
Gatlin & Gatlin, "Formulation and Administration Techniques to Minimize Injection Pain and Tissue Damage Associated with Parenteral Products," Chapter 17 of Injectable Drug Development: Techniques to Reduce Pain and Irritation (Eds. Gupta & Brazeau) (1999).
Gebhart, "Biotech Company Preparing Several Drugs for Take-off," Drug Topics, vol. 145, No. 5, p. 50 (Mar. 5, 2001).
Gelfand, "Differences Between IGIV Products: Impact on Clinical Outcome," Int'l Immunopharmacology, 6:592-99 (2006).
Gokarn et al., "Excipients for Protein Drugs," Ch. 17 in Excipient Development for Pharmaceutical, Biotechnology, and Drug Delivery Systems (Ashok Katdare & Mahesh V. Chaubal eds., 2006).
Gokarn et al., "Self-buffering antibody formulations," Journal of Pharmaceutical Sciences, American Pharmaceutical Association, Washington, US, vol. 97, No. 8 (Aug. 2008), pp. 3051-3066. First published Nov. 19, 2007.
Gokarn Opposition 1 dated Jan. 31, 2017 in Interference No. 106,057, involving U.S. Appl. No. 13/797,622 and U.S. Appl. No. 13/188,329 and U.S. Pat. No. 8,420,081.
Gokarn Opposition 2 dated Jan. 31, 2017 in Interference No. 106,057, involving U.S. Appl. No. 13/797,622 and U.S. Appl. No. 13/188,329 and U.S. Pat. No. 8,420,081.
Gokarn Opposition 3 dated Jan. 31, 2017 in Interference No. 106,057, involving U.S. Appl. No. 13/797,622 and U.S. Appl. No. 13/188,329 and U.S. Pat. No. 8,420,081.
Gokarn Opposition 4 dated Jan. 31, 2017 in Interference No. 106,057, involving U.S. Appl. No. 13/797,622 and U.S. Appl. No. 13/188,329 and U.S. Pat. No. 8,420,081.
Gokarn Oppostion to Miscellaneous Motion 5 to Exclude Evidence dated Apr. 1, 2017 in Interference No. 106,057, involving U.S. Appl. No. 13/797,622 and U.S. Appl. No. 13/188,329 and U.S. Pat. No. 8,420,081.
Gomez, G. et al., "Effect of Initial Buffer Composition on pH Changes During Far-From-Equilibrium Freezing of Sodium Phosphate Buffer Solutions", Pharmaceutical Research, vol. 18(1), Jan. 2001, pp. 90-97.
Gottlieb, "Efficacy and Safety of Anti-TNF-a Agents in Psoriasis," in Anti-TNF-a Therapies in the Treatment of Dermatologic Diseases at 6 (2005) (Supplement to Skin & Allergy News; Produced in Affiliation with the Skin Disease Education Foundation's 29th Annual Hawaii Dermatology Seminar).
Gottschalk, U., "Downstream Processing of Monoclonal Antibodies: from High Dilution to High Purity", BioPharm International, vol. 18, Issue 6, Jun. 2005, in 18 pages. (available at https://www.biopharminternational.com/view/downstream-processing-monoclonal-antibodies-high-dilution-high-purity).
Granolleras et al., "Experience of Pain After Subcutaneous Administration of Different Preparations of Recombinant Human Erythropoietin: A Randomized, Double-Blind Crossover Study," Clinical Nephrology, 36:294-298 (1991).
Gras et al., "Curvas de electrotitulacion de globulina gamma" R. esp. Fisiol. 1959. 15(4): 273-78. (Exhibit A6).
Gronski et al., "On the Nature of IgG Dimers—I. Dimers in Human Polyclonal IgG Preparations: Kinetic Studies", Behring Inst. Mitt., 1988, No. 82, pp. 127-143.

(56) References Cited

OTHER PUBLICATIONS

Halvor, N. Christensen, "Proteins as Buffers," Annals of the New York Academy of Sciences, vol. 133, No. 1 Current Concepts (Apr. 1, 1966), pp. 34-40.
Handbook of Pharmaceutical Excipients, Pharmaceutical Press (Raymond C. Rowe, Paul J. Sheskey, & Sian C. Owen eds., 5th ed. 2006).
Hanna, The IGIV-C Study Group, "Tolerability of a New Intravenous Immunoglobulin Preparation (IGIV) in Pediatric and Adult Patients," presented at the 60th Anniversary Meeting of the American Academy of Allergy, Asthma & Immunology (Mar. 10, 2003), in J. Allergy Clinical Immunology, vol. 111, No. 2, part 2, a631.
Hardcastle, "Buffer Action of Proteins", J. Chem. Ed. 58: pp. 725-726 (1981).
Harinayaran et al., "Small Molecule Clearance in Ultrafiltration/Diafiltration in Relation to Protein Interactions: Study of Citrate Binding to a Fab", Biotech. Bioeng. 102:1718-1722 (2009).
Harlow and Lane, Antibodies: A Laboratory Manual, Cold Spring Harbor, NY: Cold Spring Harbor Laboratory, pp. 1-22 (1988).
Helms, et al., "Destabilizing Loop Swaps in the CDRs of an Immunoglobin VL Domain," Protein Sci. 4, pp. 2073-2081. 1995.
HepaGam B Summary Basis for Approval (Jan. 2006).
Herceptin® (trastuzumab) Label, 1-28 (2002).
Herceptin® (trastuzumab), Physicians' Desk Reference, PDR 57, Thomson PDR, Montvale, NJ, pp. 1399-1402 (2003).
Hooper, J. Intravenous immunoglobulins: evolution of commercial IVIG preparations. Immunol Allergy Clin North Am. Nov. 2008;28(4):765-78, viii.
Hora, et al. Lyophilized Formulations of Recombinant Tumor Necrosis Factor, Pharmaceutical Research, 9(1), pp. 33-36, (1992).
Humblet, Cetuximab: an IgG1 Monoclonal Antibody for the Treatment of Epidermal Growth Factor Receptorexpressing Tumours Expert Opin. Pharmacother., 5:1621-1633 (2004).
Humira® Label (Feb. 2007).
Humira® Label (Feb. 2008).
Humira® Label (Nov. 2006).
Humira® Label (Oct. 2005).
Humira Label (Jan. 2003).
Humira Label (Jan. 2008).
Humira Label (Japan), revised 2020 (initial approval 2018) (in Japanese) with machine translation.
Humira Label (Nov. 2015).
Humira Label (Oct. 2016).
Humira Product label, dated Dec. 31, 2002.
Humira Product label, dated Jul. 30, 2004.
Humira® (adalimumab) Label, 1-16 (2002).
Humira® (adalimumab), Physicians' Desk Reference, PDR 58, Thomson PDR, Montvale, NJ, pp. 470-474 (2004).
Humphreys, "Top 200 Medicines—Special Report," Pharmalive, http://www.pharmalive.com/special-report-top-200-medicines/. Aug. 12, 2015.
Hypermol, "Dialysis: an introduction," Dialysis: Technical Datasheet, 1-2 (2008).
I. Suzuki (Ed.), "Zoku, Iyakuhin-no-Kaihatsu,", Hirokawa Publishing Co., Tokyo, 1992. 19-68, 105-114, 134-135 (Exhibit A12).
I. Suzuki (Ed.), "Zoku, Iyakuhin-no-Kaihatsu,", Hirokawa Publishing Co., Tokyo, 1992. 19-68, 105-114, 134-135 (Exhibit A12) translation of p. 44 included.
Immunex Corporation, "ENBREL", dated Dec. 1, 2006, retrieved from the Internet: URL: https://www.accessdata.fda.gov/drugsatfda_docs/label/2008/enbrel_pi.pdf, retrieved on Feb. 17, 2020.
Intention to Grant dated Aug. 16, 2019 for European Patent Application No. EP 17 205 734.1.
International Preliminary Report on Patentability dated Apr. 23, 2019 in International Application No PCT/US2017/057472.
International Preliminary Report on Patentability dated Dec. 17, 2007 in PCT App. No. PCT/US2006/022599.
International Search Report and Written Opinion dated May 12, 2009 in PCT App. No. PCT/US2008/085066.
International Search Report and Written Opinion dated Oct. 12, 2007 in PCT App. No. PCT/US2006/022599.
International Search Report Dated Jan. 12, 2018 in International Application No PCT/US2017/057472.
Ipp, et al., "Adverse Reactions to Diptheria, Tetanus, Pertussis-Polio Vaccination at 18 Months of Age: Effect of injection Site and Needle Length," Pediatrics 83(5): pp. 679-682. May 1989.
Isemura, "Tanpakushitsu Kagaku," vol. 2, Kyoritsu Shuppan Co., Ltd., (1st edn.) Tokyo, 1979, 40-47. (Exhibit A4).
Iwanami's Biology Dictionary, 4th ed., 1996, p. 1406, filed as Exhibit A37 in the Demand for Invalidation Trial against Japanese Patent No. 6293103, in 4 pages (with partial English translation).
Iwanami's Dictionary of Physics and Chemistry, 5th ed., 1998, p. 104, filed as Exhibit A27 in the Demand for Invalidation Trial against Japanese Patent No. 6293103, in 5 pages (with partial English translation).
Jefferis et al., "Recognition Sites on Human IgG for Fcγ Receptors: The Role of Glycosylation," Immunology Letters, 44: 111-117 (1995).
Jorgensen, "Improvement of Patient Convenience in Treatment with Growth Hormone," J. Pediatric Endocrinology 7(2), pp. 175-180. 1994.
Jorgensen, et al., "Pain Assessment of Subcutaneous Injections," Ann. Pharmacotherapy 30, pp. 729-732. Jul./Aug. 1996.
Judgment dated Dec. 20, 2017 in Interference No. 106,057, involving U.S. Appl. No. 13/797,622 and U.S. Appl. No. 13/188,329 and U.S. Pat. No. 8,420,081.
K. Imabori, T. Yamakawa, K. Inoue (Eds.), Seikagaku Jiten [Dictionary of Biochemistry] (3rd edn.), Tokyo Kagaku Doujin, Tokyo (1998) 333-35, 986 (Exhibit A3).
K. Imabori, T. Yamakawa, K. Inoue (Eds.), Seikagaku Jiten [Dictionary of Biochemistry] (3rd edn.), Tokyo Kagaku Doujin, Tokyo (1998) 334-35 (Exhibit A3).
Kalden, J., Emerging Role of Anti-Tumor Necrosis Factor Therapy in Rheumatic Diseases, Arthritis Research, vol. 4, Sup. 2, pp. S34-S40, (2002).
Kamerzell, et al., "Increasing IgG Concentration Modulated the Conformational Heterogeneity and Bonding Network that Influence Solution Properties," J. Phys. Chem. B. 113(17), pp. 6109-6118. 2009.
Kaminiski, M.S., et al., Pivotal Study of Iodine I 131 Tositumomab for Chemotherapy-Refractory Low-Grade or Transformed Low-Grade B-Cell Non-Hodgkin's Lymphomas, Journal of Clinical Oncology, vol. 19, No. 19, pp. 3918-3928, 2001.
Kaminski, M.S., et al., Radioimmunotherapy of B-Cell Lymphoma with [131I]Anti-B1 (Anti-CD20) Antibody, The New England Journal of Medicine, vol. 329, No. 7, pp. 459-465, 1993.
Kappelgaard, et al., Liquid Growth Hormone: Preservatives and Buffers. Horm Res 2004;62(suppl 3): pp. 98-103.
Karas, M. et al., "Membrane-associated Insulin-like Growth Factor-binding Protein-3 Inhibits Insulin-like Growth Factor-I-induced Insulin-like Growth Factor-I Receptor Signaling in Ishikawa Endometrial Cancer Cells", The Journal of Biological Chemistry, vol. 272, No. 26, Jun. 1997, pp. 16514-16520.
Katdare et al, eds., Excipient Development for Pharmaceutical Biotechnology and Drug Delivery Systems, 1st Ed., Informa Healthcare USA, Inc., New York, 2006.
Kempeni, Preliminary results of early clinical trials with the fully human anti-TNF α monoclonal antibody D2E7. Ann. Rheum. Dis. 1999; 58(Suppl): 170-172.
Kerry, P. J et al., "Standardization of prekallikrein activator (PKA): the 1st International Standard for PKA", British Journal of Haematology, vol. 60, Jun. 1985, pp. 345-352.
Khayyamian, S. et al., "ICOS-ligand, expressed on human endothelial cells, costimulates Th1 and Th2 cytokine secretion by memory CD4+ T cells", PNAS, vol. 99, No. 9, Apr. 2002, pp. 6198-6203.
Kim et al., Diffusivity of Protein in Aqueous Solution. Korean J. Chem. Eng., 1996; 13: pp. 288-297.
Kim, N. et al., "Effects of pH Buffer Concentration on the Thermal Stability of Etanercept Using DSC and DLS", Biol. Pharm. Bull., May 2014, vol. 37(5), pp. 808-816.
Koticha et al., "Rapid Antibody Purification Using Ultrafiltration and Centrifugal Affinity Columns," BioscienceTechnologies.com,

(56) References Cited

OTHER PUBLICATIONS accessible on the world wide web at www.biosciencetechnology.com/article/2006/07/rapid-antibody-purification-usingultrafiltration-and-centrifugal-affinity-columns. As this is a webpage, the earliest publication date is not apparent on the document itself. However, the document specifies a date of Jul. 17, 2006.

Kotz and Treichel, "Principles of Reactivity: Reactions Between Acids and Bases" Chem. & Chem. Reactivity, Chapter 18:Unit 18.3, pp. 851-858 (1999).

Kurnik et al, Buffer Exchange Using Size Exclusion Chromatography, Countercurrent Dialysis, and Tangential Flow Filtration: Models, Development, and Industrial Application, Biotechnology and Bioengineering, vol. 45, 149-157, 1995.

Kuzu, et al., "The Effect of Cold on the Occurrence of Bruising, Haematoma and Pain at the Injection Site in Subcutaneous Low Molecular Weight Heparin," Int't J. Nursing Studies 38, pp. 51-59. 2001.

Lam et al., "Antioxidants for prevention of methionine oxidation in recombinant monoclonal antibody HER2", J. Pharm. Sci. 86(11):1250-1255 (1997).

Laursen et al, "Pain perception after subcutaneous injections of media containing different buffers," Basic Clin. Pharmacol Toxicol. Feb. 2006; 98:218-21.

Lee, et al., "Toward Aggregation-resistant Antibodies by Design," Trends in Biotech. 31(11), pp. 612-620. 2013.

Levine et al., "The use of surface tension measurements in the design of antibody-based product formulations", J. Parenteral Science & Technology 45(3):160-165 (1991).

Li et al., Resurrecting Abandoned Proteins with Pure Water: CD and NMR Studies of Protein Fragments Solubilized in Salt-Free Water. Biophysical Journal Dec. 2006; 91: pp. 4201-4209.

Lide, CRC Handbook of Chemistry and Physics, 81st ed., Boca Raton, FL: CRC Press., pp. 7-1, 8-44 to 8-56 (2000).

Lipman et al., Monoclonal Versus Polyclonal Antibodies: Distinguishing Characteristics, Applications, and Information Resources ILAR J.46(3):258-68. (2005).

Lista immunoglobuline in italia, Accessed from the world wide web at http://wp.aip-it.org/wp-content/uploads/2013/03/lista_immunoglobuline_in_italia.pdf. This document is from the world wide web, and no date of publication is immediately apparent in the document. As this is a webpage, the earliest publication date is not apparent on the document itself. However, the document specifies that it was last updated Dec. 2007.

Liu et al. Reversible Self-Association Increases the Viscosity of a Concentrated Monoclonal Antibody in Aqueous Solution. J. Pharmaceutical. Sci. 2005; 94: pp. 1928-1940.

Liu W, et al. Moisture-Induced Aggregation of Lyophilized Proteins in the Solid State, Biotechnology and Bioengineering, vol. 37, pp. 177-184, (1991).

Lopez, E. et al., "Simultaneous Determination of the Major Organic Acids, Sugars, Glycerol, and Ethanol by HPLC in Grape Musts and White Wines ", Journal of Chromatographic Science, May 1996, vol. 34(55), pp. 254-257.

Lovrien et al. Selective Precipitation of Proteins, Current Protocols in Protein Science, 1997, at 4.5.1.

Luo, M., Complete Collection of Pharmaceutical Excipients, Sichuan Science and Technology Publishing House, Dec. 2006, p. 1372.

Maksymowych, W., Novel Therapeutics in the Treatment of Spondyloarthritis, Investig Drugs, vol. 11, No. 7, pp. 478-486, (1999).

Manning, et al. Stability of Protein Pharmaceuticals Pharmaceutical Research, 6(11), pp. 903-918, (1989).

Manual of Patent Examining Procedure § 1101.02: "With a Patent" (2nd ed., Nov. 1953).

Manual of Patent Examining Procedure § 1101.02: "With a Patent" (3rd ed., Nov. 1961).

Manual of Patent Examining Procedure § 2173.03: "Correspondence Between Specification and Claims" (9th ed., Rev. 7, Nov. 2015).

Manual of Patent Examining Procedure § 2309.01: "Formulation of Counts [R-2]" (5th ed. rev. 7, Dec. 1987).

Manual of Patent Examining Procedure 2111.01.V: "How to Determine the Meaning of a Claim Term That Does Not Invoke 35 USC 112(f)".

McCue et al., "Three Generations of Immunoglobulin G Preparations for Clinical Use," Reviews of Infectious Diseases, 8:S374-81 (1986).

McDonnell. "Chapter 3: Production of Antibodies in Hybridoma and Non-hybridoma Cell Lines." In Animal Cell Culture, Cell Engineering 9, Springer International Publishing Switzerland 2015.

Meadows & Hollowell, "Off-label' drug use: an FDA Regulatory Term, Not a Negative Implication of Its Medical Use," Int'l J. Impotence Research 20:135-144 (2008).

Mease, Adalimumab in the treatment of arthritis. Therapeutics and Clinical Risk Management 2007; 3: pp. 133-148.

Meeting Request Dated Aug. 5, 2016 From Amgen to FDA.

Meyssami et al., "Prediction of PH Model Systems Pressurized with Carbon Dioxide", Biotechnol. Prog. 8:149-154 (1992).

Mezzasalma, et al., "Enhancing Recombinant Protein Quality and Yield by Protein Stability Profiling," J. Biomolecular Screening 12(3), pp. 418-428. 2007.

Millipore "Protein Concentration and Diafiltration by Tangential Flow Filtration" http://wolfson.huji.ac.il/purification/PDF/dialysis/MILLIPORE_TFF.pdf, copyright date 2003 (pp. 1-24).

Miscellaneous Communication dated Aug. 3, 2016 in U.S. Appl. No. 13/188,329.

Mohan, "Buffers: A guide for the preparation and use of buffers in biological systems," Calbiochem, 1-32 (2003).

Moreland L et al. Etannercept Therapy in Rheumatoid Arthritis, A Randomized Controlled Trial, Amm Intern Med, vol. 130, pp. 478-486, (1999).

Moreland, L. et al., Treatment of Rheumatoid Arthritis with a Recombinant Human Tumor Necrosis Factor Reactor, New England Journal of Medicine, vol. 337, pp. 141-147 (1997).

Nanzando's Medical Dictionary, 1998, p. 4 and p. 1326, filed as Exhibit A26 in the Demand for Invalidation Trial against Japanese Patent No. 6293103, in 4 pages (with partial English translation).

Naranda, T. et al., "A peptide derived from an extracellular domain selectively inhibits receptor internalization: Target sequences on insulin and insulin-like growth factor 1 receptors", PNAS, vol. 94, Oct. 1997, pp. 11692-11697.

Nash et al. Randomized Crossover Comparison of Injection Site Pain with 40 mg/0.4 or 0.8mL Formulations of Adalimumab in Patients with Rheumatoid Arthritis. Rheumatol. Ther. Jun. 9, 2016.

NCI Dictionary of Cancer Terms, https://www.cancer.gov/publications/dictionaries/cancer-terms, downloaded Oct. 31, 2016; however, as this is a webpage, it may have been accessible in some form prior to Oct. 31, 2016.

Ng, Drugs: From Discovery to Approval, Wiley-Liss, Hoboken, N.J., pp. 159-280 (2004).

Niederkofler, et al., MSIA Workflow for Therapeutic Antibodies: Qualitative, Quantitative, and Functional Verification Data from HR/AM Detection of Intact, Reduced, and Peptide-level Forms of Adalimumab. Thermo Fisher Scientific Inc. Accessed on the world wide web at tools.thermofisher.com/content/sfs/brochures/MSIA-Workflow-for-Therapeutic-Antibodies.pdf. As this is a webpage, the earliest publication date is not apparent on the document itself. However, the document specifies a copyright date of 2014.

Non-Final Rejection dated Jan. 4, 2012 in U.S. Appl. No. 12/325,049.

Non-Final Rejection dated Mar. 2, 2011 in U.S. Appl. No. 12/325,049.

Notice of Abandonment dated Apr. 2, 2018 in U.S. Appl. No. 15/230,039.

Notice of Abandonment dated Aug. 10, 2018 in U.S. Appl. No. 13/188,329.

Notice of Abandonment dated Jan. 7, 2019 in U.S. Appl. No. 15/228,955.

Notice of Abandonment dated Jul. 3, 2018 in U.S. Appl. No. 15/231,490.

Notice of Abandonment dated Jul. 5, 2018 in U.S. Appl. No. 15/232,733.

Notice of Abandonment dated Jun. 11, 2019 in U.S. Appl. No. 15/788,762.

(56) References Cited

OTHER PUBLICATIONS

Notice of Abandonment dated Jun. 25, 2019 in U.S. Appl. No. 15/698,405.
Notice of Abandonment dated Mar. 7, 2016 in U.S. Appl. No. 13/797,690.
Notice of Abandonment dated May 23, 2018 in U.S. Appl. No. 15/255,018.
Notice of Abandonment dated Nov. 1, 2011 in U.S. App. No. 11/917, 188.
Notice of Abandonment dated Nov. 30, 2018 in U.S. Appl. No. 15/227,880.
Notice of Abandonment Dated Oct. 24, 2007 in U.S. Appl. No. 10/376,576.
Notice of Abandonment dated Oct. 26, 2018 in U.S. Appl. No. 15/214,377.
Notice of Acceptance dated Oct. 18, 2019 in South African Application No. 2019/02544.
Notice of Acceptance for Australian Application No. 2017345490 in 3 pages, dated Jun. 27, 2022.
Notice of Allowability for U.S. Appl. No. 13/797,622 in 10 pages, dated Apr. 1, 2022.
Notice of Allowability for U.S. Appl. No. 13/797,622 in 11 pages, dated Dec. 16, 2021.
Notice of Allowability for U.S. Appl. No. 13/797,622 in 6 pages, dated Jan. 11, 2022.
Notice of Allowability for U.S. Appl. No. 13/797,622 in 6 pages, dated Jul. 7, 2022.
Notice of Allowability for U.S. Appl. No. 13/797,622 in 7 pages, dated Jun. 29, 2022.
Notice of Allowance Dated Oct. 18, 2011 in U.S. Appl. No. 12/632,690.
Notice of Allowance dated Apr. 25, 2016 in U.S. Appl. No. 13/797,622.
Notice of Allowance Dated Aug. 15, 2018 in U.S. Appl. No. 13/797,622.
Notice of Allowance dated Aug. 17, 2020 in U.S. Appl. No. 13/797,622.
Notice of Allowance Dated Aug. 4, 2016 in U.S. Appl. No. 14/478,926.
Notice of Allowance Dated Jan. 25, 2019 U.S. Appl. No. 15/958,261.
Notice of Allowance dated Jan. 29, 2021 in U.S. Appl. No. 13/797,622.
Notice of Allowance dated Mar. 11, 2020 in U.S. Appl. No. 13/797,622.
Notice of Allowance dated May 11, 2021 in U.S. Appl. No. 13/797,622 in 12 pages.
Notice of Allowance Dated May 2, 2014 in U.S. Appl. No. 13/401,496.
Notice of Allowance dated Nov. 2, 2020 in U.S. Appl. No. 13/797,622.
Notice of Allowance dated Nov. 26, 2012 in U.S. Appl. No. 12/325,049.
Notice of Allowance Dated Nov. 29, 2018 in U.S. Appl. No. 15/958,261.
Notice of Allowance Dated Sep. 4, 2009 in U.S. Appl. No. 11/784,538.
Notice of Allowance for U.S. Appl. No. 13/797,622 in 12 pages, dated Aug. 23, 2021.
Notice of Allowance for U.S. Appl. No. 13/797,622 in 9 pages, dated Aug. 24, 2022.
Notice of Patent Grant for Korean Application No. 10-2019-7014130 with English translation in 5 pages, dated Jun. 27, 2022.
Notice of Patent Grant for Korean Application No. 10-2021-7042112 with English translation in 6 pages, dated Apr. 6, 2022.
Notice of Reasons for Invalidation filed in the Demand for Invalidation Trial against Japanese Patent No. 5856555 in 45 pages, dated Sep. 29, 2021.
Notice of Reasons for Invalidation filed in the Demand for Invalidation Trial against Japanese Patent No. 6293103 in 64 pages, dated Dec. 1, 2021.
Notice of Withdrawal with English translation filed in the Demand for Invalidation Trial against Japanese Patent No. 5856555 in 2 pages, dated Feb. 17, 2022.
Notice of Withdrawal with English translation filed in the Demand for Invalidation Trial against Japanese Patent No. 6293103 in 2 pages, dated Feb. 17, 2022.
Notification of Readiness to Grant for Eurasian Application No. 201990998 with English translation in 2 pages, dated Jul. 20, 2022.
Nozaki et al, Examination of Titration Behavior, Methods Enzymol., 11: 715-734 (1967).
Octagam Label (Mar. 2004).
Office Action Dated Jan. 20, 2017 in U.S. Appl. No. 15/228,955.
Office Action Dated Jul. 18, 2018 in U.S. Appl. No. 15/341,962.
Office Action dated Apr. 16, 2021 in Eurasian Application No. 201990998 with English Translation.
Office Action dated Apr. 2, 2015 in U.S. Appl. No. 13/188,329.
Office Action dated Apr. 22, 2015 in U.S. Appl. No. 13/797,622.
Office Action dated Apr. 27, 2016 in U.S. Appl. No. 13/188,329.
Office Action dated Apr. 27, 2018 in U.S. Appl. No. 15/227,880.
Office Action dated Apr. 27, 2020 in U.S. Appl. No. 13/797,622.
Office Action Dated Apr. 28, 2016 in EP Patent App. No. 06772779.2.
Office Action Dated Apr. 29, 2009 in U.S. Appl. No. 11/784,538.
Office Action dated Apr. 5, 2021 in Korean Patent Application No. 10-2019-7014130 with English Translation.
Office Action dated Aug. 20, 2020 in Eurasian Application No. 201990998 with English Translation.
Office Action dated Aug. 3, 2015 in U.S. Appl. No. 13/797,690.
Office Action Dated Aug. 6, 2019 in Japanese Application No. 2017-218002.
Office Action Dated Aug. 9, 2006 in U.S. Appl. No. 10/376,576.
Office Action dated Dec. 10, 2014 in U.S. Appl. No. 13/188,329.
Office Action dated Dec. 17, 2020 in Indian Patent Application No. 201917015635.
Office Action Dated Dec. 22, 2017 in U.S. Appl. No. 15/341,962.
Office Action Dated Dec. 8, 2017 in U.S. Appl. No. 15/228,955.
Office Action dated Feb. 1, 2016 in U.S. Appl. No. 13/797,622.
Office Action dated Feb. 17, 2020 in Chilean Application No. 201901053 with English Translation.
Office Action Dated Feb. 4, 2016 in U.S. Appl. No. 14/478,926.
Office Action dated Jan. 13, 2015 in U.S. Appl. No. 13/797,622.
Office Action dated Jan. 15, 2015 in U.S. Appl. No. 13/797,690.
Office Action Dated Jan. 31, 2019 in U.S. Appl. No. 13/797,622.
Office Action Dated Jul. 18, 2017 in Japanese Application No. JP 2015-216447 (with English translation).
Office Action Dated Jul. 26, 2018 in U.S. Appl. No. 15/958,261.
Office Action Dated Jul. 5, 2016 in CA Patent App. No 2,610,839.
Office Action Dated Jul. 5, 2019 in U.S. Appl. No. 13/797,622.
Office Action Dated Jul. 6, 2017 in U.S. Appl. No. 15/232,733.
Office Action dated Jun. 15, 2015 in EP Patent App. No. 08857510.5.
Office Action dated Jun. 15, 2020 in Chilean patent application No. 2019-01053 (AMGN.004CL) with English Translation.
Office Action dated Jun. 18, 2014 in EP Patent App. No. 08857510.5.
Office Action dated Jun. 29, 2017 in U.S. Appl. No. 15/228,955.
Office Action dated Mar. 17, 2020 in Japanese Application No. 2017-218002 with English Translation.
Office Action dated Mar. 21, 2011 in U.S. Appl. No. 11/917,188.
Office Action Dated Mar. 5, 2019 in European Application No EP 17205734.1.
Office Action Dated May 18, 2017 in U.S. Appl. No. 15/230,039.
Office Action Dated May 19, 2011 in U.S. Appl. No. 12/632,690.
Office Action dated May 24, 2017 in U.S. Appl. No. 15/227,880.
Office Action dated May 25, 2021 in Korean Patent Application No. 10-2019-7014130 with English translation.
Office Action dated May 4, 2018 in U.S. Appl. No. 15/698,405.
Office Action dated Nov. 1, 2017 in U.S. Appl. No. 15/232,733.
Office Action Dated Nov. 17, 2005 in U.S. Appl. No. 10/376,576.
Office Action dated Nov. 24, 2020 in Japanese Application No. 2019-520794 with English Translation.
Office Action Dated Nov. 25, 2016 in U.S. Appl. No. 15/232,733.
Office Action Dated Nov. 25, 2016 in U.S. Appl. No. 15/255,018.
Office Action Dated Nov. 26, 2018 in U.S. Appl. No. 15/788,762.
Office Action dated Nov. 7, 2019 in U.S. Appl. No. 13/797,622.
Office Action Dated Nov. 9, 2016 in U.S. Appl. No. 15/227,880.

(56) References Cited

OTHER PUBLICATIONS

Office Action Dated Nov. 9, 2016 in U.S. Appl. No. 15/230,039.
Office Action Dated Nov. 9, 2016 in U.S. Appl. No. 15/231,490.
Office Action Dated Oct. 15, 2018 in Japanese Application No. 2017-218002 with English Translation.
Office Action Dated Oct. 19, 2016 in JP Patent App. No 2015-216447.
Office Action Dated Oct. 21, 2013 in U.S. Appl. No. 13/401,496.
Office Action Dated Oct. 27, 2017 in European Patent Application No. 06772779.2.
Office Action dated Oct. 30, 2015 in EP Patent App. No. 08857510.5.
Office Action dated Oct. 6, 2017 in U.S. Appl. No. 15/698,405.
Office Action dated Oct. 8, 2015 in U.S. Appl. No. 13/797,622.
Office Action Dated Sep. 11, 2017 in U.S. Appl. No. 15/255,018.
Office Action dated Sep. 17, 2015 in U.S. Appl. No. 13/188,329.
Office Action dated Sep. 22, 2017 in U.S. Appl. No. 15/227,880.
Office Action dated Sep. 5, 2017 in U.S. Appl. No. 15/227,880.
Office Action dated Sep. 5, 2017 in U.S. Appl. No. 15/230,039.
Office Action for Application No. JP 2020-122950 with English translation in 8 pages, dated Jul. 27, 2021.
Office Action for Australian Application No. AU 2017345490 in 2 pages, dated Jul. 30, 2021.
Office Action for Brazilian Application No. BR 1120190078584 with English translation in 6 pages, dated Sep. 15, 2021.
Office Action for Japanese Application No. 2017-218002 with English translation in 28 pages, dated Mar. 29, 2022.
Office Action for Japanese Application No. 2020-122950 with English translation in 6 pages, dated May 31, 2022.
Office Action for Japanese Application No. 2021-080160 with English translation in 7 pages, dated Jun. 28, 2022.
Office Action for Korean Application No. KR 10-2019-7014130 in 6 pages, dated Sep. 23, 2021.
Office Action with English Translation dated Dec. 1, 2020 In Korean Patent Application No. 10- 2019-7014130.
Office Action with English Translation dated Jun. 17, 2021 in Chinese Patent Application No. 201780072322.9.
Office Action with English Translation dated Nov. 30, 2020 In Chinese Patent Application No. 201780072322.9.
Office Communication Dated Dec. 1, 2017 in U.S. Appl. No. 15/231,490.
Office Communication dated Aug. 3, 2016 in U.S. Appl. No. 13/188,329.
Olthuis et al., "Characterization of Proteins by Means of the Buffer Capacity, Measured with an ISFET-based Coulometric Sensor-Actuator System," Biosensors & Bioelectronics, 9:743-751 (1994).
Oncley et al., "The Separation of the Antibodies, Isoagglutinins, Prothrombin, Plasminogen and beta1-lipoprotein Into Subfractions of Human Plasma" 1949. J Am Chem Soc. Feb. 1949;71(2):541-50 (Exhibit A11).
Order—Conference Call—Bd.R. 104(a), dated Oct. 17, 2017 Interference No. 106,057, involving U.S. Appl. No. 13/797,622 and U.S. Appl. No. 13/188,329 and U.S. Pat. No. 8,420,081.
Order Conduct of the Proceeding Dated Apr. 7, 2017 in the Patent Trial and Appeal Board, United States Patent and Trademark Office, Petition Nos. PTAB-IPR2017-00822, PTAB-IPR2017-00823, PTAB-IPR2017-00826, PTAB-IPR2017-00827, PTAB-IPR2017-01008, PTAB-IPR2017-01009.
Order Dismissing the Proceedings Dated Apr. 11, 2017 in the Patent Trial and Appeal Board, United States Patent and Trademark Office, Petition Nos., PTAB-IPR2017-00826, PTAB-IPR2017-00827.
Orlandi, R. et al., "Cloning immunoglobulin variable domains for expression by the polymerase chain reaction", Proc. Natl. Acad. Sci., May 1989, vol. 86, pp. 3833-3837.
Paborji, M. et al, Chemical and Physical Stability of Chimeric L6 a Mouse-Human Monoclonal Antibody, Pharmacuetial Research, Springer New York LLC, vol. 11, No. 5, pp. 764-771, (1994).
Parham et al., "Monoclonal Antibodies: Purification, Fragmentation and Application to Structural and Functional Studies of Class I MHC Antigens" J. Immunol. Methods 53:133-173 (1982).
Parslow, "Immunoglobulins & Immunoglobulin Genes," Ch. 7 in Medical Immunology, Appleton & Lange (Daniel P. Stites, Abba I. Terr, & Tristram G. Parslow eds., 9th ed. 1997).
Patel, K. et al., "Chemical pathways of peptide degradation. II. Kinetics of deamidation of an asparaginyl residue in a model hexapeptide", Pharm. Res., Jul. 1990, vol. 7(7), pp. 703-711.
Patent Oppositions by Abbvie, Inc. dated May 3, 2017 in Australian App. No. 2015242973.
Patent Oppositions by Steven Borovec dated May 3, 2017 in Australian App. No. 2015242973.
Patent Owner's Preliminary Response Dated Jun. 11, 2017 by Coherus BioSciences Inc, in the Patent Trial and Appeal Board, United States Patent and Trademark Office, Petition No. PTAB-IPR2017-00822.
Patent Owner's Preliminary Response Dated Jun. 11, 2017 by Coherus BioSciences Inc, in the Patent Trial and Appeal Board, United States Patent and Trademark Office, Petition No. PTAB-IPR2017-00823.
Patent Owner's Preliminary Response Dated Jun. 11, 2017 by Coherus BioSciences Inc, in the Patent Trial and Appeal Board, United States Patent and Trademark Office, Petition No. PTAB-IPR2017-01008.
Patent Owner's Preliminary Response Dated Jun. 11, 2017 by Coherus BioSciences Inc, in the Patent Trial and Appeal Board, United States Patent and Trademark Office, Petition No. PTAB-IPR2017-01009.
Penin et al., "Structural Biology of Hepatitis C Virus", Hepatology, Jan. 2004, vol. 39, Issue 1, pp. 5-19.
Petition by Demandant filed in the Demand for Invalidation Trial against Japanese Patent No. 5856555 in 40 pages, dated Jul. 9, 2021.
Petition by Demandant filed in the Demand for Invalidation Trial against Japanese Patent No. 6293103 in 29 pages, dated Sep. 10, 2021.
Petition by Demandee filed in the Demand for Invalidation Trial against Japanese Patent No. 5856555, dated Jun. 17, 2021, in 37 pages.
Petition by Demandee filed in the Demand for Invalidation Trial against Japanese Patent No. 6293103 in 12 pages, dated Sep. 10, 2021.
Petition for Extension Filed Jul. 21, 2011 in U.S. Appl. No. 11/917,188.
Petition for Inter Partes Review of U.S. Pat. No. 8,802,100 dated Jul. 20, 2017 by Sandoz, Inc., in the Patent Trial and Appeal Board, United States Patent and Trademark Office, No. IPR2017-01823.
Petition for Inter Partes Review of U.S. Pat. No. 9,085,619 Dated Jan. 31, 2017 42 by Coherus BioSciences Inc, in the Patent Trial and Appeal Board, United States Patent and Trademark Office, Petition No. PTAB-IPR2017-00827.
Petition for Inter Partes Review of U.S. Pat. No. 9,085,619 Dated Jan. 31, 2017 by Coherus BioSciences Inc, in the Patent Trial and Appeal Board, United States Patent and Trademark Office, Petition No. PTAB-IPR2017-00822.
Petition for Inter Partes Review of U.S. Pat. No. 9,085,619 Dated Jan. 31, 2017 by Coherus BioSciences Inc, in the Patent Trial and Appeal Board, United States Patent and Trademark Office, Petition No. PTAB-IPR2017-00823.
Petition for Inter Partes Review of U.S. Pat. No. 9,085,619 Dated Jan. 31, 2017 by Coherus BioSciences Inc, in the Patent Trial and Appeal Board, United States Patent and Trademark Office, Petition No. PTAB-IPR2017-00826.
Petition for Inter Partes Review of U.S. Pat. No. 9,085,619 Dated Mar. 2, 2017 by Coherus BioSciences Inc, in the Patent Trial and Appeal Board, United States Patent and Trademark Office, Petition No. PTAB-IPR2017-01008.
Petition for Inter Partes Review of U.S. Pat. No. 9,085,619 Dated Mar. 2, 2017 by Coherus BioSciences Inc, in the Patent Trial and Appeal Board, United States Patent and Trademark Office, Petition No. PTAB-IPR2017-01009.
Petition for Oral Proceedings by Demandant filed in the Demand for Invalidation Trial against Japanese Patent No. 6293103 in 107 pages, dated Aug. 20, 2021.
Petition under 37 CFR 1.182 for Withdrawal of a Terminal Disclaimer dated Apr. 17, 2020 in U.S. Appl. No. 13/797,622.

(56) References Cited

OTHER PUBLICATIONS

Petitioner's Unopposed Motion to Dismiss Petitions Without Prejudice Dated Apr. 7, 2017 in the Patent Trial and Appeal Board, United States Patent and Trademark Office, Petition Nos., PTAB-IPR2017-00826, PTAB-IPR2017-00827.
Phillips and Signs, Curr. Protoc. Protein Sci., Unit 4.4, pp. 4.4.1-4.4.15, John Wiley & Sons, Inc. (2004).
Physician's Desk Reference, pp. 470-474 (58th ed. 2004) ("2003 Humira Label").
Physicians Desk Reference, for ENBREL Medical Economics, Inc., (2002).
Physicians' Desk Reference entry for GAMUNEX®, pp. 8720876 (59th ed. 2005).
Physicians' Desk Reference, PDR 59, Section 2 Thomson PDR, Montvale, NJ, pp. 101-127 (2005).
Physicians' Desk Reference, PDR 60, Section 2 Thomson PDR, Montvale, NJ, pp. 101-125 (2005).
Physicians' Desk Reference, pp. 558-559, 914-931, 805-807, 2026-2028, 2295-2297, 2524-2525 (56th ed. 2002).
Physicians' Desk Reference, pp. 925-928 (56th ed. 2002) ("Gamimune Label").
Pierce Biotechnology, Inc., "Dialysis; an overview," Technical Resource, 1-2 (2004).
Pikal-Cleland, K. et al., "Lyophilization-induced protein denaturation in phosphate buffer systems: Monomeric and tetrameric β-galactosidase", Journal of Pharmaceutical Sciences, vol. 90(9), Sep. 2001, pp. 1255-1268.
Piper and Fenton, "PH Stability and Activity Curves of Pepsin with Special reference to Their Clinical Importance", Gut 6:506-508 (1965).
Plummer, "Jikken de Manabu Seikagaku", 1981. 45-51. [Japanese publication of Plummer "Introduction to Practical Biochemistry"] (Exhibit A18).
Pre-Appeal Brief Request for Review dated Jan. 17, 2017. U.S. Appl. No. 14/879,885.
Preliminary Amendment dated Aug. 5, 2009 in U.S. Appl. No. 12/325,049.
Preliminary Amendment dated Dec. 11, 2007 in U.S. Appl. No. 11/917,188.
Preliminary Amendment dated Mar. 12, 2013 in U.S. Appl. No. 13/797,622.
Preliminary Amendment dated Oct. 18, 2011 in U.S. Appl. No. 13/188,329.
Preliminary Amendment Dated Oct. 25, 2018 in U.S. Appl. No. 16/144,120.
Press Release, "Amgen and Immunomedics Announce Emphasis on Development if AMG 412 (Epratuzumab) as Combination Therapy While Closing Single Agent Trial," PRNewswire—FirstCall (Jan. 23, 2003).
Privigen Label (Oct. 2016).
Pulmozyne® (dronase alfa), Physicians' Desk Reference, PDR 60, Thomson PDR, Montvale, NJ, pp. 1245-1247 (2006).
Quyyumi, A., Does Acute Improvement of Endothelial Dysfunction in Coronary Artery Disease Improve Myocardial Ischemia? A Double-Blind Comparison of Parenteral D- and L-Arginine, Journal of American College of Cardiology, 32(4), pp. 200-208, (1998).
Raibekas, et al., "Anion Binding and Controlled Aggregation of Human Interleukin-1 Receptor Antagonist," Biochemistry 4(29), pp. 9871-9879. 2005.
Raptiva® (efalizumab) Label, 1-34 (2003).
Raptiva® (efalizumab), Physicians' Desk Reference, PDR 59, Thomson PDR, Montvale, NJ, pp. 1350-1354 (2005).
Rau. Adalimumab (a fully human anti-tumour necrosis factor a monoclonal antibody) in the treatment of active rheumatoid arthritis: the initial results of five trials. Ann. Rehum. Dis. 2002; 61 (Suppl.): 1170-1173.
Reddy et al., "Computational Virology: From the inside out", Biochimica et Biophysica Acta, Jul. 2016, vol. 1858, Issue 7, Part B, pp. 1610-1618.

Redeclaration of Interference dated Aug. 4, 2016 in Interference No. 106,057, involving U.S. Appl. No. 13/797,622 and U.S. Appl. No. 13/188,329 and U.S. Pat. No. 8,420,081.
Re-Examination Report dated Mar. 2, 2018 in Australian App. No. 2015242973.
Remicade® Label (Aug. 1998).
Remicade® (inflizimab) Label, 1-23 (2002).
Remicade® (inflizimab), Physicians' Desk Reference, PDR 57, Thomson PDR, Montvale, NJ, pp. 1178-1182 (2003).
Remmele et al., Active Dimer of Epratuzumab Provides Insight into the Complex Nature of a Antibody Aggregate, J Pharmaceutical Sciences, 95:126-145 (2006).
Remmele, R., et al. Inyrtlrukin-1 Receptor (1L-1R) Liquid Formulation Development Using Differential Scanning Calorimetry, Pharmaceutical Research, vol. 2, No. 2, pp. 200-2008, (1998).
Replacement Declaration of Klaus-Peter Radtke, Ph.D. Dated Jan. 31, 2017, in the Patent Trial and Appeal Board, United States Patent and Trademark Office, Petition No. PTAB-IPR2017-00822.
Replacement Declaration of Klaus-Peter Radtke, Ph.D. Dated Jan. 31, 2017, in the Patent Trial and Appeal Board, United States Patent and Trademark Office, Petition No. PTAB-IPR2017-00823.
Replacement Petition for Inter Partes Review of U.S. Pat. No. 9,085,619 Dated Jan. 31, 2017 by Coherus BioSciences Inc, in the Patent Trial and Appeal Board, United States Patent and Trademark Office, Petition No. PTAB-IPR2017-00822.
Replacement Petition for Inter Partes Review of U.S. Pat. No. 9,085,619 Dated Jan. 31, 2017 by Coherus BioSciences Inc, in the Patent Trial and Appeal Board, United States Patent and Trademark Office, Petition No. PTAB-IPR2017-00823.
Report of Re-Examination with English translation dated Nov. 26, 2020 in Japanese Patent Application No. 2017-218002 in 5 pages.
Request for Correction filed in the Demand for Invalidation Trial against Japanese Patent No. 5856555 in 29 pages, dated Nov. 22, 2021.
Request for Correction with English Translation dated Dec. 10, 2020 filed in the response to the Demand for Invalidation Trial in Japanese Patent No. 6293103.
Request for Correction with English translation filed in the Demand for Invalidation Trial against Japanese Patent No. 6293103 in 29 pages, dated Jan. 31, 2022.
Request for Rectification under Rule 91 dated Sep. 7, 2016 in International Application PCT/US2006/0022599.
Request for Withdrawal with English translation filed in the Demand for Invalidation Trial against Japanese Patent No. 5856555 in 5 pages, dated Feb. 10, 2022.
Request for Withdrawal with English translation filed in the Demand for Invalidation Trial against Japanese Patent No. 6293103 in 5 pages, dated Feb. 10, 2022.
Response dated Jul. 12, 2019 to European Office Action of Mar. 5, 2019 for European Patent Application No. EP 17 205 734.1.
Response to Demand for Invalidation Trial against Japanese Patent No. 5856555, filed Oct. 1, 2020 (with machine translation).
Response to European Patent Office Action, filed Oct. 28, 2016 in European App. No. 06772779.2.
Response to Final Office Action dated Aug. 18, 2017 in U.S. Appl. No. 15/231,490.
Response to Final Office Action dated Aug. 18, 2017 in U.S. Appl. No. 15/232,733.
Response to Final Office Action dated Sep. 13, 2017 in U.S. Appl. No. 15/232,733.
Response to Final Office Action dated Sep. 6, 2017 in U.S. Appl. No. 15/227,880.
Response to Meeting Request Dated Aug. 5, 2016 From FDA to Amgen.
Response to Non-Final Office Action dated Apr. 21, 2017. U.S. Appl. No. 14/879,847.
Response to Non-Final Office Action dated Aug. 18, 2017 in U.S. Appl. No. 15/230,039.
Response to Non-Final Office Action dated Jun. 14, 2017 in in U.S. Appl. No. 15/228,955.
Response to Non-Final Office Action dated May 24, 2017 in U.S. Appl. No. 15/232,733.

(56) References Cited

OTHER PUBLICATIONS

Response to Non-Final Office Action dated May 24, 2017 in U.S. Appl. No. 15/255,018.
Response to Non-Final Office Action dated May 8, 2017 in U.S. Appl. No. 15/227,880.
Response to Non-Final Office Action dated May 8, 2017 in U.S. Appl. No. 15/230,039.
Response to Non-Final Office Action dated May 8, 2017 in U.S. Appl. No. 15/231,490.
Response to Non-Final Office Action dated May 8, 2018 in in U.S. Appl. No. 15/228,955.
Response to Non-Final Office Action dated Nov. 13, 2017 in in U.S. Appl. No. 15/228,955.
Response to Non-Final Office Action dated Oct. 20, 2017 in U.S. Appl. No. 15/227,880.
Response to Non-Final Rejection dated Jun. 2, 2011 in U.S. Appl. No. 12/325,049.
Response to Non-Final Rejection dated May 21, 2012 in U.S. Appl. No. 12/325,049.
Response to Notice of Reasons for Invalidation with English translation filed in the Demand for Invalidation Trial against Japanese Patent No. 6293103 in 29 pages, dated Jan. 31, 2022.
Response to Office Action Dated Apr. 21, 2014 in U.S. Appl. No. 13/401,496.
Response to Office Action Dated Aug. 17, 2011 in U.S. Appl. No. 12/632,690.
Response to Office Action dated Aug. 24, 2017 in U.S. Appl. No. 15/227,880.
Response to Office Action Dated Feb. 7, 2007 in U.S. Appl. No. 10/376,576.
Response to Office Action Dated Jul. 24, 2009 in U.S. Appl. No. 11/784,538.
Response to Office Action Dated Jun. 28, 2016 in U.S. Appl. No. 14/478,926.
Response to Office Action dated Mar. 30, 2018 in U.S. Appl. No. 15/698,405.
Response to Office Action Dated May 17, 2006 in U.S. Appl. No. 10/376,576.
Response to Office Action Dated Oct. 26, 2018 in U.S. Appl. No. 15/958,261.
Response to Restriction Requirement and Amendment dated Jan. 10, 2011 in U.S. Appl. No. 11/917,188.
Response to Restriction Requirement Dated Jul. 8, 2008 in U.S. Appl. No. 11/784,538.
Response to Restriction Requirement Dated Dec. 16, 2010 in U.S. Appl. No. 12/325,049.
Response to Restriction Requirement Dated Feb. 2, 2009 in U.S. Appl. No. 11/784,538.
Response to Restriction Requirement dated Mar. 23, 2018 in U.S. Appl. No. 15/227,880.
Response to Restriction Requirement Dated Nov. 7, 2017 in U.S. Appl. No. 15/341,962.
Response to Restriction Requirement dated Oct. 29, 2014 in U.S. Appl. No. 13/797,622.
Response to Restriction Requirement dated Oct. 29, 2014 in U.S. Appl. No. 13/797,690.
Response to Restriction Requirement Dated Sep. 26, 2013 in U.S. Appl. No. 13/401,496.
Response to Restriction Requirement Dated Sep. 27, 2005 in U.S. Appl. No. 10/376,576.
Response to Restriction Requirement dated Sep. 29, 2014 in U.S. Appl. No. 13/188,329.
Restriction Requirement Dated Dec. 9, 2010 in U.S. Appl. No. 11/917,188.
Restriction Requirement Dated Feb. 7, 2008 in U.S. Appl. No. 11/784,538.
Restriction Requirement Dated Jun. 26, 2013 in U.S. Appl. No. 13/401,496.
Restriction Requirement Dated Jun. 9, 2017 in U.S. Appl. No. 15/341,962.
Restriction Requirement Dated Mar. 27, 2018 in U.S. Appl. No. 15/214,377.
Restriction Requirement Dated May 27, 2005 in U.S. Appl. No. 10/376,576.
Restriction Requirement Dated Nov. 27, 2017 in U.S. Appl. No. 15/227,880.
Restriction Requirement Dated Oct. 18, 2010 in U.S. Appl. No. 12/325,049.
Restriction Requirement Dated Oct. 2, 2008 in U.S. Appl. No. 11/784,538.
Restriction Requirement Dated Sep. 5, 2014 in U.S. Appl. No. 13/797,622.
Ries-Kautt, M. et al., "Relative Effectiveness of Various Ions on the Solubility and Crystal Growth of Lysozyme", The Journal of Biological Chemistry, vol. 264, No. 2, Jan. 1989, pp. 745-748.
Risihi V, et al. Role of Non-Compatible Osmolytes in the Stabilization of Proteins During Heat Stress, Biochemical Journal, vol. 329, pp. 137-143, (1998).
Robbins D, et al., Antibodies of Covalent Aggregates of Insulin in Blood of Insulin-Using Diabetic Patients, Diabetes, vol. 36, pp. 838-845, (1987).
Rouet, et al., "Stability Engineering of the Human Antibody Repertoire," FEBS Letters 588, pp. 269-277, 2014.
Rousseaux et al., "Optimal Conditions for the Preparation of Fab and F(ab') Fragments of Monoclonal IgG of Different Rat IgG Subclasses", J. Immunol Methods 64:141-146 (1983).
Ruiz, et al., "Aggregation of Recombinant Human Interferon Alpha 2b in Solution: Technical Note," AAPS Pharm. Sci. Tech. 7(4), Article 99, pp. E1-E5. 2006.
Salinas, et al., "Understanding and Modulating Opalescence and Viscosity in a Monoclonal Antibody Formulation," J. Pharm. Sci. 99(1), pp. 82-93. 2010.
Saluja et al. Application of High-Frequency Rheology Measurements for Analyzing Protein-Protein Interactions in High Protein Concentration Solutions Using a Model Monoclonal Antibody (IgG2). J. Pharmaceutical Sci. Sep. 2006, Version of Record Online Jul. 17, 2006 95: pp. 1967-1983.
Saluja et al., "Ultrasonic Storage Modulus as a Novel Parameter for Analyzing Protein-Protein Interactions in High Protein Concentration Solutions: Correlation with Static and Dynamic Light Scattering Measurements," Biophysical Journal, Jan. 2007, 92: pp. 234-244.
Saluja et al., Ultrasonic Rheology of a Monoclonal Antibody (IgG2) Solution: Implications for Physical Stability of Proteins in High Concentration Formulations. J. Pharmaceutical Sci. 96: Dec. 2007. pp. 3181-3195.
Saluja, "Characterization of Protein-Protein Interactions for Optimizing Formulation and Physical Stability of High Protein Concentration Solutions" Dissertation, University of Connecticut, Jan. 2007.
Saluja, et al., Nature and consequences of protein-protein interactions in high protein concentration soultions. Intl. J. Pharmaceutics, 2008, 358: 1-15.
Sandoz Inc.'s Answer, Affirmative Defenses and Demand for Jury Trial in *Immunex Corporation v. Sandoz Inc.*, Filed Mar. 21, 2016 in United States District Court for The District of New Jersey , C.A. No. 2:16-cv-01118-CCC-MF , 54 Pages (Document 31).
Santa Cruz Biotechnology, Inc., Product Sheets for IGF-IRα (1H7): sc-461, IGF-IR (3B7): sc-462, and IGF-IRα (2C8): sc-463, in 3 pages (Available at https://www. scbt.com/p/igf-iralpha-antibody-1h7, https://www.scbt.com/p/igf-ir-antibody-3b7, and https://www.scbt.com/p/igf-iralpha-antibody-2c8, respectively [retrieved on Mar. 12, 2021]). No publication date is apparent in these Product Sheets.
Sasaki et al, "ELISA Diagnosis for Mycoplasma pneumoniae Infection with Human Normal Immunoglobulin Products as Control Sera", The Journal of the Japanese Association for Infectious Diseases, Apr. 1990, vol. 64, No. 4, filed as Exhibit A29 in the Demand for Invalidation Trial against Japanese Patent No. 6293103, in 6 pages (with partial English translation).
Scheffler et al., Improving Antibody Characterization by Orbitrap Mass Spectrometry. Thermo Scientific. CASSS Mass Spec 2012, Abstract P-216 and poster. The CASSS Mass Spec conference took place Sep. 11-14, 2012.

(56) References Cited

OTHER PUBLICATIONS

Schwartz "Diafiltration: A Fast, Efficient Method for Desalting, or Buffer Exchange of Biological Samples" 2003 (Exhibit A20).
Schwartz, Diafiltration for Desalting of Buffer Exchange, BioProcess Int'l, May 2003.
Schwartz, Diafiltration: A Fast, Efficient Method for Desalting or Buffer Exchange of Biological Samples. Pall Life Sciences Brochure, Copyright Date 2003.
Schwartzman & Morgan, "Does Route of Administration Affect the Outcome of TNF Antagonist Therapy?," Arthritis Research & Therapy, 6(Suppl. 2):S19-S23 (2004).
Search Report dated May 11, 2020 in European Application No. 19217355.7.
Segel, Biochemical calculations, 2nd ed., New York: John Wiley and Sons, Inc., pp. 1-93 (1976).
Sek, D. Breaking old habits: Moving away from commonly used buffers in pharmaceuticals. Eur. Pharm. Rev. (accessed Oct. 5, 2020) dated Jul. 10, 2012.
Sellers et al., "Dry Powders of Stable Protein Formulations from Aqueous Solutions Prepared Using Supercritical CO2-Assisted Aerosolization", J. Pharm. Sci. 90:785-797 (2001).
Senior Party Gokarn List of Proposed Motions dated Jul. 27, 2016 in Interference No. 106,057, in 76 pages.
Shao and Zydney, "Optimization of Ultrafiltration/Diafiltration Processes for Partially Bound Impurities," Biotech. Bioeng. 87:286-292 (2004).
Sharma et al., Hyperchloremic Acidosis. [Updated May 23, 2020]. In: StatPearls [Internet]. Treasure Island (FL): StatPearls Publishing; Jan. 2020—Available from: https://www.ncbi.nlm.nih.gov/books/NBK482340/ (retrieved Oct. 5, 2020).
Shinmura, I. (Ed.) Kojien, 5th edition. Nov. 11, 1998. 1126, 1192, 1339 (Exhibit A21).
Shinmura, I. (Ed.), Kojien, 5th edition. Nov. 11, 1998. 1126, 1139 (Exhibit A21).
Shire, "Formulation of Proteins and Monoclonal Antibodies (mAbs)," Monoclonal Antibodies, Meeting the Challenges In Manufacturing, Formulation, Delivery and Stability of Final Drug Product, Woodhead Publishing Series in Biomedicine 77, Chap, 4, pp. 93-120. Woodland Publishing, Cambridge, UK. 2015.
Shire, et al., "Challenges in the Development of High Protein Concentration Formulations" J. Pharmaceutical Sciences 2004, 93: pp. 1390-1402.
Slides for Oral Proceedings by Demandee filed in the Demand for Invalidation Trial against Japanese Patent No. 6293103 in 99 pages, dated Aug. 20, 2021.
Soejima, K., et al., An Efficient Refolding Method for the Preparation of Combinant Human Prethombin-2 and Characterization of the Recombinant Derived a-Thrombin, J. Biochem, vol. 130, pp. 269-277, (2001).
Song, Y. et al., "Effect of 'pH' on the rate of asparagine deamidation in polymeric formulations: 'pH'—rate profile", J. Pharm Sci., Feb. 2001, vol. 90(2), pp. 141-156.
Spectrum Laboratories (http://www.spectrumlabs.com/lit/hfdial.pdf, Diafiltration (Buffer Exchange) Using Hollow Fiber Membranes instead of Dialysis Tubing—Automated Diafiltration, date unknown, pp. 1-6).
Statement Brief by Demandee filed in the Demand for Invalidation Trial against Japanese Patent No. 6293103 in 344 pages, dated Aug. 6, 2021.
Statement Brief by the Demandant filed in the Demand for Invalidation Trial against Japanese Patent No. 6293103 in 177 pages, dated Aug. 6, 2021.
Statement Brief for the Oral Proceedings by Demandant filed in the Demand for Invalidation Trial against Japanese Patent No. 5856555, dated May 6, 2021, in 467 pages.
Statement Brief for the Oral Proceedings filed in the Demand for Invalidation Trial against Japanese Patent No. 5856555, dated Apr. 8, 2021, in 140 pages.
Statement of Grounds and Particulars by AbbVie, Inc. in Opposition to Australian App. No. 2015242973.

Stoner et al., "Protein-Solute Interactions Affect the Outcome of Ultrafiltration/Diafiltration Operations," J. Pharm. Sci., 93:2332-2342 (2004).
Substance Name: Epratuzumab [USAN:INN] ChemIDplus, A Toxnet Database, U.S. National Library of Medicine., downloaded from the world wide web at https://chem.nlm.nih.gov/chemidplus/name/startswith/epratuzumab on Jan. 30, 2017. It is noted that this item refers to a webpage and may have been available in some form at an earlier point in time.
Substitute First Declaration of Andrew Zydney, Ph.D., dated Oct. 28, 2016.
Substitute Specification Submitted with Amendment and Reply to Notice File Corrected Application Papers Dated Jun. 24, 2013 in U.S. Appl. No. 13/797,622.
Substituted Claims dated Sep. 7, 2006 from File History of Application No. PCT/US2006/022599.
Summons to Attend Oral Proceedings Pursuant to Rule 115(1) EPC in European Application No. 06772779.2 dated Apr. 10, 2017.
Supplemental Response dated Aug. 9, 2011 in U.S. Appl. No. 12/325,049.
Supplementary European Search Report Mailed Jan. 23, 2006 in European Patent Application No. 03716244.
Synagis Label (Jul. 2004).
Tayyab et al., "Size Exclusion of Chromatography and Size Exclusion HPLC of Proteins", Biochemical Education, 19:149-152 (1991).
Third Redeclaration dated Dec. 11, 2017 in Interference No. 106,057, involving U.S. Appl. No. 13/797,622 and U.S. Appl. No. 13/188,329 and U.S. Pat. No. 8,420,081.
Thomson Reuters, "A Bioworld Special Report: Biosimilars: U.S. Market Opportunities and Critical Strategies 2016" (2016).
Thurlkill et al., "pK values of the ionizable groups of proteins" Protein Science 2006, 15: pp. 1214-1218.
Trial Decision received from the Intellectual Property Trial and Appeal Board (IPTAB) for Korean Application No. 10-2019-7014130 with English Translation in 41 pages, dated May 20, 2022.
Tsai et al., "Origin of the Isoelectric Heterogeneity of Monoclonal Immunoglobulin h1B4", Pharmaceutical Research, 1993, vol. 10, No. 11, pp. 1580-1586.
Tsourounis, Biologic Therapies for the Treatment of Chronic Plaque Psoriasis, Formulary 40:184-199 (Jun. 2005).
Tysabri Label (Nov. 2004).
U.S. Pharmacopeia, "Water for Pharmaceutical Purposes," USP 24, United Stated Pharmacopeial Convention, Inc., Rockville, MD, pp. 2154-2163 (2000).
U.S. Prosecution History of U.S. Appl. No. 13/774,735 (U.S. Pat. No. 8,883,146).
U.S. Prosecution History of U.S. Appl. No. 14/506,576 (U.S. Pat. No. 9,085,619).
U.S. Prosecution History of U.S. Appl. No. 61/004,992.
Van de Putte et al. "Efficacy and safety of the fully human anti-tumour necrosis factor alpha monoclonal antibody adalimumab (D2E7) in DMARD refractory patients with rheumatoid arthritis: a 12 week, phase II study," Ann Rheum Dis 2003;62:1168-1177, dated 2003.
Van de Putte, et al., A Single Dose Placebo Controlled Phase I Study of the Fully Human Anti-TNF Antibody D2E7 in Patients with Rheumatoid Arthritis, Arthritis Rheum., 41(9), S57 (Sep. 1998).
Van Reis and Zydney, "Protein Ultrafiltration," in Encyclopedia of Bioprocess Technology: Fermentation, Biocatalysis, and Bioseparation, ed. by M.C. Flickinger and S.W. Drew, pp. 2197-2214, John Wiley & Sons, Inc., New York (1999).
Van Reis and Zydney, "Protein Ultrafiltration," in Encyclopedia of Industrial Biotechnology: Bioprocess, Bioseparation, and Cell Technology, ed. by Flickinger and Drew, John Wiley & Sons, Inc. (2010).
Van Reis and Zydney,"Bioprocess Membrane Technology", J. Membrane Sci. 297:16-50 (2007).
Van Slyke, "On the Measurement of Buffer Values and on the Relationship of Buffer Value to the Dissociation Constant of the Buffer and the Concentration and Reaction of the Buffer Solution" Constant J. Biol. Chem. 52:525-570 (1922).
Vectibix Label (Sep. 2006).

(56) References Cited

OTHER PUBLICATIONS

Vermeer and Norde, "The Thermal Stability and Activity Curves of Pepsin with Special reference to Their Clinical Importance", Biophys. J. 78:394-404 (2000).
Vermeer et al., "The Thermal Stability of Immunoglobulin: Unfolding and Aggregation of a Multi-Domain Protein", Biophys. J. 78:394-404 (2000).
Veys et al., "Pain at the injection site of subcutaneously administered erythropoietin: phosphate-buffered epoetin alpha compared to citrate-buffered epoetin alpha and epoetin beta," Clinical Nephrology, 1998, 49:41-44.
Vidanovic et al., "Effects of nonionic surfactants on the physical stability of immunoglobulin G in aqueous solution during mechanical agitation", Pharmazie, vol. 58, pp. 399-404, 2003.
Vivaglobin Label (Jan. 2006).
Vollmers et al., "A rapid method for purification of monoclonal human IgM from mass culture," Hum. Antibod. Hybridomas, 7(1):37-41 (1996).
Wang and Goodman, Basic & Clinical Immunology, ed. Fudenberg, Stites, Caldwell and Wells, Los Altos, CA: Lange Medical Publication, pp. 15-40 (1976).
Wang et al., "Antibody structure, instability, and formulation", J. Pharm. Sci. 96(1):1-26 (2007).
Wang et al., "Instability, stabilization, and formulation of liquid protein pharmaceuticals", Int'l J. Pharmaceutics, vol. 185, pp. 129-188 (1999).
Wang et al., "Opalescence of an IgG1 Monoclonal Antibody Formulation is Mediated by Ionic Strength and Excipients", BioPharm International, pp. 36-47, Apr. 2009.
Wang, Y, et al. Parenteral Formations of Proteins and Peptides: Stability and Stabilizers, Journal of Parenteral Sciences & Technology, 42(2S), pp. S04-S26, (1988).
Weinblatt et al., Adalimumab, a Fully Human Anti-Tumor Necrosis Factor a Monoclonal Antibody for the Treatment of Rheumatoid Arthritis in Patients Taking Concomitant Methotrexate. Arthritis & Rheumatism, 49: 35-45, 2003.
Weltman et al., "Hydrogen Ion Titration of Rabbit Gamma-Globulin and Some of Its Subunits" Biochim Biophys Acta. Dec. 9, 1964;93:553-63 (Exhibit A5).
Williams. J.M. et al. Benzyl alcohol attenuates the pain of lidocaine injections and prolongs anesthesia., J. Dermatol Surg Oncol., vol. 20, No., 11, pp. 730-733, (1994).
Wolberg et al., Coagulation factor XI is a contaminant in intravenous immunoglobulin preparations. Am J Hematol. Sep. 2000;65(1):30-4.
Written Answer To The Case with English Translation dated Dec. 10, 2020 filed in the response to the Demand for Invalidation Trial in Japanese Patent No. 6293103.
Written Argument filed in the Demand for Invalidation Trial against Japanese Patent No. 5856555 in 73 pages, dated Nov. 22, 2021.
Xolair® (Omalizumab) Label, 1-17 (2003).
Xolair label, revised 2018 (initial approval 2003) (available at https://www.accessdata.fda.gov/drugsatfda_docs/label/2018/103976352311bl.pdf).
XOLAIR® (Omalizumab), Physicians' Desk Reference, PDR 58, Thomson PDR, Montvale, NJ, pp. 1374-1376 (2004).
Yancey, P., et al. Living with Water Stress: Evolution of Osmolyte Systems, Science, vol. 217, pp. 1214-1222, (1982).
Yang, et al., "Development of ABX-EGF, a Fully Human Anti-EGF Receptor Monoclonal Antibody, for Cancer Therapy,", Crit. Rev. Oncol. Hematol. 38: 17-23 (2001).
Yoshimoto, H. et al., "Overexpression of Insulin-Like Growth Factor-1 (IGF-I) Receptor and the Invasiveness of Cultured Keloid Fibroblasts", American Journal of Pathology, vol. 154, No. 3, Mar. 1999, pp. 883-889.
Yoshimura et al. Diafiltration studies of protein solutions using IgG formulations: Test Report. Dated May 12, 2020. (Exhibit A24).
Yu et al., "Pain Perception Following Subcutaneous Injections of Citrate-Buffered and Phosphate-Buffered Epoetin Alpha," Int'l J. Artificial Organd 21(6), pp. 341-343, 1998.
Zeman and Zydney, "Microfiltration and Ultrafiltration: Principles and Applications", pp. 380-396; 544-564, Marcel Dekker, Inc., New York (1996).
Zevalin® Label, Physicians' Desk Reference. Thomas PDR, Montvale, N.J., 60th ed. 2006.
Zevalin label, revised 2009 (initial approval 2002) (available at https://www.accessdata.fda.gov/drugsatfda_docs/label/2009/125019s0156.pdf).
Zhao et al., "Recent U.S. Patents on Protein Drug Formulation: 2000-2007", Recent Patents on Drug Delivery & Formulation, vol. 2, pp. 200-208, 2008.
Zydney and Kuriyel, "Protein Concentration and Buffer Exchange," in Methods in Biotechnology, vol. 9, Downstream Protein Processing, ed. by M. Desai, pp. 23-34, Humana Press, Totowa, NJ (2000).
Zydney, "5.2 Ultrafiltration / Diafiltration", Slideshow Presentation at Novo Nordisk and Aventis Pasteur (2004).
Zydney, "Membrane Separations: Membrane Bioseparations," in Encyclopedia of Separation Science, pp. 1748-1755, Academic Press, Ltd., London (2000).
Office Action for Brazilian Application No. BR 11 2019 007858-4 with English translation in 9 pages, dated Aug. 29, 2024.
Office Action for Brazilian Application No. BR 12 2021 025863-5 with English translation in 16 pages, dated Aug. 30, 2024.
Office Action for Japanese Application No. JP 2023-180119 with English translation in 7 pages, dated Nov. 26, 2024.

Figure 1: Percent HMW (peak B) as detected by SEC
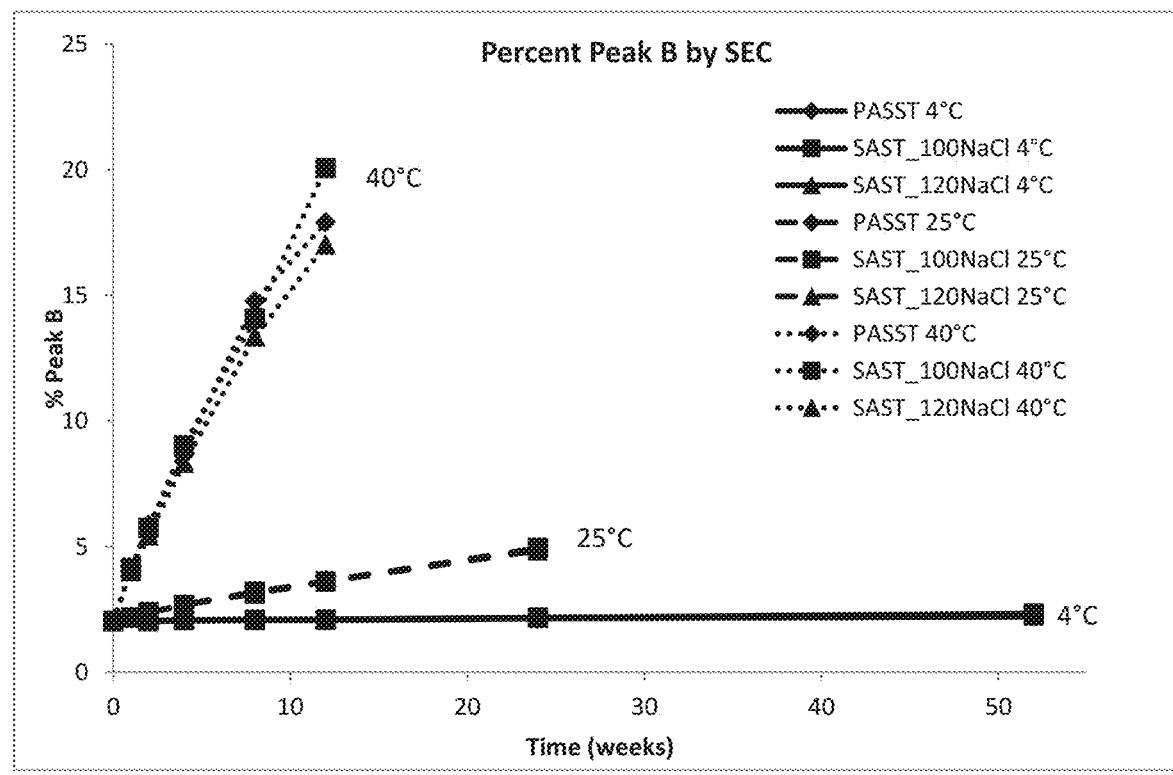

Figure 2: Percent LMW as detected by dSEC
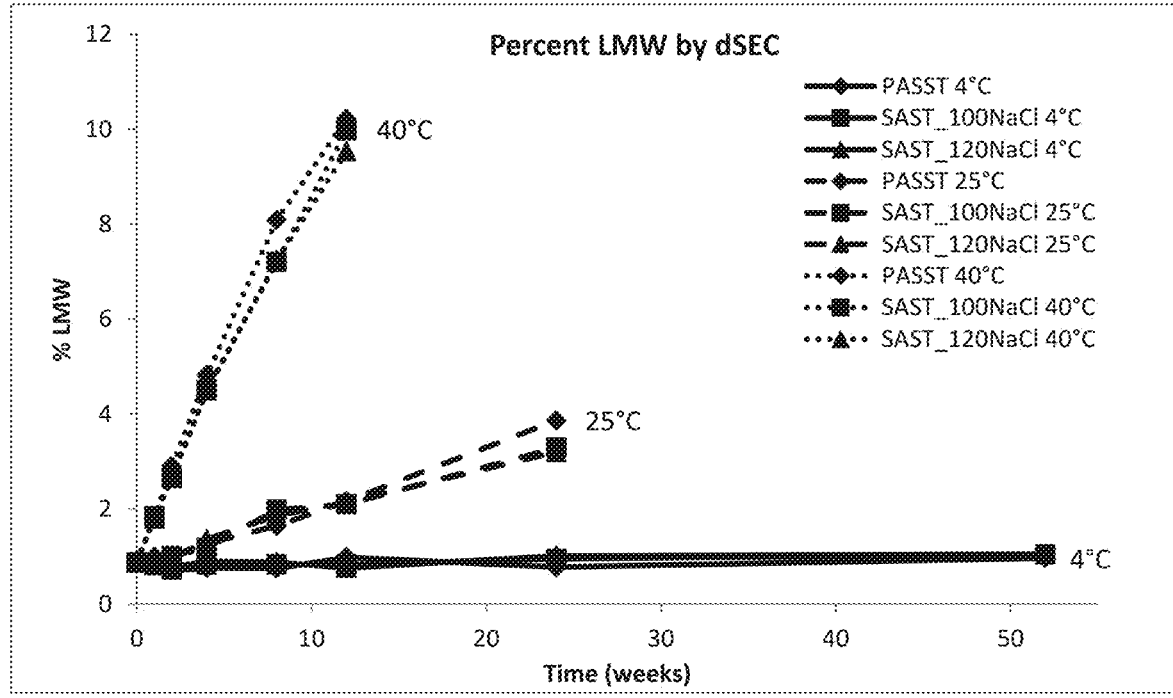
Figure 3: Percent Peak 3 as detected by HIC
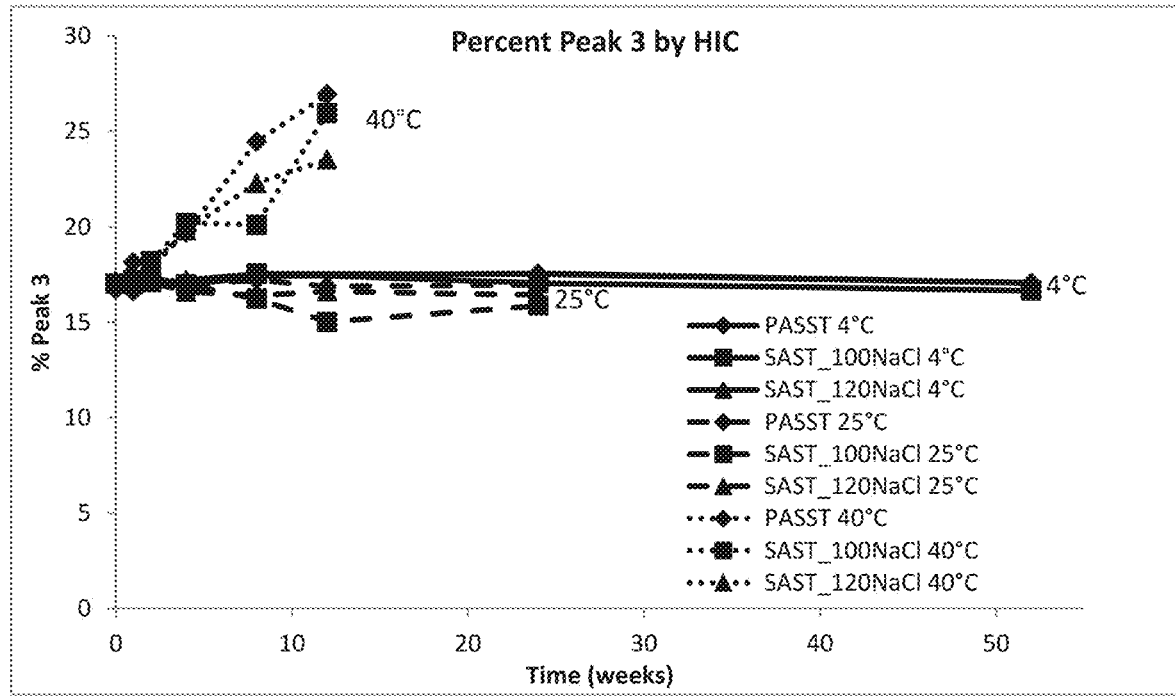

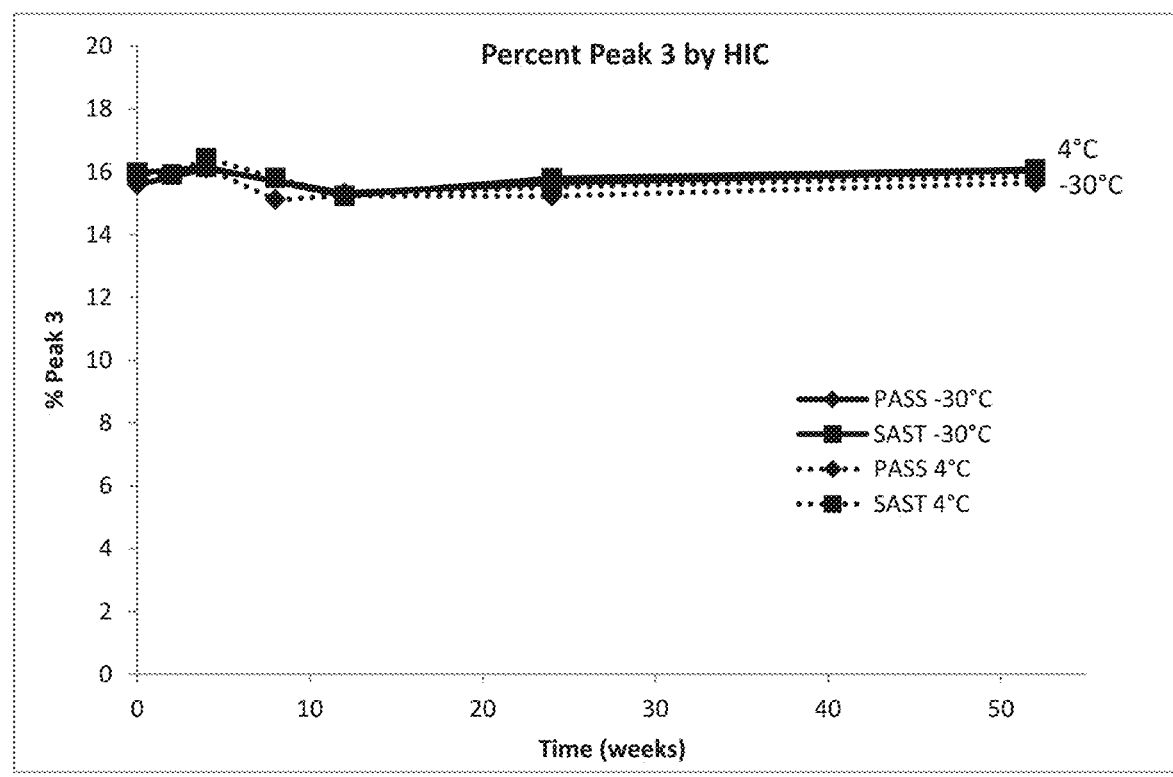
Figure 4: Stainless Steel Cryo Vessel storage- Percent Peak 3 by HIC

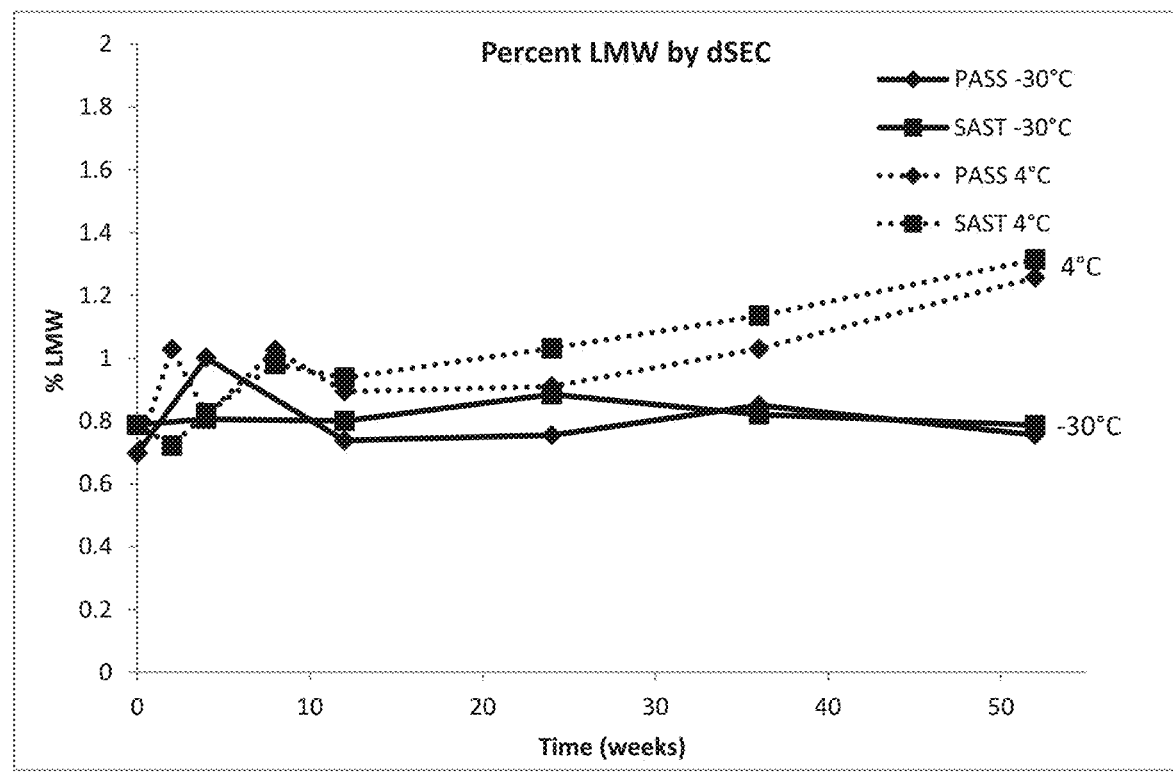
Figure 5: Stainless Steel Cryo Vessel storage- Percent LMW by dSEC

Figure 6: Stainless Steel Cryo Vessel storage- Percent Peak B by SEC
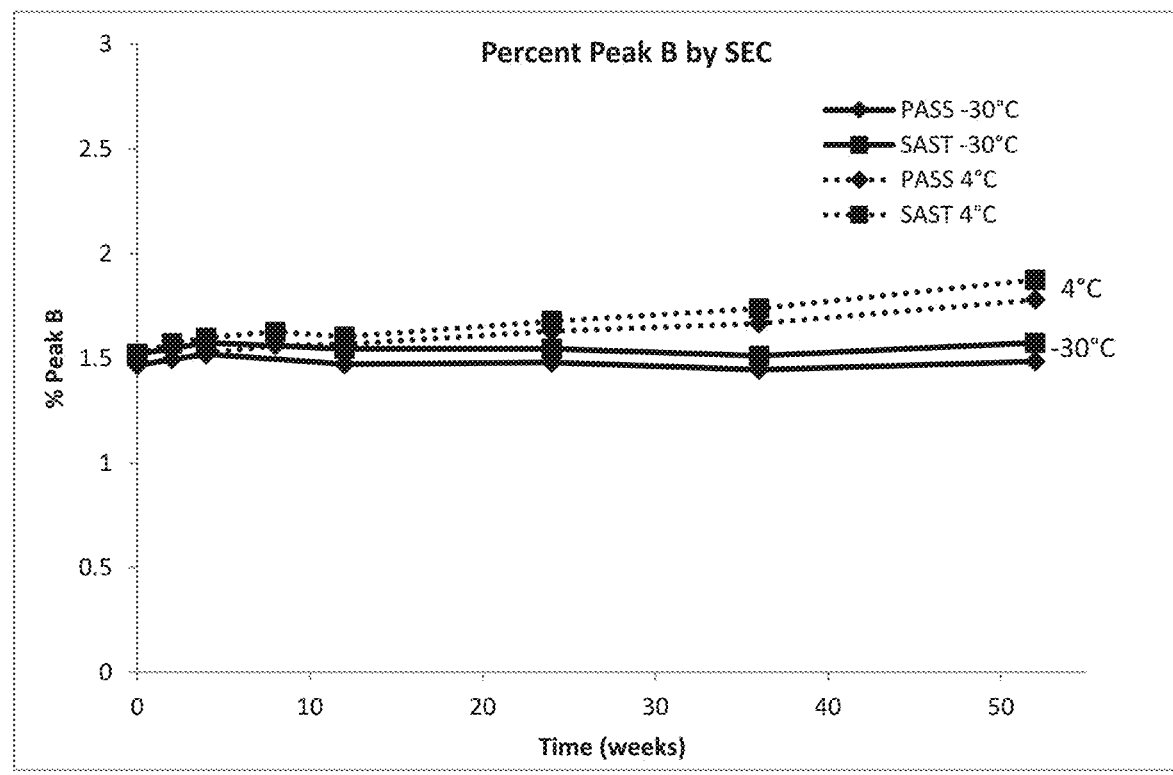

Figure 7: Freeze Thaw Stability
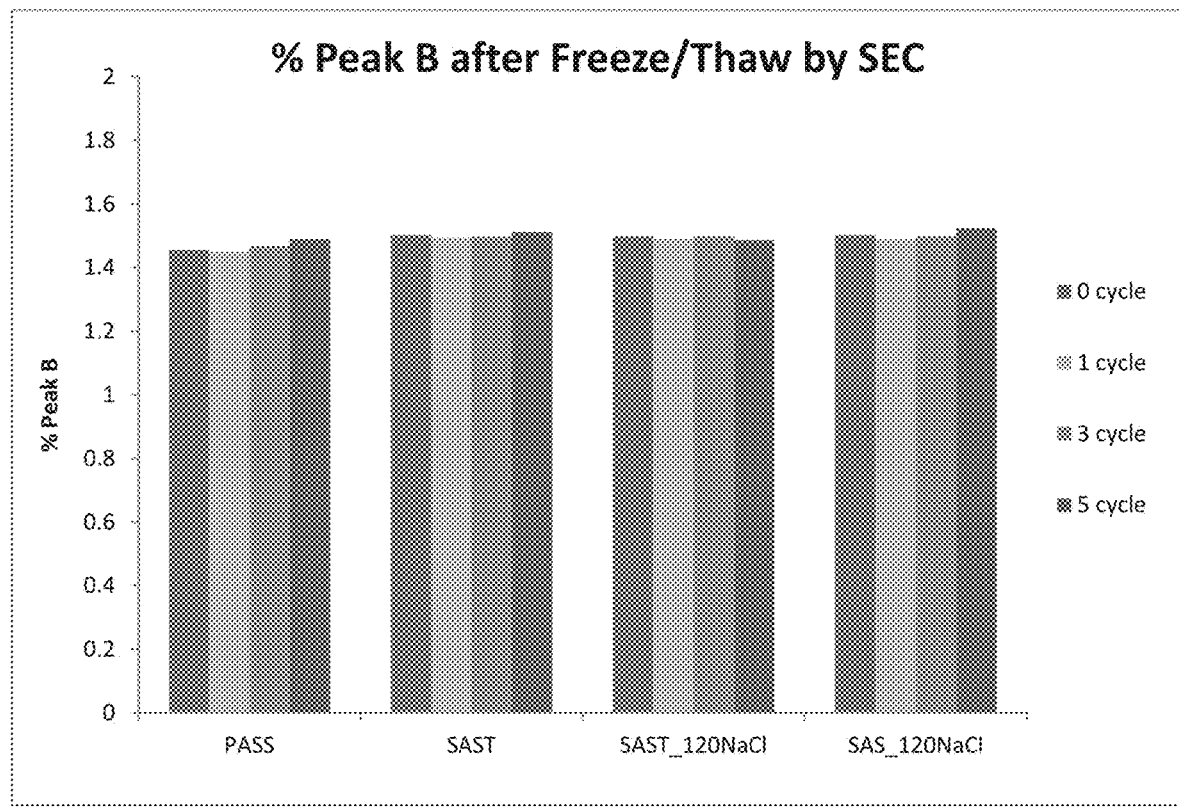

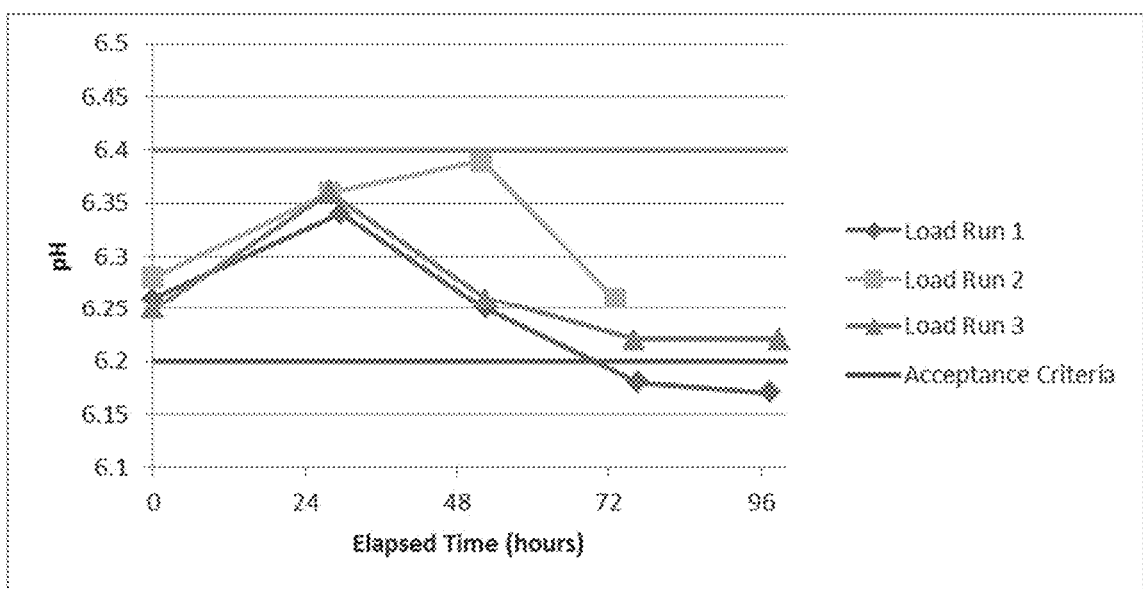
Figure 8: Conditioned VF Pool Stability at CRT

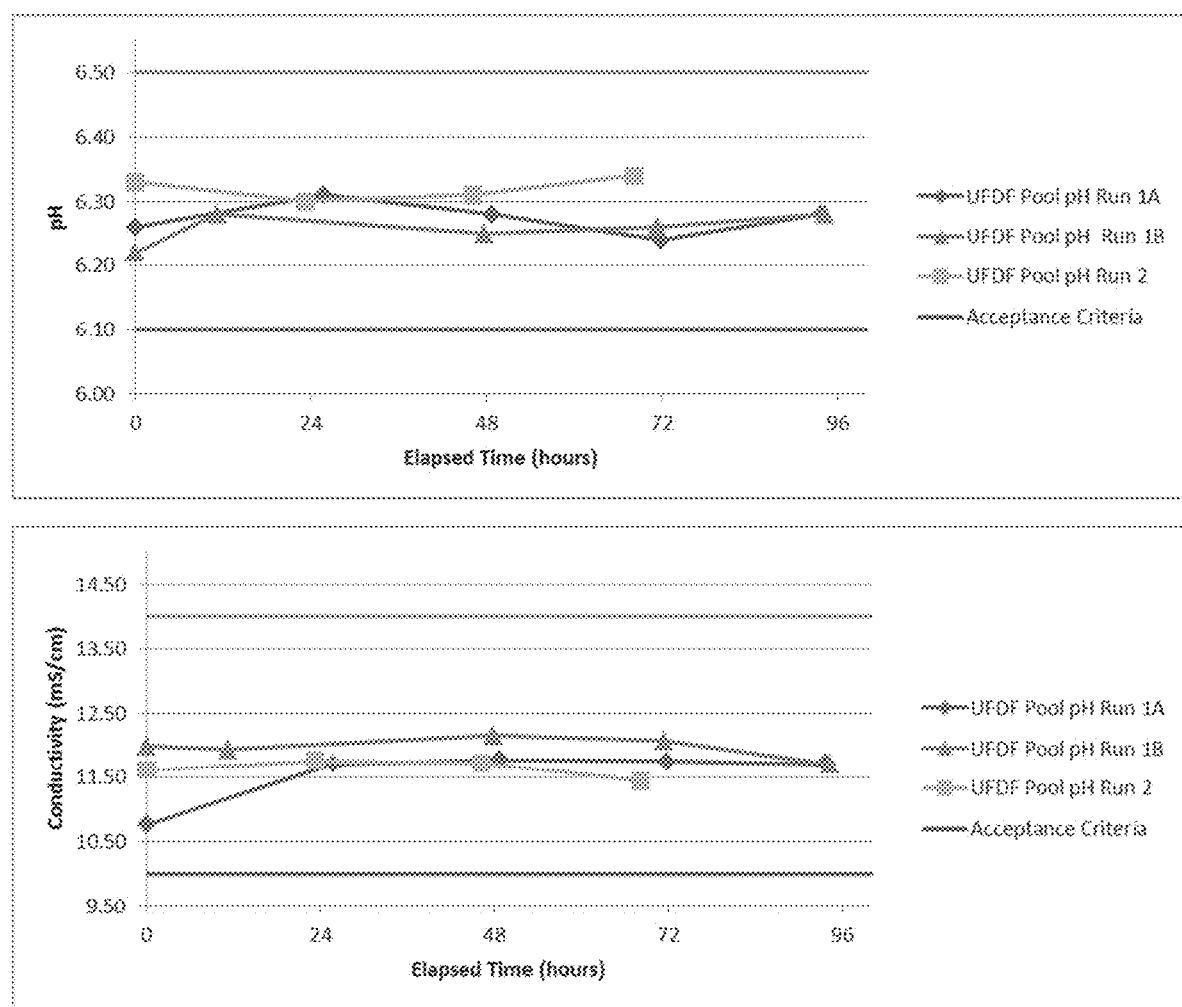
Figure 9: UF/DF Pool Stability pH and Conductivity at CRT

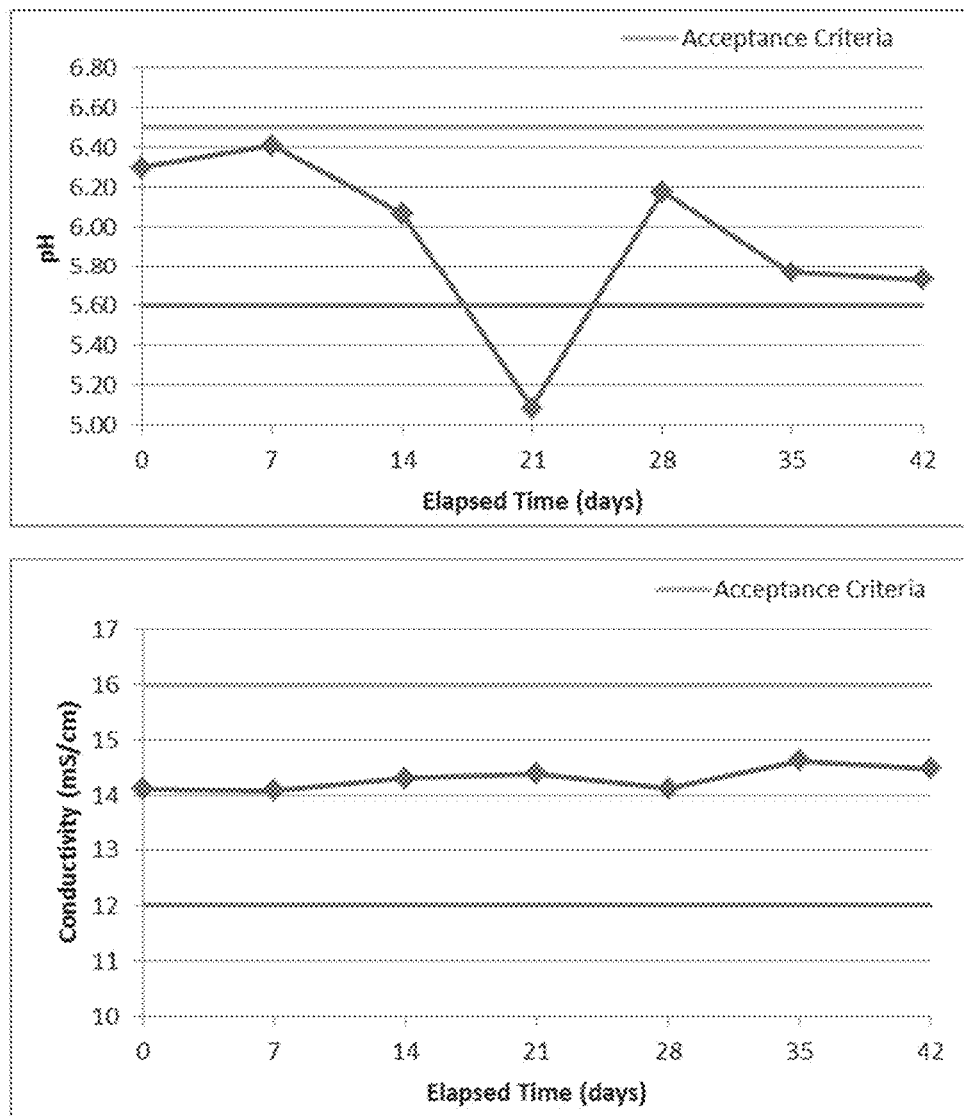

METHODS OF TREATMENT OF ARTHRITIS AND/OR PSORIASIS WITH PHARMACEUTICAL FORMULATIONS OF ETANERCEPT

CROSS-REFERENCE TO RELATED APPLICATION

This application is a divisional of patent application Ser. No. 16/144,120, filed Sep. 27, 2018, now U.S. Pat. No. 11,491,223, issued Nov. 8, 2022, which is a divisional of patent application Ser. No. 15/958,261, filed Apr. 20, 2018, now U.S. Pat. No. 10,307,483, issued Jun. 4, 2019, which is a continuation of patent application Ser. No. 15/788,762, filed Oct. 19, 2017, now abandoned, which claims the benefit of U.S. Provisional Application No. 62/411,458 filed Oct. 21, 2016, all of which are incorporated in their entireties by reference herein.

SEQUENCE LISTING STATEMENT

The present application is accompanied by a Sequence Listing in electronic format. The Sequence Listing is provided as a "Sequence Listing XML" file entitled AMGN_004D2_SEQLIST.xml, created Sep. 16, 2022, which is 2,710 bytes in size. The information in the electronic format of the Sequence Listing XML is incorporated herein by reference in its entirety.

FIELD OF THE INVENTION

The invention relates to the formulation of pharmaceutical compositions of etanercept. The invention also relates to methods of removing buffer and of formulating pharmaceutical compositions of etanercept.

BACKGROUND OF THE INVENTION

Formulation of a protein drug can present many challenges for the pharmaceutical scientist. A formulation must be found that stabilizes the protein drug and makes it resistant to degradation by proteolysis, aggregation, misfolding, etc. Especially for engineered proteins that differ in substantial respects to known proteins, finding appropriate stability conditions can be challenging. It is also desirable to have the protein drug be in a format that is convenient for the patient. Desired properties include stability at ambient and refrigerated temperatures; suitability for long term storage, appropriate dosing times and volumes; and minimization of discomfort upon administration.

Etanercept is a dimeric fusion protein consisting of the extracellular ligand-binding portion of the human 75 kilodalton (p75) tumor necrosis factor receptor (TNFR) linked to the Fc portion of human IgG1. The Fc component of etanercept contains the CH2 domain, the CH3 domain and hinge region, but not the CH1 domain of IgG1. When expressed in mammalian cells, it forms a homodimeric complex with two domains of the TNF receptor. Thus, it is an artificial protein that is different from both antibodies and soluble TNF receptors, and therefore subject to different degradation pathways than either. Etanercept is commercially available as ENBREL® (Amgen Inc., Thousand Oaks, CA) and is approved to treat moderately to severely active rheumatoid arthritis, moderately to severely active polyarticular juvenile idiopathic arthritis (JIA) in patients ages two and older, chronic moderate to severe plaque psoriasis (PsO) in adults, psoriatic arthritis (PsA) in adults, and active ankylosing spondylitis (AS). Etanercept was first available in a lyophilized formulation to be reconstituted immediately before injection.

Upon reconstitution of the lyophilized product with water for injection, the formulation is 10 mM Tris HCL, 4% mannitol, 1% sucrose, pH 7.4 at about 25 mg/mL. However, this formulation is not stable for storage. It was discovered that a liquid formulation of etanercept could be achieved using arginine to stabilize the protein (see U.S. Pat. No. 7,648,702). An exemplary liquid formulation consists of 50 mg/mL etanercept, 25 mM phosphate buffer, 25 mM L-arginine hydrochloride, 100 mM NaCl, 1% Sucrose at pH 6.3 in water.

SUMMARY OF THE INVENTION

Provided herein are new and improved formulations of etanercept. In particular, the invention provides pharmaceutical compositions containing etanercept that are stable and can be conveniently stored as a liquid at controlled room temperature (CRT) for extended periods of time, even in the absence of an additional buffering agent. In addition, when the pharmaceutical compositions of the invention are injected into subjects, they also demonstrate significantly reduced injection pain as compared to the commercially available prior art formulation. Thus these pharmaceutical compositions are more convenient and advantageous for patients.

Another aspect of the invention provides methods of formulating pharmaceutical preparations of etanercept at a desired pH but in the absence of additional buffering agent in the final formulation.

In another aspect, the invention provides a pharmaceutical composition comprising etanercept, NaCl, arginine, and sucrose, wherein the pharmaceutical composition has essentially no additional buffering agent, and the pH of the composition is between 6.1 and 6.5. In one embodiment, the pharmaceutical composition is capable of maintaining the pH between 6.1 and 6.5 when stored at controlled room temperature (CRT) for 2 weeks. In another embodiment, the etanercept concentration is between 40 mg/mL and 100 mg/mL. In another embodiment, the pharmaceutical composition is isotonic. In another embodiment, the pharmaceutical composition contains: between 20 mM and 150 mM NaCl; between 5 mM and 100 mM arginine; and between 0.5% and 2% (w/v) sucrose. In another embodiment, the pharmaceutical composition comprises a surfactant. In another embodiment, the surfactant is polysorbate 20, polysorbate 80, or poloxamer 188. In another embodiment, the surfactant is polysorbate 20 at a concentration (w/v) of between 0.001% and 0.1%. In another embodiment, the surfactant is polysorbate 80 at a concentration (w/v) of between 0.001% and 0.1%. In another embodiment, the surfactant is poloxamer 188 at a concentration (w/v) of between 0.01% to 0.3%. In another embodiment, the pharmaceutical composition maintains a pH of between 5.8 and 6.7 for at least two weeks when stored at approximately 25° C., and wherein less than 6% of the total etanercept is aggregated in a high molecular weight form as assessed using size exclusion chromatography. In another embodiment, the pharmaceutical composition maintains a pH of between about 6.1 and about 6.5. In another embodiment, less than 28% of the total amount of etanercept is in a misfolded form as assessed using hydrophobic interaction chromatography. In another embodiment, the pharmaceutical composition consists essentially of about 40-100 mg/mL etanercept, about 120 mM NaCl, about 25 mM arginine, about 1% sucrose, and water. In another embodiment, the pharmaceutical composition consists essentially of about 40-100 mg/mL etanercept, about 120 mM NaCl, about 25 mM arginine, about 1% sucrose, about 0.01% polysorbate 20, and water.

In another aspect, the present invention provides a method of formulating a pharmaceutical composition of etanercept to remove an additional buffering agent and maintain pH from 6.1 to 6.5, comprising formulating the etanercept formulation in a formulation comprising an additional buffering agent at between pH 6.1 and 6.5, and exchanging the formulation comprising an additional buffering agent against a formulation that does not comprise an additional buffering agent and is between pH 5.6 and 6.5, and collecting the resulting pharmaceutical formulation. In one embodiment, the exchange step uses diafiltration. In another embodiment, the formulation that does not comprise an additional buffering agent is isotonic. In another embodiment, the formulation that does not comprise an additional buffering agent contains sucrose, arginine, and NaCl. In another embodiment, the formulation that does not comprise an additional buffering agent contains between 20 mM and 150 mM NaCl; between 5 mM and 100 mM arginine; and between 0.5% and 2% (w/v) sucrose. In another embodiment, the formulation that does not comprise an additional buffering agent consists essentially of about 120 mM NaCl, about 25 mM arginine, about 1% sucrose, and water. In another embodiment, the method of formulating a pharmaceutical composition of etanercept further comprises adding polysorbate. In another embodiment, the polysorbate is polysorbate 20 at a concentration (w/v) of between 0.001% and 0.1%. In another embodiment, the method of formulating a pharmaceutical composition of etanercept further comprises filtering the pharmaceutical composition. In another embodiment, the method of formulating a pharmaceutical composition of etanercept further comprises aliquoting the pharmaceutical composition into a drug product form.

In another aspect, the present invention provides a kit comprising a pharmaceutical composition of etanercept as described above in a drug product form and instructions for storage and use.

In another aspect, the present invention provides a pharmaceutical composition comprising etanercept, NaCl, arginine, sucrose, a phosphate buffer and benzyl alcohol, wherein the pH of the composition is between 6.1 and 6.5. In one embodiment, the benzyl alcohol is at a concentration (v/v) of between 0.1% and 5.0%. In another embodiment, the concentration of benzyl alcohol is about 0.9%. In another embodiment, the pharmaceutical composition comprising etanercept further comprises polysorbate 20 at a concentration (w/v) of between 0.001% and 0.1%. In another embodiment, the concentration of polysorbate 20 is about 0.004%. In another embodiment, the pharmaceutical composition comprising etanercept consists essentially of etanercept at about 40-100 mg/mL, arginine at about 25 mM, sodium chloride at about 100 mM, sucrose at a concentration (w/v) of about 1%, phosphate buffer at about 25 mM, and benzyl alcohol at a concentration (v/v) of about 0.9%. In another embodiment, the pharmaceutical composition comprising etanercept consists essentially of etanercept at about 40-100 mg/mL, arginine at about 25 mM, sodium chloride at about 100 mM, sucrose at a concentration (w/v) of about 1%, phosphate buffer at about 25 mM, benzyl alcohol at a concentration (v/v) of about 0.9%, and polysorbate 20 at a concentration (w/v) of about 0.004%.

In another aspect, the present invention provides a single-dose container containing a pharmaceutical composition comprising etanercept as described above. In one embodiment, the pharmaceutical composition consists essentially of etanercept at about 40-100 mg/mL, arginine at about 25 mM, sodium chloride at about 100 mM, sucrose at a concentration (w/v) of about 1%, phosphate buffer at about 25 mM, and benzyl alcohol at a concentration (v/v) of about 0.9%. In another embodiment, the pharmaceutical composition consists essentially of etanercept at about 40-100 mg/mL, arginine at about 25 mM, sodium chloride at about 100 mM, sucrose at a concentration (w/v) of about 1%, phosphate buffer at about 25 mM, benzyl alcohol at a concentration (v/v) of about 0.9%, and polysorbate 20 at a concentration (w/v) of about 0.004%. In another embodiment, the single dose container is a vial, a syringe, or an autoinjector. In another embodiment, the single-dose container contains an aqueous formulation consisting of etanercept at 50.0 mg/mL, sodium chloride at 120 mM, L-arginine at 25 mM, sucrose at 1.0% (w/v).

In another aspect, the present invention provides a method of preparing a single-dose container containing a pharmaceutical composition comprising etanercept as described above, comprising filling the single-dose container with about a single dose of the pharmaceutical composition under sterile conditions.

BRIEF DESCRIPTION OF THE DRAWINGS

FIG. 1 shows the percent HMW (peak B) as detected by SEC for the etanercept stability assay of Example 3.

FIG. 2 shows the percent LMW as detected by dSEC for the etanercept stability assay of Example 3.

FIG. 3 shows the percent Peak 3 as detected by HIC for the etanercept stability assay of Example 3.

FIG. 4 shows the percent Peak 3 as detected by HIC for the stainless steel cryo-vessel storage etanercept stability assay of Example 4.

FIG. 5 shows the percent LMW as detected by dSEC for the stainless steel cryo-vessel storage etanercept stability assay of Example 4.

FIG. 6 shows the percent Peak B as detected by SEC for the stainless steel cryo-vessel storage etanercept stability assay of Example 4.

FIG. 7 shows the percent Peak B as detected by SEC for the freeze-thaw etanercept stability assay of Example 4.

FIG. 8 shows the pH stability of the conditioned AEX intermediate pool at controlled room temperature (CRT) in the assay of Example 6.

FIG. 9 shows the UF/DF pool pH (A) and conductivity (B) stability at CRT in the assay of Example 6.

FIG. 10 shows the pH (A) and conductivity (B) stability of etanercept formulated in SAS solution in the assay of Example 6.

DETAILED DESCRIPTION OF THE INVENTION

The invention provides improved pharmaceutical compositions of etanercept. As used herein, the phrase "pharmaceutical composition" is understood to refer to a formulation of a polypeptide suitable for injection and/or administration into a patient in need thereof. More particularly, a pharmaceutical composition is substantially sterile and does not contain any agents that are unduly toxic or infectious to the recipient. Etanercept is a soluble form of the p75 TNF receptor fused to an Fc domain of a human IgG1 (TNFR:Fc).

A commercially available etanercept is known as ENBREL® (Immunex Inc., Thousand Oaks, CA). Etanercept is produced by recombinant DNA technology in a Chinese hamster ovary (CHO) mammalian cell expression system. It consists of 934 amino acids and has an apparent molecular weight of approximately 150 kilodaltons (Physicians Desk Reference, 2002, Medical Economics Company Inc.). The full sequence expressed in CHO cells is shown below. However, it is to be understood that minor modifications and deletions of this sequence (up to 10%) may be possible and can be used within the scope of the invention.

```
                                            (SEQ ID NO: 1)
  1  Leu-Pro-Ala-Gln-Val-Ala-Phe-Thr-Pro-Tyr-

11  Ala-Pro-Glu-Pro-Gly-Ser-Thr-Cys-Arg-Leu-

21  Arg-Glu-Tyr-Tyr-Asp-Gln-Thr-Ala-Gln-Met-

31  Cys-Cys-Ser-Lys-Cys-Ser-Pro-Gly-Gln-His-

41  Ala-Lys-Val-Phe-Cys-Thr-Lys-Thr-Ser-Asp-

51  Thr-Val-Cys-Asp-Ser-Cys-Glu-Asp-Ser-Thr-

61  Tyr-Thr-Gln-Leu-Trp-Asn-Trp-Val-Pro-Glu-

71  Cys-Leu-Ser-Cys-Gly-Ser-Arg-Cys-Ser-Ser-

81  Asp-Gln-Val-Glu-Thr-Gln-Ala-Cys-Thr-Arg-

91  Glu-Gln-Asn-Arg-Ile-Cys-Thr-Cys-Arg-Pro-

101  Gly-Trp-Tyr-Cys-Ala-Leu-Ser-Lys-Gln-Glu-

111  Gly-Cys-Arg-Leu-Cys-Ala-Pro-Leu-Arg-Lys-

121  Cys-Arg-Pro-Gly-Phe-Gly-Val-Ala-Arg-Pro-

131  Gly-Thr-Glu-Thr-Ser-Asp-Val-Val-Cys-Lys-

141  Pro-Cys-Ala-Pro-Gly-Thr-Phe-Ser-Asn-Thr-

151  Thr-Ser-Ser-Thr-Asp-Ile-Cys-Arg-Pro-His-

161  Gln-Ile-Cys-Asn-Val-Val-Ala-Ile-Pro-Gly-

171  Asn-Ala-Ser-Met-Asp-Ala-Val-Cys-Thr-Ser-

181  Thr-Ser-Pro-Thr-Arg-Ser-Met-Ala-Pro-Gly-

191  Ala-Val-His-Leu-Pro-Gln-Pro-Val-Ser-Thr-

201  Arg-Ser-Gln-His-Thr-Gln-Pro-Thr-Pro-Glu-

211  Pro-Ser-Thr-Ala-Pro-Ser-Thr-Ser-Phe-Leu-

221  Leu-Pro-Met-Gly-Pro-Ser-Pro-Pro-Ala-Glu-

231  Gly-Ser-Thr-Gly-Asp-Glu-Pro-Lys-Ser-Cys-

241  Asp-Lys-Thr-His-Thr-Cys-Pro-Pro-Cys-Pro-

251  Ala-Pro-Glu-Leu-Leu-Gly-Gly-Pro-Ser-Val-

261  Phe-Leu-Phe-Pro-Pro-Lys-Pro-Lys-Asp-Thr-

271  Leu-Met-Ile-Ser-Arg-Thr-Pro-Glu-Val-Thr-

281  Cys-Val-Val-Val-Asp-Val-Ser-His-Glu-Asp-

291  Pro-Glu-Val-Lys-Phe-Asn-Trp-Tyr-Val-Asp-

301  Gly-Val-Glu-Val-His-Asn-Ala-Lys-Thr-Lys-

311  Pro-Arg-Glu-Glu-Gln-Tyr-Asn-Ser-Thr-Tyr-

321  Arg-Val-Val-Ser-Val-Leu-Thr-Val-Leu-His-

331  Gln-Asp-Trp-Leu-Asn-Gly-Lys-Glu-Tyr-Lys-

341  Cys-Lys-Val-Ser-Asn-Lys-Ala-Leu-Pro-Ala-

351  Pro-Ile-Glu-Lys-Thr-Ile-Ser-Lys-Ala-Lys-

361  Gly-Gln-Pro-Arg-Glu-Pro-Gln-Val-Tyr-Thr-

371  Leu-Pro-Pro-Ser-Arg-Glu-Glu-Met-Thr-Lys-

381  Asn-Gln-Val-Ser-Leu-Thr-Cys-Leu-Val-Lys-

391  Gly-Phe-Tyr-Pro-Ser-Asp-Ile-Ala-Val-Glu-

401  Trp-Glu-Ser-Asn-Gly-Gln-Pro-Glu-Asn-Asn-

411  Tyr-Lys-Thr-Thr-Pro-Pro-Val-Leu-Asp-Ser-

421  Asp-Gly-Ser-Phe-Phe-Leu-Tyr-Ser-Lys-Leu-

431  Thr-Val-Asp-Lys-Ser-Arg-Trp-Gln-Gln-Gly-

441  Asn-Val-Phe-Ser-Cys-Ser-Val-Met-His-Glu-

451  Ala-Leu-His-Asn-His-Tyr-Thr-Gln-Lys-Ser-

461  Leu-Ser-Leu-Ser-Pro-Gly-Lys
```

The invention provides a pharmaceutical composition comprising etanercept but containing essentially no additional buffering agent. The phrase "additional buffering agent" refers to a component of an etanercept composition or formulation, other than etanercept itself, that contributes significantly to the buffering capacity of the composition or formulation. Etanercept itself has been shown herein to provide all the needed buffering to maintain the pH between 6.1 and 6.5, and in particular at about 6.2-6.3, under the conditions described below. As demonstrated below in Example 1, this pH range has been shown to be effective to maintain the desired stability characteristics of an etanercept formulation (less than 6% high molecule weight aggregates and less than 28% misfolded and clipped species).

The phrase "essentially no additional buffering agent" means that there is less than 0.5 mM of any buffering agent other than etanercept. The phrase "total additional buffering agent" refers collectively to all of the components of an etanercept composition or formulation, except for etanercept itself, that contribute significantly to the buffering capacity of the composition or formulation. In certain embodiments, pharmaceutical compositions according to the invention comprise less than 2.0 mM total additional buffering agent, less than 1.5 mM total additional buffering agent, less than 1.0 mM total additional buffering agent, less than 0.5 mM total additional buffering agent, less than 0.25 mM total additional buffering agent, less than 0.1 mM total additional buffering agent, or less than 0.05 mM of total additional buffering agent. In typical pharmaceutical compositions, additional buffering agents are used to maintain the pH in a desired range, often at concentrations of 5.0 mM or higher. Various well known additional buffering agents are histidine, potassium phosphate, sodium or potassium citrate, maleic acid, ammonium acetate, tris-(hydroxymethyl)-aminomethane (tris), various forms of acetate and diethanolamine. One common buffering agent is sodium phosphate as its buffering capacity is at or near pH 6.2. Sodium phosphate is the buffering agent used in the current commercial liquid formulation of etanercept since its desired pH is 6.3. In the invention described herein, essentially no sodium phosphate is present in the pharmaceutical formulation of etanercept. Surprisingly, despite the absence of essentially any additional buffering agent, the pH of the inventive pharmaceutical composition is maintained between 6.1 and 6.5, even after extended storage. Even more surprisingly, when injected into subjects (e.g., a human subject or a patient), the pharmaceutical composition with essentially no additional buffering agent results in significantly less pain than the current buffered commercial formulation. Although phosphate is often chosen as a buffer for pharmaceutical compositions because of the close to neutral pH buffering capacity and belief that it is one of the less painful buffer components (as compared to, for example, citrate buffer), the instant inventors have determined that phosphate buffer at around pH 6.3 does contribute to pain upon injection.

Unless otherwise clear from the context of its use, a "formulation solution" or "formulation buffer" is a solution or buffer that does not itself contain etanercept but is used to make a formulation comprising etanercept.

Typically, the etanercept concentration in the pharmaceutical compositions of the invention is between about 40 mg/mL and about 200 mg/mL in an aqueous formulation (e.g., water as the solvent). More preferably, the etanercept concentration is between about 40 mg/mL and about 100 mg/mL, yet more preferably between about 40 mg/mL and about 75 mg/mL, and optionally about 50 mg/mL.

The pharmaceutical compositions of the invention also contain arginine. Arginine has been shown to make a substantial contribution to stabilizing etanercept in a liquid formulation (see U.S. Pat. No. 7,648,702, incorporated herein by reference). Pharmaceutically appropriate forms of arginine are commercially available. Typically, L-arginine (e.g., L-arginine HCl or L-arginine base) is the arginine used for pharmaceutical formulations. It is understood that within the pH range of 6.0 and 6.6, and in particular at a pH of about 6.2-6.3, arginine does not contribute meaningfully to the buffering capacity of a formulation. Accordingly, it is not an additional buffering agent in the etanercept formulations or compositions of the invention. The concentration of arginine in the compositions of the invention are preferably from about 1 mM to about 1 M, more preferably from about 10 mM to about 200 mM, or alternatively from about 5 mM to about 100 mM, more preferably from about 10 mM to about 100 mM, even more preferably from about 15 mM to about 75 mM, and yet more preferably at about 25 mM. Thus, in one aspect of the invention, the pharmaceutical composition comprises about 50 mg/mL to 75 mg/mL etanercept and about 25 mM arginine, wherein the pharmaceutical composition has essentially no additional buffering agent, and the pH of the composition is between 6.0 and 6.6. As used herein, the term "about" is understood to mean that there can be variation in the concentration of a component of the described formulation that can be up to and including 10% of the given value. For example, if a formulation has about 10 mg/mL of a polypeptide, this is understood to mean that a formulation can have between 9 to 11 mg/mL of the stated polypeptide.

The pharmaceutical compositions may contain additional excipients, as long as those excipients are not additional buffering agents, and in particular are not phosphate buffering agents. Examples of additional excipients according to the invention include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA or recombinant HA), dextran, PVA, hydroxypropyl methylcellulose (HPMC), polyethyleneimine, gelatin, polyvinylpyrrolidone (PVP), hydroxyethylcellulose (HEC); non-aqueous solvents such as: polyhydric alcohols, (e.g., PEG, ethylene glycol and glycerol) dimethylsulfoxide (DMSO) and dimethylformamide (DMF); amino acids such as: proline, L-serine, alanine, glycine, lysine hydrochloride, sarcosine and gamma-aminobutyric acid, and surfactants.

In some preferred embodiments of the invention, the excipients include NaCl and/or sucrose. NaCl may be present in the pharmaceutical composition at a concentration of from about 5 mM to about 200 mM, more preferably between about 20 mM to about 150 mM, even more preferably between about 80 mM to about 140 mM. Sucrose may be added to a concentration of between about 0.5% to about 2% (w/v) sucrose, more preferably between about 0.8% to about 1.2% (w/v) sucrose, even more preferably at about 1% (w/v) sucrose.

The osmolality of a pharmaceutical composition is preferably regulated in order to maximize the active ingredient's stability and also to minimize discomfort to the patient upon administration. It is generally preferred that a pharmaceutical composition be isotonic with serum, i.e., having the same or similar osmolality, which is achieved by addition of a tonicity modifier. Serum is approximately 300+/−50 milliosmolals per kilogram, thus it is contemplated that the osmolality of an isotonic pharmaceutical composition will be from about 180 to about 420 milliosmolals. In some embodiments, the range will be from about 250 to about 350 milliosmolals.

A tonicity modifier is understood to be a molecule that contributes to the osmolality of a solution. Examples of tonicity modifiers suitable for modifying osmolality include, but are not limited to amino acids (e.g., arginine, cysteine, histidine and glycine), salts (e.g., sodium chloride, potassium chloride and sodium citrate) and/or saccharides (e.g., sucrose, glucose and mannitol). The concentration of the tonicity modifier in the formulation is preferably between about 1 mM to 1M, more preferably about 10 mM to about 200 mM. In some embodiments, the concentrations of NaCl and sucrose are adjusted to generate a pharmaceutical composition that is isotonic. In some embodiments illustrated below by way of example, the pharmaceutical composition contains about 40-100 mg/mL etanercept, about 120 mM NaCl, about 25 mM arginine, about 1% sucrose, and water. In particular, the pharmaceutical composition can consist essentially of about 50-100 mg/mL etanercept, about 120 mM NaCl, about 25 mM arginine, about 1% sucrose, about 0.01% polysorbate 20, and water.

Optionally, the pharmaceutical compositions of the invention may include a surfactant. Surfactants are agents that reduce solution/surface induced stress. Examples of surfactants are polysorbates, such as polysorbate 20, polysorbate 40, polysorbate 60, and polysorbate 80 (e.g., TWEEN-20® (Sigma-Aldrich, St. Louis, Mo.) or TWEEN-80® (Sigma-Aldrich, St. Louis, Mo.)), sodium dodecyl sulfate (SDS), polyoxyethylene copolymer, poloxamers, such as poloxamer 188 (e.g., PLURONIC® F-68 (Sigma-Aldrich, St. Louis, Mo.) or poloxamer 407 (e.g., PLURONIC® F-127 (Sigma-Aldrich, St. Louis, Mo.). CHAPS, monolaurate, or any combination of the above. A preferred surfactant is polysorbate 20. For example, polysorbate 20 can be included in the pharmaceutical compositions at a concentration (w/v) of between about 0.001% and about 0.03%. In particular embodiments illustrated below by example, polysorbate 20 can be included in the pharmaceutical formulations at a concentration (w/v) of 0.01% or at about 0.004%.

Testing of the Pharmaceutical Compositions

The examples below illustrate how one of skill in art can determine whether a formulation is capable of maintaining the pH in a desired range. Essentially, the pharmaceutical composition is formulated and stored in the test containers (which may be glass vials, glass syringes, plastic syringes, stainless steel vessels, or any manner of sterile device suitable for pharmaceutical compositions) and the pH is assessed at time 0, and then at indicated times as appropriate. Usually, the testing conditions will anticipate needs for storage of the pharmaceutical composition, and will stress those conditions. For example, the formulations of the invention are able to maintain the desired pH under controlled room temperature (CRT) for at least 2 weeks, at least 4 weeks, at least 8 weeks, at least 12 weeks, and at least 24 weeks. CRT is defined by the USP, and has a temperature maintained thermostatically that encompasses the usual and customary working environment of 20° C. to 25° C. (68° F. to 77° F.); that results in a mean kinetic temperature calculated to be not more than 25° C.; and that allows for excursions between 15° C. and 30° C. (59° F. and 86° F.) that are experienced in pharmacies, hospitals, and warehouses.

In one aspect, the pharmaceutical compositions of the invention exhibit particular quality attributes. The testing of these quality attributes is also described below by way of example. For example, the pharmaceutical compositions of the invention contain less than 6% of the total etanercept aggregated in a high molecular weight form as assessed using size exclusion chromatography. As another example, the pharmaceutical compositions of the invention contain less than 28% of the total amount of etanercept is in a misfolded form as assessed using hydrophobic interaction chromatography.

The pharmaceutical compositions of the invention are capable of remaining stable by maintaining pH and/or other noted quality attributes (minimum high molecular weight forms and minimum misfolded forms) for the following temperatures and extended time periods (1) at −30° C. (frozen) for at least 4 weeks, at least 3 months, at least 6 months, at least 12 months, and at least 36 months; (2) for up to 1 freeze/thaw cycle, up to 2 freeze/thaw cycles, up to 3 freeze/thaw cycles, and up to 5 freeze/thaw cycles; (3) at 4° C. (refrigerated temperature) for at least 2 weeks, at least 4 weeks, at least 8 weeks, at least 12 weeks, at least at least 24 weeks, and at least 52 weeks; (4) at 25° C. (room temperature) for at least 2 weeks, at least 4 weeks, at least 8 weeks, at least 12 weeks, at least 24 weeks; and (5) at 40° C. (accelerated stability testing) for at least 2 weeks.

The pharmaceutical compositions of the invention also exhibit the surprising result of reduced pain upon injection into a subject. This property can be assessed using the Visual Analog Scale (VAS) that has been validated by Gallagher et al, 2002, Am. J. Em. Med. v20; i4: 287-290. Trained health professionals administer the drug via injection, and within 30 seconds after each injection, subjects assessed their level of injection pain using a 100 mm Visual Analog Scale (VAS). A difference of 13 to 16 mm on the VAS is considered to be clinically meaningful. Using this technique, it was demonstrated that a placebo formulation without phosphate induced significantly less pain than a placebo formulation containing phosphate at pH 6.3 and the current commercial formulation containing both etanercept and phosphate at pH 6.3.

Production and purification of the etanercept to be used in the pharmaceutical compositions and methods of the invention can be performed by any standard method. Typically, etanercept is expressed recombinantly in CHO cells and secreted into the medium. The medium is collected, filtered, and purified using, for example, various chromatography techniques. For example, protein A can be used to purify Fc domain containing polypeptides such as etanercept, and is advantageous as a first processing step. Other techniques for polypeptide purification such as fractionation on an ion-exchange column, ethanol precipitation, reverse phase HPLC, chromatography on silica, chromatography on heparin SEPHAROSE™, chromatography on an anion or cation exchange resin (such as a polyaspartic acid column), hydroxyapatite chromatography, gel electrophoresis, dialysis, and affinity chromatography, and any combination of purification techniques known or yet to discovered. Examples of useful production and purification techniques can be found in U.S. Pat. No. 7,294,481 (Fung), U.S. Pat. No. 7,452,695 (Van Ness et al.), U.S. Pat. No. 7,122,641 (Vedantham et al.), U.S. Pat. No. 7,157,557 (Sassenfeld et al.), U.S. Pat. No. 7,300,773 (Drapeau et al.), U.S. Pat. No. 8,163,522 (Brockhaus et al.), and U.S. Pat. No. 7,648,702 (Gomhotz et al.).

Methods of the Invention

The invention also provides a method of formulating a pharmaceutical composition of etanercept to remove buffer and maintain pH at a target range, comprising formulating the etanercept in a buffered formulation in the target range, and exchanging the buffered formulation against an unbuffered formulation that is within in or just below that target range, and collecting the resulting pharmaceutical formulation of the etanercept. In a preferred embodiment illustrated below by way of example, the method provides formulating a pharmaceutical composition of etanercept to remove buffer and maintain pH from 6.0 to 6.6, comprising formulating the etanercept formulation in a buffered formulation at between pH 6.0 to 6.6, and exchanging the buffered formulation against an unbuffered formulation that is between pH 5.6 and 6.5, and collecting the resulting pharmaceutical formulation. In order to achieve an unbuffered composition of etanercept that maintains its pH from 6.1 to 6.5, it is important to ensure that the pH of both the starting buffered etanercept formulation and the unbuffered formulation is calibrated. For example, if the starting buffered etanercept formulation is at pH 7.2, it will be adjusted with a strong acid, such as HCl, to within the range 6.1 to 6.5. Similarly, the unbuffered formulation that is used for exchange should be titrated to between pH 5.6 and 6.5. Because the unbuffered formulation used for exchange has no buffering agent, care should be used during titration.

To exchange the buffered formulation against an unbuffered formulation, one of skill in the art can make use of a variety of buffer exchange techniques that are well known in the art. Dialysis makes use of selective diffusion through a semi-permeable membrane to remove unwanted smaller molecules from a larger protein formulation. In one embodiment, equilibrations are done serially until a desired fold reduction in the concentration of an unwanted molecule is achieved. For example, three serial equilibrations, each at or greater than 100-fold dilution, can be used to achieve a concentration reduction of 1,000,000-fold or greater. Ultrafiltration and diafiltration are similar to dialysis in that they use a semi-permeable membrane. But unlike the passive diffusion of dialysis, ultrafiltration and diafiltration involves forcing solutions through the membrane using various techniques. Pressure and centrifugation are typically used. Still another method of buffer exchange can be performed using gel filtration or size exclusion chromatography. There are many other chromatographic techniques that also can be used to achieve buffer exchange that are well within the skill of those in the art such as ion exchange chromatography, hydrophobic interaction chromatography, and mixed mode chromatography.

After the buffered formulation is exchanged into the unbuffered formulation, the methods of the invention include collecting the resulting pharmaceutical formulation. At this point, essentially all buffer has been removed, but the pH is still maintained at the desired levels. For a pharmaceutical composition containing etanercept, the pH is maintained at between 6.0 and 6.6.

The pharmaceutical formulation may be further treated as necessary. For example, a surfactant can be added. In another example, if desired to remove particles, the pharmaceutical composition can be filtered. Alternatively or in addition, the methods of the invention also include aliquoting the pharmaceutical compositions into a drug product form. Such drug product forms are distributed for final use by patients or health care providers. The pharmaceutical compositions of this invention are particularly useful for parenteral administration, i.e., subcutaneously, intramuscularly, intravenously, intraperitoneal, intracerebrospinal, intra-articular, intrasynovial, and/or intrathecal. Parenteral administration can be by bolus injection or continuous infusion. Pharmaceutical compositions for injection may be presented in unit dosage form, e.g., in ampoules or in multi-dose containers. The pharmaceutical compositions may, if desired, be presented in a vial, pack or dispenser device which may contain one or more unit dosage forms containing the active ingredient. In one embodiment the dispenser device can comprise a syringe having a single dose of the liquid formulation ready for injection. In another embodiment, the pharmaceutical composition is aliquoted into a cassette component for use with a reusable autoinjector. Yet another aspect of the invention, the pharmaceutical compositions can be provided packaged in or with an on-body injector device. In still another embodiment, the pharmaceutical compositions can be aliquoted into a drug product form suitable for a needleless injection device.

The pharmaceutical composition can also be aliquoted into a format suitable as a depot preparation. Such long acting formulations may be administered by implantation (for example subcutaneously or intramuscularly) or by intramuscular injection. Thus, for example, the formulations may be modified with suitable polymeric or hydrophobic materials (for example as an emulsion in an acceptable oil) or ion exchange resins, or as sparingly soluble derivatives, for example, as a sparingly soluble salt.

In another embodiment, the present invention is directed to a kit or container, which contains the pharmaceutical composition of the invention. The kit can also be accompanied by instructions for the storage and use of the pharmaceutical compositions. The container can be, for example, a single-use container, i.e., a container that holds one dose formulation of the present invention. It is understood that a single-use container might contain a single dose plus enough extra to ensure that a full single dose can be administered to a patient from the container, but not so much extra that the container could be used to administer a second dose. Examples of containers suitable for use in certain aspects of the present invention (whether they be single-use or multiple-use containers) include vials, syringes, and auto-injectors. Examples of suitable auto-injectors include those found in U.S. Pat. Nos. 8,177,749, 8,052,645, and 8,920,374, in U.S. patent application Ser. Nos. 12/993,163, 13/269,750, 13/454,531, 14/112,479, 14/777,255, and 14/777,259, and in PCT Publications WO 2014/0089393, WO 2016/033496, and WO 2016/033507, each of which is incorporated herein by reference in its entirety.

The etanercept-containing compositions and formulations of the present invention, as well as the syringes, autoinjectors, kits, and the like described herein, can be used in the treatment of patients with conditions that respond to treatment with etanercept. Examples of such conditions include rheumatoid arthritis, psoriatic arthritis, ankylosing spondylitis, and psoriasis. Methods of treating patients with etanercept are described in, for example, U.S. Pat. Nos. 7,915,225, 8,119,605, 8,410,060, 8,722,631, and 8,119,604, each of which is incorporated herein by reference in its entirety.

The invention will be more fully understood by reference to the following examples. The examples should not, however, be construed as limiting the scope of the invention.

EXAMPLES

Example 1: Stability Testing of Various Formulations

This example demonstrates the effects of pH and buffer on etanercept at 50 mg/mL, and assesses the stability of a high concentration (100 mg/mL) solution without added phosphate buffer. The following formulations were tested.

TABLE 1

Formulations for pH Screen

| Formulation Name | Buffer | Excipients | Polysorbate Added | Final pH | Protein Conc (mg/mL) |
|---|---|---|---|---|---|
| A45SuT | 10 mM sodium acetate | 9% sucrose | 0.004% PS20 | 4.5 | 50 |
| A52SuT | 10 mM sodium acetate | 9% sucrose | 0.004% PS20 | 5.2 | 50 |
| A58SuT | 10 mM sodium acetate | 9% sucrose | 0.004% PS20 | 5.8 | 50 |
| 50_SAST_100NaCl | None | 25 mM L-arginine, 100 mM NaCl, 1% sucrose | 0.004% PS20 | 6.3 | 50 |
| 100_SAST_100NaCl | None | 25 mM L-arginine, 100 mM NaCl, 1% sucrose | 0.004% PS20 | 6.3 | 100 |

TABLE 1-continued

Formulations for pH Screen

| Formulation Name | Buffer | Excipients | Polysorbate Added | Final pH | Protein Conc (mg/mL) |
|---|---|---|---|---|---|
| PASST + BeOH | 25 mM phosphate | 25 mM L-arginine, 100 mM NaCl, 1% sucrose, 0.9% benzyl alcohol | 0.004% PS20 | 6.3 | 50 |
| PASST (control) | 25 mM phosphate | 25 mM L-arginine, 100 mM NaCl, 1% sucrose | 0.004% PS20 | 6.3 | 50 |

Materials: Enbrel drug substance in PASS (25 mM phosphate buffer, 25 mM L-arginine, 100 mM NaCl, 1% sucrose) at 50 mg/mL was used for this study. For the acetate and buffer-free formulation, the material was dialyzed into the new formulations (without polysorbate) and concentrated to 50 mg/mL using 10,000 MWCO centripreps. A sample of 50_SAS_100NaCl was also concentrated to 100 mg/mL (100_SAS_100NaCl). Benzyl alcohol was spiked into the current formulation to a final concentration of 0.9%. A 1% stock solution of poly sorbate 20 was prepared fresh and spiked into all formulation to a final concentration of 0.004%. All formulations were manually filled into 1 mL long BD glass syringes to a volume of 0.5 mL and then stoppered using an ASPU vacuuming stoppering unit.

Methods: The pH was measured using a Mettler Toledo SevenEasy pH meter combined with a Mettler Inlab Micro-Probe. Samples were warmed to room temperature prior to measurements. Osmolality was measured using The Advanced Osmometer Model 3900. Each measurement was performed using 250 µL of sample and 290 osmolality standards were tested to ensure the system was operating properly. Size exclusion HPLC was run on an Agilent 1100) HPLC with Chromeleon 7.2 software. Denatured size exclusion HPLC was run on an Agilent 1100 HPLC with Chromeleon 7.2 software.

Results: The pH for all formulations was maintained over 24 weeks.

TABLE 2 pH at indicated time points and temperatures

| | pH | | | |
|---|---|---|---|---|
| | t = 0 | t = 24 w | | |
| Sample | 4° C. | 4° C. | 25° C. | 40° C. |
| A45SuT | 4.60 | 4.66 | 4.66 | 4.61 |
| A52SuT | 5.10 | 5.13 | 5.16 | 5.08 |
| A58SuT | 5.61 | 5.60 | 5.66 | 5.62 |
| 50_SAST_100NaCl | 6.24 | 6.21 | 6.22 | 6.17 |
| 100_SAST_100NaCl | 6.32 | 6.21 | 6.20 | 6.19 |
| PASST + BeOH | 6.27 | 6.22 | 6.22 | 6.21 |
| PASST control | 6.26 | 6.21 | 6.21 | 6.19 |

TABLE 3

Aggregate levels (Peak B) by SEC, % of total, 4° C.

| sample | t = 0 | t = 4 w | t = 8 w | t = 12 w | t = 24 w |
|---|---|---|---|---|---|
| A45SuT | 0.9 | 1.1 | 1.1 | 1.2 | 1.2 |
| A52SuT | 1.2 | 1.4 | 1.5 | 1.6 | 1.4 |
| A58SuT | 1.0 | 1.2 | 1.2 | 1.3 | 1.3 |
| 50_SAST_100NaCl | 1.1 | 1.3 | 1.3 | 1.3 | 1.4 |
| 100_SAST_100NaCl | 1.1 | 1.4 | 1.5 | 1.5 | 1.6 |
| PASST + BeOH | 1.0 | 1.2 | 1.2 | 1.3 | 1.3 |
| PASST control | 1.0 | 1.1 | 1.2 | 1.2 | 1.3 |

TABLE 4

Aggregate levels (Peak B) by SEC, % of total, 25° C.

| sample | t = 0 | t = 4 w | t = 8 w | t = 12 w | t = 24 w |
|---|---|---|---|---|---|
| A45SuT | 0.9 | 2.0 | 2.7 | 3,2 | 4.1 |
| A52SuT | 1.2 | 2.7 | 3.1 | 3.6 | 4.6 |
| A58SuT | 1.0 | 1.9 | 2.6 | 3.1 | 4.4 |
| 50_SAST_100NaCl | 1.1 | 1.9 | 2.4 | 2.8 | 3.7 |
| 100_SAST_100NaCl | 1.1 | 2.6 | 3.3 | 3 9 | 5.3 |
| PASST + BeOH | 1.0 | 1.9 | 2.4 | 2.8 | 3.8 |
| PASST control | 1.0 | 1.8 | 2.2 | 2.6 | 3.5 |

TABLE 5

Aggregate levels (Peak B) by SEC, % of total, 40° C.

| sample | t = 0 | t = 2 w | t = 4 w | t = 8 w | t = 12 w | t = 24 w |
|---|---|---|---|---|---|---|
| A45SuT | 0.9 | 5.6 | 9.0 | 11.9 | 11.9 | 9.6 |
| A52SuT | 1.2 | 6.3 | 12.9 | 13.6 | 16.4 | 17.9 |
| A58SuT | 1.0 | 5.1 | 9.1 | 14.7 | 18.4 | 24.5 |
| 50_SAST_100NaCl | 1.1 | 3.9 | 6.8 | 12.1 | 16.0 | 26.0 |
| 100_SAST_100NaCl | 1.1 | 5.9 | 10.8 | 18.5 | 24.0 | 37.8 |
| PASST + BeOH | 1.0 | 6.3 | 12.0 | 21.4 | 28.1 | 45.5 |
| PASST control | 1.0 | 4.0 | 6.9 | 12.1 | 16.1 | 26.7 |

TABLE 6

Low molecular species (dSEC clips) 4° C.

| sample | t = 0 | t = 4 w | t = 8 w | t = 12 w | t = 24 w |
|---|---|---|---|---|---|
| A45SuT | 1.6 | 1.3 | 1.4 | 2.3 | 2.5 |
| A52SuT | 1.2 | 1.6 | 1.3 | 1.7 | 1.7 |
| A58SuT | 1.4 | 1.7 | 1.5 | 1.4 | 1.4 |
| 50_SAST_100NaCl | 0.9 | 1.5 | 1.4 | 1.4 | 1.5 |
| 100_SAST_100NaCl | 1.0 | 1.5 | 1.7 | 2.0 | 2.6 |
| PASST + BeOH | 1.0 | 1.5 | 1.2 | 1.4 | 1.3 |
| PASST control | 1.2 | 1.4 | 1.4 | 1.7 | 1.6 |

TABLE 7

Low molecular species (dSEC clips) 25° C.

| sample | t = 0 | t = 4 w | t = 8 w | t = 12 w | t = 24 w |
| --- | --- | --- | --- | --- | --- |
| A45SuT | 1.6 | 3.6 | 5.9 | 8.4 | 13.1 |
| A52SuT | 1.2 | 2.9 | 2.9 | 5.8 | 9.2 |
| A58SuT | 1.4 | 2.2 | 2.8 | 4.0 | 5.7 |
| 50_SAST_100NaCl | 0.9 | 2.2 | 2.4 | 2.9 | 4.7 |
| 100_SAST_100NaCl | 1.0 | 2.9 | 3.2 | 4.4 | 6.9 |
| PASST + BeOH | 1.0 | 2.2 | 2.2 | 3.3 | 4.4 |
| PASST control | 1.2 | 1.6 | 2.1 | 3.2 | 4.8 |

TABLE 8

Low molecular species (dSEC clips) 40° C.

| sample | t = 0 | t = 2 w | t = 4 w | t = 8 w | t = 12 w | t = 24 w |
| --- | --- | --- | --- | --- | --- | --- |
| A45SuT | 1.6 | 9.7 | 16.7 | 28.3 | 38.1 | 55.0 |
| A52SuT | 1.2 | 6.0 | 11.3 | 18.6 | 26.0 | 39.6 |
| A58SuT | 1.4 | 4.0 | 7.7 | 12.2 | 18.2 | 27.5 |
| 50_SAST_100NaCl | 0.9 | 3.6 | 5.9 | 8.6 | 12.8 | 18.7 |
| 100_SAST_100NaCl | 1.0 | 3.5 | 5.7 | 9.6 | 12.9 | 19.4 |
| PASST + BeOH | 1.0 | 3.6 | 5.8 | 9.8 | 13.2 | 20.5 |
| PASST control | 1.2 | 3.3 | 5.9 | 10.0 | 12.8 | 20.2 |

Conclusions: During long term storage at 25° C. and 40° C., the lower pH formulations, A45SuT, A52SuT, and A58SuT, exhibited undesirable levels of low molecular weight degraded or clipped species when analyzed using denatured size exclusion chromatography. The high concentration formulation 100_SAST_100NaCl stored at 25° C. and 40° C. began to show an increase in high molecular weight aggregates when analyzed using size exclusion chromatography, but performed similarly to the current commercial formulation at 4° C. The PASST+BeOH (which is the current commercial formulation modified by the addition of 0.004% polysorbate 20 and 0.9% benzyl alcohol) performed similarly to the current commercial formulation at both 4° C. and 25° C. but experienced an increase in high molecular weight species by SE-HPLC at later time points when stored at the elevated temperature of 40° C. However, the 50_SAST_100NaCl formulation maintained levels of high and low molecular weight species that were comparable to the current commercial formulation at all temperatures, even in the absence of phosphate buffer.

Example 2: Pain Study

This study was a single-center, randomized, single-blind, crossover design in which 48 healthy men and women received single SC injections of 6 solutions.

Test formulations (detailed below in Table 9) were administered by a trained healthcare professional in 6 unique sequences with 8 subjects randomized to each sequence. Injections were administered in each quadrant of the anterior abdominal wall and administered approximately 1 hour apart. Within 30 seconds after each injection, subjects assessed their level of injection pain using a 100 mm Visual Analog Scale (VAS). Adverse events were collected from the beginning of the first injection through 30 days after the first injection. Safety follow-up phone calls were conducted on day 2 (24 hours after the sixth injection) and day 31 (±2 days).

TABLE 9

Tested Formulations

| Solution | Description | Volume | Composition |
| --- | --- | --- | --- |
| A. | Negative pain control | 1.0 | 10 mM sodium acetate, 9% (w/v) sucrose, 0.004% (w/v) polysorbate 20, pH 5.2 |
| B. | Commercial formulation placebo | .098 | 25 mM sodium phosphate, 25 mM L-arginine, 100 mM sodium chloride, 1.0% (w/v) sucrose, pH 6.3 |
| C. | Commercial formulation placebo with benzyl alcohol | 1.0 | 100 mM sodium chloride, 25 mM sodium phosphate, 25 mM L-arginine, 1.0% (w/v) sucrose, 0.01% (w/v) polysorbate 20, 0.9% (w/v) benzyl alcohol |
| D. | Test formulation without sodium phosphate | 1.0 | 100 mM sodium chloride, 25 mM L-arginine, 1.0% (w/v) sucrose, 0.01% (w/v) polysorbate 20 |
| E. | Test formulation without sodium phosphate | 0.51 | 100 mM sodium chloride, 25 mM L-arginine, 1.0% (w/v) sucrose, 0.01% (w/v) polysorbate 20 |
| F. | Commercial formulation etanercept 50 mg/mL | 0.98 | 50 mg/mL etanercept in a solution consisting of 100 mM sodium chloride, 25 mM sodium phosphate, 25 mM L-arginine 1% sucrose, pH 6.3 |

Statistical Methods: All analyses were conducted on the safety analysis set, which consisted of all subjects who received at least one solution. To provide 93.4% power to detect a 15 mm difference between the solutions ($\alpha=0.05$, 2 sided), a sample size of 48 subjects (8 per sequence) was selected. A difference of 13 to 16 mm on the VAS is considered to be clinically meaningful (Gallagher et al, 2002, Am. J. Em. Med. v20; i4: 287-290).

Summary statistics (mean, SD, standard error [SE], median, minimum, maximum) were calculated for VAS scores by solution. VAS scores were analyzed using an analysis of variance (ANOVA) model, which included sequence, solution, and period as independent variables, and subject within sequence as a random effect. No adjustment was made for multiple comparisons.

Mean differences in VAS score for the primary and secondary comparisons, corresponding 95% confidence intervals (95% CI), and p-values were provided.

TABLE 10

Summary of VAS Scores

| immediately after injection | Soln A | Soln B | Soln C | Soln D | Soln E | Soln F |
|---|---|---|---|---|---|---|
| N | 48 | 48 | 48 | 48 | 48 | 48 |
| Mean | 19.6 | 53.6 | 28,.7 | 29.8 | 29.6 | 53.4 |
| SD | 18.0 | 27.9 | 23 5 | 26.4 | 24.3 | 32.4 |
| SE | 2.6 | 4.0 | 3.4 | 3.8 | 3.5 | 4.7 |
| Median | 13.0 | 59.0 | 24.0 | 21.5 | 21.0 | 49.0 |
| Min, Max | 0, 66 | 1, 98 | 1, 99 | 0, 94 | 1, 86 | 2, 100 |

Conclusions: Both Solution C (non-product specific placebo with benzyl alcohol) and Solution D (non-product specific placebo without sodium phosphate) had significantly lower mean VAS scores than Solution B (etanercept placebo; $p<0.001$), indicating relatively less injection site pain with these 2 solutions. No significant differences in mean VAS scores were found between Solutions C and D, between Solution B (etanercept placebo) and Solution F (active etanercept), or between different injection volumes (0.51 and 1.0 mL). Solution A (negative pain control) was associated with the least pain compared with all the other solutions. Seven subjects had 1 or more adverse events. All of the adverse events were CTCAE Grade 1 non-serious injection site reactions.

Example 3: Long Term Stability Testing of Formulation Candidates

A long-term study was performed to monitor etanercept stability in several new formulation candidates at 50 mg/mL. The stability was assessed on 1 mL fills in 1 mL staked glass needle syringes using SE-HPLC, HIC HPLC, dSEC HPLC, and particulate matter (HIAC) after storage at 4° C., 25° C. and 40° C. Osmolality and protein concentration were tested at time zero only, and pH was tested at time zero and after 12 weeks of storage to confirm that there was no pH drift. The results of the study showed that the formulations tested remained similar to the current commercial formulation after 12 weeks at the accelerated temperature of 40° C., as well as 24 weeks at the recommended storage of 2-8° C. and at the accelerated temperature of 25° C.

TABLE 11

Formulation conditions at 50 mg/mL etanercept

| Formulation Name | Buffer | Other Excipients | pH |
|---|---|---|---|
| PASST (control) | 25 mM phosphate | 25 mM L-arginine, 100 mM NaCl, 1% sucrose, 0.010% polysorbate 20 | 6.3 |
| SAST_100NaCl | none none | 25 mM L-arginine, 100 mM NaCl, 1% sucrose, 0.010% polysorbate 20 | 6.3 |
| SAST_120NaCl | | 25 mM L-arginine, 120 mM NaCl, 1% sucrose, 0.010% polysorbate 20 | 6.3 |

Materials: Enbrel drug substance in PASS (25 mM phosphate buffer, 25 mM L-arginine, 100 mM NaCl, 1% sucrose) at 50 mg/mL was used for this study. The material was diafiltered into PASS and SAS_100NaCl (25 mM L-arginine, 100 mM NaCl, 1% sucrose) at 50 mg/mL and then ultrafiltered to ~75 mg/mL. The 50 mg/mL formulations were prepared by diluting the post-UF/DF PASS and SAS material with the corresponding solution. The SAST_120NaCl was prepared by diluting the 75 mg/mL SAS material using a concentrated NaCl stock solution to achieve a final concentration of 120 mM NaCl. A 1% stock solution of polysorbate 20 was prepared fresh and spiked into all formulation to a final concentration of 0.010%. All formulations were manually filled into 1 mL long BD glass syringes to a volume of 1 mL and then stoppered using an ASPU vacuuming stoppering unit.

Methods: The pH was measured using a Mettler Toledo SevenEasy pH meter combined with a Mettler Inlab Micro-Probe. Samples were warmed to room temperature prior to measurements. Protein concentration measurements using absorbance at 280 nM for all samples were performed at room temperature using the DropSense96 UV/V is Lab Chip DS system. Each sample was measured neat with at least three replicates (3 μL each), including a formulation solution blank. Osmolality was measured using The Advanced Osmometer Model 3900. Each measurement was performed using 250 μL of sample and 290 mOsm osmolality standards were tested to ensure the system was operating properly. Size exclusion HPLC was run on an Agilent 1100 HPLC with Chromeleon 7.2 software. Hydrophobic interaction HPLC was run on an Agilent 1100 HPLC with Chromeleon 7.2 software at an absorbance of 215 nm. Denatured size exclusion HPLC was run on an Agilent 1100 HPLC with Chromeleon 7.2 software. Sub-visible particle analysis was performed using a HACH HIAC/Royco particle counter system equipped with an HRLD-150 laser and Pharm Spec software. All samples were diluted with PASS formulation buffer to 25 mg/mL. Samples were thoroughly mixed, uncapped and degassed for 2 hours at 75 torr prior to analysis. Four (4) sips of 1.0 mL each (no tare volume) were performed, with the first sip discarded and the remaining three sips averaged. Data for particle sizes 2, 5, 10, and 25 μm was collected at all time points. The results account for the dilution and are reported as cumulative counts per milliliter.

Results and Discussion: The pH of all formulations was measured at time zero and after twelve weeks at all temperatures. No trends were observed as a function of time or storage temperature. The measured pH values for all samples can be found in Table 12. No drift in pH was observed after 52 weeks of storage at 4° C., 24 weeks of storage at 25° C. or twelve weeks of storage at 40° C.; all samples met the acceptance criteria of +/−0.2 pH units from the target pH of 6.3.

TABLE 12

Measured pH for samples

| Formulation Acronym | t = 0 | t = 52 w 4° C. | t = 24 w 25° C. | t = 12 w 40° C. |
|---|---|---|---|---|
| PASST | 6.27 | 6.30 | 6.32 | 6.28 |
| SAST_100NaCl | 6.23 | 6.15 | 6.25 | 6.20 |
| SAST_120NaCl | 6.22 | 6.16 | 6.24 | 6.15 |

The protein concentration of all formulations was tested at time zero. The protein concentration results for all samples can be found in Table 13. All samples met the acceptance criteria.

TABLE 13

Protein Concentration measurements

| Formulation Acronym | t = 0 |
|---|---|
| PASST | 51.1 |
| SAST_100NaCl | 51.4 |
| SAST_120NaCl | 51.0 |

Osmolality was tested at time zero only. The osmolality results for all samples can be found in Table 14. All formulations were at their target osmolality. Due to differences in buffer and excipient levels, the osmolality was not expected to be the same across the various formulations.

TABLE 14

Osmolality measurements

| Formulation Acronym | t = 0 (measured) | theoretical |
|---|---|---|
| PASST | 314 | 313 |
| SAST_100NaCl | 262 | 263 |
| SAST_120NaCl | 299 | 300 |

SE-HPLC was performed to monitor aggregation levels as a function of formulation condition, time and temperature. Peak B is the amount of high molecular weight species (aggregate) that forms. Results showed no differences in Peak B between the PASST control and the buffer-less formulations at 4° C. and 25° C., with minor differences being observed after twelve weeks at 40° C. (FIG. 1). Peak B represents the total aggregate detected by SE-HPLC for these formulations. All samples remained acceptable (Peak B≤56%) after 52 weeks of storage at 4° C., 24 weeks of storage at 25° C., and after twelve weeks of storage at 40° C.

Denatured SE-HPLC was used to monitor clip species LMW. Results showed similar trends in HMW species, main peak, LMW between the formulations after 52 weeks (FIG. 2).

Changes in misfolded aggregates were monitored by HIC HPLC. Results at all tested temperatures showed no differences in Peak 3 between the PASST control and the buffer-less formulations (FIG. 3). All samples remained within acceptable ranges (Peak 1≤5%, Peak 2≥70%, Peak 3≤28%) after 52 weeks of storage at 4° C., 24 weeks of storage at 25° C., and after twelve weeks of storage at 40° C.

Sub-visible particles were monitored by light obscuration particle counting (HIAC). Results were in line with historical PFS data and were similar between the formulations across all temperatures after twelve weeks. No trends could be established from this data set, as a single vial containing three pooled syringes was used at each time point and there is a high level of syringe-to-syringe variability in the contribution to silicone oil droplets.

Conclusions: The long-term stability of several new reformulation candidates and the current commercial formulation with the addition of polysorbate was assessed at 4° C., 25° C. and 40° C. No significant differences were observed between the formulations after 52 weeks at 4° C. and 24 weeks at 25° C. by SE-, dSEC, or HIC HPLC assays as well as by light obscuration; minor differences were observed after twelve weeks at 40° C. by HPLC assays. No drift in pH was observed and all formulations remained within acceptable ranges. The results of the study showed that the SAST_120NaCl and SAST_100NaCl formulations at 50 mg/mL were stable and similar to the current commercial formulation after twelve weeks at the recommended storage temperature of 2° C. to 8° C.

Example 4: Freeze/Thaw and Long Term Stability of Top Reformulation Candidates in Stainless Steel Containers A freeze/thaw cycling study was performed to monitor etanercept stability in three new formulations candidates at 50 mg/mL. Formulations compared to the current commercial formulation PASS (25 mM phosphate buffer, 25 mM L-arginine, 100 mM NaCl, 1% sucrose) were SAST_100NaCl (25 mM L-arginine, 100 mM NaCl, 1% sucrose, 0.010% polysorbate 20), SAS_120NaCl (25 mM L-arginine, 120 mM NaCl, 1% sucrose), and SAST_120NaCl (25 mM L-arginine, 120 mM NaCl, 1% sucrose, 0.010% polysorbate 20). The stability to aggregation when cycled between −30° C. and 4° C. in 55 mL stainless steel cryo vessels was assessed using SE-HPLC up to five freeze/thaw cycles.

Additionally, a long-term study was performed to monitor etanercept stability in a new formulation candidate at 50 mg/mL. Formulation compared to the current commercial formulation PASS (25 mM phosphate buffer, 25 mM L-arginine, 100 mM NaCl, 1% sucrose), was SAST_120NaCl (25 mM phosphate buffer, 25 mM L-arginine, 100 mM NaCl, 1% sucrose, 0.010% polysorbate 20). The stability when stored in 10 mL and 55 mL stainless steel cryo vessels was assessed using SE-HPLC, HIC HPLC, dSEC HPLC, and particulate matter (HIAC). Storage temperatures and time points were −30° C. for up to 36 months and 4° C. for up to twelve months. Results at 52 weeks are presented here.

Results: The pH of all formulations remained consistent at the 52 week time point and through five cycles of freeze/thaw.

TABLE 15 pH, Protein concentration and Osmolality

| Sample | Conc. (mg/mL) | Osmolality (mOsm) | pH t = 0 | pH 52 wk −30° C. | pH 52 wk 4° C. |
|---|---|---|---|---|---|
| PASS | 49.5 | 304 | 6.34 | 6.20 | 6.22 |
| SAST_120NaCl | 51.4 | 303 | 6.27 | 6.19 | 6.20 |

TABLE 16 pH, Protein Concentration and Osmolality for Freeze/Thaws

| Sample | Conc. (mg/mL) | Osmolality (mOsm) | pH 0 F/T | pH 3 F/T | pH 5 F/T |
|---|---|---|---|---|---|
| PASS | 47.9 | 310 | 6.30 | 6.29 | 6.27 |
| SAST_100NaCl | 48.8 | 259 | 6.19 | 6.18 | 6.16 |
| SAST_120NaCl | 48.1 | 294 | 6.17 | 6.19 | 6.18 |
| SAS_120NaCl | 48.6 | 300 | 6.17 | 6.17 | 6.18 |

No trends were observed by HIAC for >10 μm particles, although there were small increases in >2 and >5 μm particles in the SAST_120NaCl formulation. As shown in FIG. 4, FIG. 5, and FIG. 6, no significant differences were observed between the formulations by HIC, dSEC, or SEC. No significant changes were observed by SEC between the formulations after exposure to five freeze thaw cycles. See FIG. 7.

Conclusion: The results of the study thus far showed that the new formulation tested remained similar to the current commercial formulation after 52 weeks storage in stainless steel cryo vessels at −30° C. as well as at 4° C.

Example 5: Exchange into SAS and PASS Solutions

The purpose of these examples was to dialyze different preparations of etanercept in TMS (tris, mannitol, sucrose) into the test formulation (L-arginine, sucrose, NaCl) and compare the final pH to the target pH.

Materials: Etanercept: 25 mg/mL, in TMS (10 mM Tris HCl, 4% mannitol, 1% sucrose, pH 7.4); SAS_100NaCl solution (100 mM NaCl, 25 mM L-arginine HCl, 1% sucrose, pH 6.3) for dialysis; PASS buffer (25 mM Phosphate, 100 mM NaCl, 25 mM L-arginine HCl, 1% sucrose, pH 6.3); 10,000 MWCO centripreps; 3-12 mL Slide-A-Lyzer dialysis cassettes, 10,000 MWCO; a Mettler Toledo MP220 pH meter and Mettler Toledo InLab MicroProbe.

Methods: For the UF/DF example, 25 mg/mL etanercept in TMS was concentrated to ~50 mg/mL by ultrafiltration using 30K MWCO Pellicon 3 cassettes on a Millipore Pellicon-2 mini system. The material was then diafiltered against SAS_100NaCl or PASS solution for 7 diavolumes, followed by concentration by ultrafiltration to 100 mg/mL. For the dialysis example, 25 mg/mL etanercept in TMS was concentrated to 50 mg/mL using 10,000 MWCO centripreps. The pH of the 50 mg/mL Sample in TMS was measured, as was the SAS dialysis solution, using the Mettler Toledo MP220 pH meter and InLab MicroProbe. The material was then dialyzed using 10,000 MWCO slide-a-lyzer dialysis cassettes. 9.5 mL of 50 mg/mL etanercept in TMS was added to the cassette and exchanged against 1000 mL of SAS100. Three exchanges were performed to achieve a 1,000,000 fold exchange. The first exchange occurred at 5 pm on Day 1 and went overnight. The second 1,000 mL exchange was at 8:30 am on Day 2. The third and final exchange was at 12:30 pm on Day 2. At 5:00 pm on Day 2 the protein was removed from the dialysis cassette (11 mL removed) and the pH was measured on the same Mettler Toledo MP220 pH meter. The measured pH was 6.98.

Results:
A summary of the results is shown below in Table 17.

TABLE 17 pH using various exchange methods and solutions

| Method of Exchange | Sample Name | Filtration Solution pH | Pre-Method Exchange pH | Post Method pH | Number of Exchanges |
|---|---|---|---|---|---|
| UF/DF | PASS, pH 6.3, 100 mg/mL | 6.34 | 7.56 | 6.34 | 7 Diafiltration volumes |
| UF/DF | SAS_100NaCl, pH 6.3, 100 mg/mL | 6.38 | 7.56 | 6.98 | 7 Diafiltration volumes |
| Dialysis | SAS_100NaCl, pH 6.3, 50 mg/mL | 6.29 | 7.56 | 6.98 | 1,000,000 fold exchange |

Conclusion: When the samples were ultrafiltrated/diafiltrated from a pre-exchange solution at pH 7.56 into the PASS buffer, the target pH of 6.34 was attained. However, when the samples were ultrafiltrated/diafiltrated into the SAS_100NaCl solution, the pH of the post-dialysis material that was achieved was 6.98, which was higher than expected and was not close to the final target pH of 6.3. Using dialysis as the exchange method into SAS_100NaCl achieved the same results.

Example 6: UF/DF Pool

Introduction: The formulation solution that was chosen following this study was termed SAS (120 mM sodium chloride, 25 mM L-arginine, 1% sucrose, pH 6.3), without added phosphate buffer. Since the previous example demonstrated that it was difficult to attain the target pH of 6.3 when either dialyzing or using UF/DF when starting from etanercept in a sample at pH 7.56, a different method of exchange into the SAS formulation was needed. Two methods were evaluated that utilized separate final UF/DF starting material: 1) column 3 (AEX) intermediate pool as the starting material, and 2) Enbrel drug substance in PASS formulation buffer (PASS DS intermediate pool) as the starting material. Each method is described below and summarizes the development of a final UF/DF unit operation step to produce 50 g/L SAS formulated etanercept, including preparation of SAS formulation solution, final UF/DF load conditioning and processing.

Methods: The SAS formulation solution is composed of 120 mM sodium chloride, 25 mM L-arginine, 1% sucrose, pH 6.3. An SAS formulation solution was titrated to pH 6.3 using 10 N NaOH. The volume of titrant required to reach the specific pH range was 4.4 μL/L SAS formulation solution. During execution of the SAS final UF/DF unit operation, following equilibration of the membranes at 10 L/m² with the SAS formulation solution, the pH of the permeate remained close to the pH of WFI rather than the pH of the SAS formulation solution. Without being bound to a particular theory, this is believed to be due to the low buffering capacity of the SAS formulation solution. The expected range for conductivity of the permeate following membrane equilibration using the range of the SAS formulation solution preparation is 12-16 mS/cm. A higher post equilibration pH than that of the SAS formulation solution is expected and should not raise concern or indicate that the membranes are not equilibrated.

AEX Intermediate Pool Starting Material: Prior to transferring the AEX intermediate pool into the retentate tank of an UF/DF tank, the pool was conditioned using 2 M HCl to a target pH of 6.3 (acceptable range 6.2-6.4). The volume of titrant required to reach the specific pH range was approximately 2.8 mL/L AEX intermediate pool.

Eight examples performed during development of the SAS final UF/DF unit operation step, using AEX intermediate pool as the starting material, are listed in Table 18. Two parameters were investigated: the pH of the conditioned AEX intermediate pool and the pH of the SAS formulation solution. The first three runs were analyzed for pH, conductivity, osmolality, protein concentration, and product quality. Runs 4 through 7 were only measured for pH, conductivity, osmolality, and protein concentration in order to determine impact of formulation solution pH and load pH impact UF/DF pool pH.

TABLE 18

AEX Intermediate Pool Starting Material: Load, Exchange Solution, and final UF/DF pool pH

| Run Number | Target Load pH | Target SAS | UF/DF Pool pH |
|---|---|---|---|
| 1 | 6.3 | 6.3 | 6.26 |
| 2 | 6.3 | 6.3 | 6.33 |
| 3 | 6.3 | 6.3 | 6.22 |
| 4 | 6.3 | 5.6 | 6.22 |
| 5 | 6.2 | 5.3 | 6.06 |
| 6 | 6.4 | 7.3 | 6.94 |
| 7 | 6.2 | 5.6 | 6.14 |
| 8 | 6.4 | 6.5 | 6.43 |

Results: The product quality results for the final SAS UF/DF pool, generated using AEX intermediate pool as the starting material, are shown in Table 19. The step yield for Run 1 was outside of the acceptance criteria; however, it was most likely an artifact of bench-scale processing and considered not significant to the conclusions of the study. All three final UF/DF SAS runs also met acceptance criteria for product quality using SEC and HIC analysis, as described above.

TABLE 19

AEX Intermediate Pool Starting Material: Final SAS UF/DF Pool Product Quality

| Parameter | Acceptance Criteria | Final SAS UF/DF Pool | | |
|---|---|---|---|---|
| | | Run 1 | Run 2 | Run 3 |
| pH | 6.1-6.5 | 6.26 | 6.22 | 6.33 |
| Protein Concentration (mg/mL) | 49-51 | 50.08 | 49.68 | 49.90 |
| Step Yield (%) | 95-103 | 93.4 | 99.5 | 100.5 |

Conditioned AEX Intermediate Pool Stability

The conditioned AEX intermediate pool can be held for up to 52.6 hours at controlled room temperature (CRT). The pH of the pool during the hold is shown in FIG. 8.

UF/DF Pool Stability

The final UF/DF SAS pool, generated using AEX intermediate pool as the starting material, can be held for up to 96.3 hours at CRT. The pH and conductivity during the hold are shown in FIGS. 9 A and B. Over the 96.3 hour hold, the pH and conductivity remain within acceptable limits.

PASS DS Intermediate Pool Starting Material: No conditioning is required prior to transferring the PASS DS intermediate pool into the UF/DF retentate tank because the PASS DS intermediate pool is already within the acceptable pH range. In addition, since the starting material is 50 mg/mL PASS formulated Enbrel DS, the pool does not need to be concentrated to 50 g/L because it is already at the correct concentration to perform diafiltration.

One example performed during development of the SAS final UF/DF unit operation step, to evaluate starting material source, is listed in Table 20. This example utilized DS PASS intermediate pool as the starting material and was analyzed for pH, conductivity, osmolality, protein concentration, and product quality.

TABLE 20

PASS DS Intermediate Pool Starting Material: Load, Exchange Solution, and final UF/DF pool pH

| Run Number | Target Load pH | Targer SAS Solution pH | UF/DF Pool pH |
|---|---|---|---|
| 1 | 6.3 | 6.3 | 6.23 |

Results: The product quality results for the final SAS UF/DF pool, generated using PASS DS intermediate pool as the starting material, are shown in Table 21. The step yield for Run 1 was outside of the acceptance criteria; however, it was most likely an artifact of bench-scale processing and considered not significant to the conclusions of the study. The final SAS UF/DF pool also met acceptance criteria for product quality using SEC and HIC analysis, as described above.

TABLE 21

PASS DS Intermediate Pool Starting Material: Final SAS UF/DF Pool Product Quality

| Parameter | Acceptance Criteria | Final SAS UF/DF Pool Run 1 |
|---|---|---|
| pH | 6.1-6.5 | 6.23 |
| Protein Concentration (mg/mL) | 49-51 | 49.60 |
| Step Yield (%) | 95-103 | 105.7 |

PASS DS Intermediate Pool Stability

The PASS pool does not require conditioning prior to UF/DF processing with SAS solution because this intermediate pool is already at the target pH (6.3). A pool hold study was not performed for this intermediate pool because the conditions of the pool were unchanged from Enbrel PASS DS. The pool can be held for up to 96 hours at 25° C.

UF/DF Pool Stability

The final UF/DF SAS pool, generated using PASS DS intermediate pool as the starting material, can be held for up to 96.3 hours at CRT. The pH and conductivity during the hold are shown in FIGS. 9 A and B. Over the 96.3 hour hold, the pH and conductivity remain within acceptable limits.

SAS Formulation Solution Stability

The SAS formulation solution can be held for up to 28 days at CRT. The pH and conductivity are shown in FIGS. 10 A and B. Over the 42 day hold in small scale stainless steel stability chambers with very small headspace, the SAS formulation solution is demonstrated to maintain a pH within 5.6 to 6.5. There was precipitation observed at the 35 day and 42 day time points. The 21 day time point measurement of 5.09 appears to be an outlier due to the fact that the subsequent time points are within the proposed acceptance criteria.

Conclusions: The final UF/DF unit operation can produce 50 g/L SAS formulation product and achieve consistent product quality compared to the current commercial PASS formulation product under the following process recommendations: 1) utilizing either AEX intermediate pool, or PASS DS intermediate pool, as the starting material 2) the SAS solution can be held for at least 28 days at CRT and maintain a pH of 5.6 to 6.5, 3) the conditioned AEX intermediate pool can be held at CRT for at least 52.6 hours and maintain a pH of 6.3±0.1, and 4) the SAS formulated UF/DF pool can be held at CRT for at least 96.3 hours and maintain a pH of 6.1 to 6.5 and a conductivity of 10 to 14 mS/cm.

Example 7: Isotonic Alternative Formulations

The goal of this example was to determine the effect on aggregation of increased levels of arginine, sucrose or sodium chloride on etanercept stability at 75 mg/mL at 40° C. The levels of these excipients were each increased to maintain an isotonic formulation without added phosphate buffer. Additionally, histidine was evaluated as a buffer to replace phosphate. The formulations tested are summarized in Table 22.

TABLE 22

Formulations for isotonic alternative formulations at pH 6.3 with 0.01% PS20

| Formulation Name | Buffer | L-Arginine (mM) | NaCl (mM) | Sucrose (% w/w) |
|---|---|---|---|---|
| PASST | 25 mM phosphate | 25 | 100 | 1% |
| SAST_100NaCl | none | 25 | 100 | 1% |
| SAST_30Arg | none | 30 | 100 | 1% |
| SAST_35Arg | none | 35 | 100 | 1% |
| SAST_40Arg | none | 40 | 100 | 1% |
| SAST_2Suc | none | 25 | 100 | 2% |
| SAST_120NaCl | none | 25 | 120 | 1% |
| HASST | 10 mM histidine | 25 | 100 | 1% |

Materials: Enbrel drug substance in PASS (25 mM phosphate buffer, 25 mM L-arginine, 100 mM NaCl, 1% sucrose) at 50 mg/mL was used for this study. The material was dialyzed into the new formulations (without polysorbate) and concentrated to using 75 mg/mL using 30,000 MWCO centripreps. A 1% stock solution of polysorbate 20 was prepared fresh and spiked into all formulation to a final concentration of 0.01%. All formulations were manually filled into 1 mL long BD glass syringes to a volume of 1.0 mL and then stoppered using an ASPU vacuuming stoppering unit.

Methods: The pH was measured using a Mettler Toledo pH meter combined with a Mettler MicroProbe. Samples were warmed to room temperature prior to measurements. Osmolality was measured using The Advanced Osmometer Model 3900. Each measurement was performed using 250 µL of sample and 290 osmolality standards were tested to ensure the system was operating properly. Size exclusion HPLC was run on an Agilent 1100 HPLC with Chromeleon 7.2 software.

Results: The concentration, pH and osmolality are shown in Table 23. Aggregation rates at 75 mg/mL at 40° C. were similar to the commercial formulation composition for all phosphate-free formulations with increased levels of L-arginine, sucrose and NaCl, as shown in Table 24. Additionally, use of histidine instead of phosphate as a buffer led to increased aggregation rates at 40° C.

TABLE 23

Concentration, pH and osmolality for isotonic alternative formulations

| Sample | Conc (mg/mL) | pH | osmolality |
|---|---|---|---|
| PASST | 76.3 | 6.27 | 308 |
| SAST_100NaCl | 76.8 | 6.30 | 266 |
| SAST_30Arg | 74.9 | 6.28 | 271 |
| SAST_35Arg | 76.9 | 6.27 | 280 |
| SAST_40Arg | 76.5 | 6.26 | 288 |
| SAST_2Suc | 75.2 | 6.26 | 291 |
| SAST_120NaCl | 77.1 | 6.24 | 301 |
| HASST | 76.3 | 6.36 | 272 |

TABLE 24

SEC aggregate/HMW levels, % of total, 40° C.

| Sample | 0 Week | 1 Week | 2 Week | 4 Week | 8 Week | 12 Week |
|---|---|---|---|---|---|---|
| PASST | 2.3 | 5.3 | 6.6 | 12.0 | 16.1 | 26.1 |
| SAST_100NaCl | 2.3 | 5.0 | 6.4 | 11.0 | 15.3 | 24.1 |
| SAST_30Arg | 2.4 | 5.1 | 6.6 | 11.3 | 15.9 | 24.8 |
| SAST_35Arg | 2.4 | 5.2 | 6.8 | 11.5 | 16.7 | 25.3 |
| SAST_40Arg | 2.4 | 5.1 | 6.7 | 11.0 | 16.1 | 23.7 |
| SAST_2Suc | 2.4 | 4.9 | 6.6 | 10.7 | 16.2 | 23.4 |
| SAST_120NaCl | 2.4 | 5.0 | 5.9 | 11.0 | 16.7 | 23.7 |
| HASST | 2.3 | 6.2 | 9.1 | 14.8 | 22.9 | 32.3 |

Example 8: Stability of Formulations with Various Levels of Polysorbate 20

A long-term study was performed to monitor etanercept stability at 0, 0.005, 0.01 and 0.015% polysorbate 20 in the SAS formulation at 50 mg/mL etanercept. In addition, a high concentration formulation of SAST at 100 mg/mL etanercept was tested. The stability was assessed on 1 mL fills in 1 mL staked glass needle syringes using SE-HPLC, dSEC HPLC, and particulate matter (HIAC) after storage at 4° C., 25° C. and 40° C. Osmolality, pH and protein concentration were tested at time zero only. The results of the study showed that the 50 mg/mL formulations tested remained similar to the current commercial formulation after 24 weeks at recommended storage of 2-8° C., as well as at accelerated temperatures of 25° C. and 40° C. The 100 mg/mL SAST formulation performed comparably to the 50 mg/mL formulations in terms of pH and subvisible particles; differences in aggregate levels by SEC were attributed to protein concentration.

TABLE 25

Formulation conditions at 50 mg/mL etanercept

| Formulation Name | Buffer | Other Excipients | Poly-sorbate | Protein Conc (mg/mL) |
|---|---|---|---|---|
| PASS | 25 mM phosphate | 25 mM L-arginine, 100 mM NaCl, 1% sucrose | 0 | 50 |
| SAS000T | None | 25 mM L-arginine, 120 mM NaCl, 1% sucrose | 0 | 50 |
| SAS005T | None | 25 mM L-arginine, 120 mM NaCl, 1% sucrose | 0.005 | 50 |

TABLE 25-continued

Formulation conditions at 50 mg/mL etanercept

| Formulation Name | Buffer | Other Excipients | Poly-sorbate | Protein Conc (mg/mL) |
|---|---|---|---|---|
| SAS010T | None | 25 mM L-arginine, 120 mM NaCl, 1% sucrose | 0.01 | 50 |
| SAS015T | None | 25 mM L-arginine, 120 mM NaCl, 1% sucrose | 0.015 | 50 |
| 100_SAS010T | None | 25 mM L-arginine, 120 mM NaCl, 1% sucrose | 0.010 | 100 |

Materials. Enbrel drug substance in TMS (10 mM tris buffer, 4% mannitol, 1% sucrose) at 25 mg/mL was used for this study. The bulk used for the SAS formulation was titrated to pH 6.3. The material was ultrafiltered to ~50 mg/mL etanercept, then diafiltered into PASS (25 mM phosphate, 25 mM L-arginine, 120 mM NaCl, 1% sucrose) or SAS (25 mM L-arginine, 120 mM NaCl, 1% sucrose) at 50 mg/mL etanercept. The material for the high concentration arm was then ultrafiltered to 100 mg/mL etanercept. A 1% stock solution of polysorbate 20 was prepared fresh and spiked into the formulations to the final concentrations as listed in Table 25. All formulations were manually filled into 1 mL long BD glass syringes to a volume of 1 mL and then stoppered using an ASPU vacuuming stoppering unit.

Results and Discussion: The pH of all formulations was measured at time zero and after twelve weeks at 40° C. and 24 weeks at 4° C. and 25° C. No trends were observed as a function of time or storage temperature. The measured pH values for all samples can be found in Table 26. No drift in pH was observed after twelve weeks of storage at 40° C. or 24 weeks at 4° C. and 25° C. and all samples met the acceptance criteria of +/−0.2 pH units from the target pH of 6.3. The protein concentration and osmolality of all formulations was tested at time zero. The protein concentration and osmolality results for all samples can be found in Table 26.

TABLE 26

Concentration, osmolality and pH

| Sample | Conc (mg/mL) | Osmolality (mOsm) | pH t = 0 | pH 24 wk 4° C. | pH 24 wk 25° C. | pH 12 wk 40° C. |
|---|---|---|---|---|---|---|
| PASS | 51.6 | 318 | 6.32 | 6.34 | 6.34 | 6.33 |
| SAS000T | 52.1 | 306 | 6.33 | 6.31 | 6.33 | 6.37 |
| SAS005T | 51.2 | 304 | 6.33 | 6.30 | 6.30 | 6.32 |
| SAS010T | 51.5 | 304 | 6.34 | 6.30 | 6.30 | 6.36 |
| SAS015T | 51.5 | 301 | 6.30 | 6.30 | 6.30 | 6.35 |
| 100_SAS010T | 102.8 | 304 | 6.32 | 6.28 | 6.29 | 6.36 |

SE-HPLC was performed to monitor aggregation levels as a function of formulation condition, time and temperature. Peak B is the amount of high molecular weight species (aggregate) that forms. Results showed no differences in Peak B between the PASS control and the bufferless formulations at all temperatures at their respective protein concentrations (Table 27-29). Peak B represents the total aggregate detected by SE-HPLC for these formulations. All 50 mg/ml samples remained acceptable (Peak B≤6%) after 24 weeks of storage at 4° C. and 25° C. and after 2 weeks of storage at 40° C.

Sub-visible particles were monitored by light obscuration particle counting (HIAC). Results were in line i6th historical PFS data and were similar between the formulations across all temperatures after 24 weeks (Table 30).

TABLE 27

SEC analysis of Peak B, % of total, 4° C.

| sample | t = 0 wk | t = 4 wk | t = 8 wk | t = 12 wk | t = 24 wk |
|---|---|---|---|---|---|
| PASS | 1.7 | 1.7 | 1.7 | 1.7 | 1.8 |
| SAS000T | 1.7 | 1.8 | 1.8 | 1.8 | 1.9 |
| SAS005T | 1.7 | 1.8 | 1.8 | 1.8 | 1.9 |
| SAS010T | 1.7 | 1.8 | 1.8 | 1.9 | 1.9 |
| SAS015T | 1.7 | 1.8 | 1.8 | 1.8 | 1.9 |
| 100_SAS010T | 1.9 | 2.0 | 2.1 | 2.2 | 2.4 |

TABLE 28

SEC analysis of Peak B, % of total, 25° C.

| sample | t = 0 wk | t = 2 wk | t = 4 wk | t = 8 wk | t = 12 wk | t = 24 wk |
|---|---|---|---|---|---|---|
| PASS | 1.7 | 2.1 | 2.4 | 2.9 | 3.5 | 4.8 |
| SAS000T | 1.7 | 2.1 | 2.5 | 2.9 | 3.5 | 5.0 |
| SAS005T | 1.7 | 2.2 | 2.5 | 2.9 | 3.5 | 4.9 |
| SAS010T | 1.7 | 2.1 | 2.5 | 3.0 | 3.6 | 4.8 |
| SAS015T | 1.7 | 2.2 | 2.4 | 3.0 | 3.5 | 4.8 |
| 100_SAS010T | 1.9 | 2.8 | 3.4 | 4.4 | 5.4 | 7.6 |

TABLE 29

SEC analysis of Peak B, % of total, 40° C.

| sample | t = 0 wk | t = 2 wk | t = 4 wk | t = 8 wk | t = 12 wk |
|---|---|---|---|---|---|
| PASS | 1.7 | 5.7 | 10.4 | 17.4 | 20.6 |
| SAS000T | 1.7 | 4.9 | 8.9 | 15.4 | 19.2 |
| SAS005T | 1.7 | 5.2 | 9.1 | 15.9 | 19.4 |
| SAS010T | 1.7 | 5.2 | 9.3 | 15.8 | 19.2 |
| SAS015T | 1.7 | 5.4 | 9.4 | 15.9 | 19.0 |
| 100_SAS010T | 1.9 | 9.0 | 15.6 | 24.5 | 27.1 |

TABLE 30

Particles/mL (light obscuration), 4° C.

| | 2 µm | | 10 µm | | 25 µm | |
|---|---|---|---|---|---|---|
| | t = 0 wk | t = 24 wk | t = 0 wk | t = 24 wk | t = 0 wk | t = 24 wk |
| PASS | 19197 | 3422 | 1785 | 670 | 25 | 67 |
| SAS000T | 13004 | 4489 | 1265 | 762 | 60 | 104 |
| SAS005T | 12344 | 1292 | 502 | 59 | 7 | 4 |
| SAS010T | 11964 | 2254 | 1058 | 167 | 9 | 2 |
| SAS015T | 11388 | 7283 | 934 | 591 | 2 | 4 |
| 100_SAS010T | 58087 | 8931 | 559 | 816 | 3 | 0 |

Conclusions: The long-term stability of a reformulation candidate at 50 mg/mL etanercept with levels of polysorbate from 0 to 0.015% and the current commercial formulation was assessed at 4° C., 25° C. and 40° C.; a high concentration arm at 100 mg/mL etanercept was also tested for the SAS010T formulations. No significant differences were observed between the formulations at their respective protein concentrations after 24 weeks by SE-, dSEC, or HIC HPLC assays as well as by light obscuration. No drift in pH was observed and all formulations remained within acceptable ranges. The results of the study showed that the SAST_120NaCl formulations at 50 mg/mL were stable and similar to the current commercial formulation after 24 weeks at the recommended storage temperature of 2° C. to 8° C.

Example 9: Stability of Formulations in Plastic Syringes

A long-term study was performed to monitor etanercept stability in the PASS and SAS formulations at 50 mg/mL etanercept in COP plastic silicone oil free pre-filled syringe systems compared to glass siliconized pre-filled syringes. The stability was assessed on 1 mL fills in the various syringe systems using SE-HPLC, pH and particulate matter (HIAC) after storage at 4° C., 25° C. and 40° C. Protein concentration was tested at time zero only.

Materials. Etanercept drug substance in TMS (10 mM tris buffer, 4% mannitol, 1% sucrose) at 25 mg/mL etanercept was used for this study. The bulk used for the SAS formulation was titrated to pH 6.3. The material was ultrafiltered to ~50 mg/mL etanercept, then diafiltered into PASS (25 mM phosphate, 25 mM L-arginine, 120 mM NaCl, 1% sucrose) or SAS (25 mM L-arginine, 120 mM NaCl, 1% sucrose) at 50 mg/mL etanercept. All formulations were manually filled into 1 mL long glass syringes or 1 mL COP plastic silicone oil free syringes (COP_A and COP_B) to a volume of 1 mL and then stoppered using a vacuuming stoppering unit.

Methods: The pH was measured using a Mettler Toledo SevenEasy pH meter combined with a Mettler Inlab Micro-Probe. Samples were warmed to room temperature prior to measurements. Protein concentration measurements using absorbance at 280 nM for all samples were performed at room temperature using the Nano Drop system. Size exclusion HPLC was run on an Agilent 1100 HPLC with Chromeleon 7.2 software. Sub-visible particle analysis was performed using a HACH HIAC/Royco particle counter system equipped with an HRLD-150 laser and Pharm Spec software. All samples were diluted with PASS formulation buffer to 25 mg/mL. Samples were thoroughly mixed, uncapped and degassed for 2 hours at 75 torr prior to analysis. Four (4) sips of 1.0 mL each (no tare volume) were performed, with the first sip discarded and the remaining 3 sips averaged. Data for particle sizes 2, 5, 10, and 25 μm was collected at all timepoints. The results account for the dilution and are reported as cumulative counts per mL.

Results & Discussion: Stability in the plastic silicone oil free syringes is similar to stability in glass siliconized syringes. The protein concentration of all formulations was tested at time zero. The pH of all formulations was measured at time zero and after twelve weeks at 40° C. and 24 weeks at 4° C. and 25° C. No trends were observed as a function of time or storage temperature and all samples met the pH acceptance criteria of +/−0.2 pH units from the target pH of 6.3. The protein concentration and measured pH values for all samples can be found in Table 31.

TABLE 31

Protein concentration and pH results

| Sample | Conc (mg/mL) | pH t = 0 | pH 24 wk 4° C. | pH 24 wk 25° C. | pH 12 wk 40° C. |
|---|---|---|---|---|---|
| PASS_Glass | 50.9 | 6.3 | 6.4 | 6.4 | 6.4 |
| SAS_Glass | 52.3 | 6.3 | 6.4 | 6.4 | 6.3 |
| PASS_COP_A | 51.1 | 6.3 | 6.4 | 6.4 | 6.3 |
| SAS_COP_A | 51.9 | 6.3 | 6.4 | 6.4 | 6.3 |

TABLE 31-continued

Protein concentration and pH results

| Sample | Conc (mg/mL) | pH t = 0 | pH 24 wk 4° C. | pH 24 wk 25° C. | pH 12 wk 40° C. |
|---|---|---|---|---|---|
| PASS_COP_B | 51.1 | 6.4 | 6.4 | 6.4 | 6.3 |
| SAS_COP_B | 52.2 | 6.3 | 6.4 | 6.4 | 6.3 |

SE-HPLC was performed to monitor aggregation levels as a function of formulation condition, time and temperature. Peak B is the amount of high molecular weight species (aggregate) that forms. Results showed no differences in Peak B between the glass syringes and the COP plastic silicone oil free syringes (Table 32-34). Peak B represents the total aggregate detected by SE-HPLC for these formulations. All samples remained acceptable (Peak B≤6%) after 24 weeks of storage at 4° C. and 25° C.

TABLE 32

SEC analysis of Peak B, % of total, 4° C.

| sample | t = 0 wk | t = 4 wk | t = 8 wk | t = 12 wk | t = 24 wk |
|---|---|---|---|---|---|
| PASS_Glass | 2.9 | 3.0 | 3.1 | 3.1 | 3.1 |
| SAS_Glass | 3.0 | 3.1 | 3.2 | 3.2 | 3.1 |
| PASS_COP_A | 2.9 | 3.0 | 3.1 | 3.1 | 3.1 |
| SAS_COP_A | 3.0 | 3.1 | 3.2 | 3.2 | 3.2 |
| PASS_COP_B | 3.0 | 3.1 | 3.2 | 3.2 | 3.3 |
| SAS_COP_B | 3.0 | 3.1 | 3.2 | 3.2 | 3.2 |

TABLE 33

SEC analysis of Peak B, % of total, 25° C.

| sample | t = 0 wk | t = 2 wk | t = 4 wk | t = 8 wk | t = 12 wk | t = 24 wk |
|---|---|---|---|---|---|---|
| PASS_Glass | 2.9 | 3.0 | 3.4 | 3.9 | 4.4 | 5.5 |
| SAS_Glass | 3.0 | 3.1 | 3.6 | 4.1 | 4.5 | 5.6 |
| PASS_COP_A | 2.9 | 3.1 | 3.4 | 3.9 | 4.4 | 5.4 |
| SAS_COP_A | 3.0 | 3.2 | 3.5 | 4.1 | 4.6 | 5.8 |
| PASS_COP_B | 3.0 | 3.2 | 3.6 | 4.1 | 4.6 | 5.5 |
| SAS_COP_B | 3.0 | 3.1 | 3.5 | 4.0 | 4.5 | 5.7 |

TABLE 34

SEC analysis of Peak B, % of total, 40° C.

| sample | t = 0 wk | t = 2 wk | t = 4 wk | t = 8 wk | t = 12 wk |
|---|---|---|---|---|---|
| PASS_Glass | 2.9 | 6.4 | 11.1 | 17.2 | 23.0 |
| SAS_Glass | 3.0 | 6.1 | 9.8 | 15.4 | 21.0 |
| PASS_COP_A | 2.9 | 6.5 | 9.9 | 16.2 | 21.4 |
| SAS_COP_A | 3.0 | 6.3 | 9.9 | 14.9 | 18.6 |
| PASS_COP_B | 3.0 | 6.4 | 10.7 | 17.8 | 19.6 |
| SAS_COP_B | 3.0 | 6.2 | 10.0 | 17.1 | 22.4 |

Sub-visible particles were monitored by light obscuration particle counting (HIAC). Results for formulations filled in BD glass syringes were in line with historical PFS data while subvisible particles are reduced in the silicone-oil free plastic syringes (Table 35).

TABLE 35

| | Particles/mL (light obscuration), 4° C. | | | | | |
|---|---|---|---|---|---|---|
| | 2 μm | | 10 μm | | 25 μm | |
| | t = 0 wk | t = 24 wk | t = 0 wk | t = 24 wk | t = 0 wk | t = 24 wk |
| PASS_Glass | 10090 | 15994 | 468 | 726 | 14 | 2 |
| SAS_Glass | 12240 | 13340 | 1183 | 505 | 18 | 5 |
| PASS_COP_A | 93 | 130 | 2 | 6 | 0 | 0 |
| SAS_COP_A | 30 | 74 | 2 | 2 | 0 | 0 |
| PASS_COP_B | 81 | 204 | 3 | 4 | 0 | 2 |
| SAS_COP_B | 62 | 237 | 2 | 8 | 0 | 1 |

Conclusions: The long-term stability of the SAS formulation at 50 mg/mL etanercept and the current commercial etanercept formulation stored in glass siliconized syringes and COP silicone oil free syringes was assessed at 4° C., 25° C. and 40° C. No significant differences were observed between the formulations as a function of syringe type after 24 weeks by SE-HPLC. No drift in pH was observed and all formulations remained within acceptable ranges. Sub-visible particles were reduced in the COP silicone oil free plastic syringes and were consistent with historical PFS results w % ben stored in the glass syringes. The results of the study showed that the SAS formulation at 50 mg/mL etanercept was stable and similar to the current commercial formulation after 24 weeks at the recommended storage temperature of 2° C. to 8° C. in various syringe types.

What is claimed is:

1. A method of treating a patient having rheumatoid arthritis, psoriatic arthritis, ankylosing spondylitis, or psoriasis, comprising administering to said patient a pharmaceutical composition comprising between 75 mM and 150 mM NaCl, between 5 mM and 100 mM arginine, between 0.5% and 2% (w/v) sucrose, and between 40 mg/mL and 100 mg/mL etanercept, wherein the pharmaceutical composition comprises less than 2.0 mM total additional buffering agent, and the pH of the pharmaceutical composition is between 6.1 and 6.5.

2. The method of claim 1, wherein the pharmaceutical composition is administered parenterally.

3. The method of claim 1, wherein the pharmaceutical composition is administered subcutaneously, intramuscularly, intravenously, intraperitoneally, intracerebrospinally, intra-articularly, intrasynovially, or intrathecally.

4. The method of claim 1, wherein the pharmaceutical composition is administered as a bolus injection or continuous infusion.

5. The method of claim 1, comprising administering the pharmaceutical composition with a dispenser device comprising about a single dose of the pharmaceutical composition.

6. The method of claim 5, wherein the dispenser device comprises a syringe.

7. The method of claim 1, wherein the pharmaceutical composition is administered by implantation, or by intramuscular injection.

8. The method of claim 1, wherein the pharmaceutical composition comprises less than 1.5 mM total additional buffering agent.

9. The method of claim 8, wherein the pharmaceutical composition comprises less than 1.0 mM total additional buffering agent.

10. The method of claim 8, wherein the pharmaceutical composition comprises less than 0.5 mM total additional buffering agent.

11. The method of claim 8, wherein the pharmaceutical composition comprises less than 0.25 mM total additional buffering agent.

12. The method of claim 11, wherein the arginine is L-arginine.

13. The method of claim 12, wherein the pharmaceutical composition comprises about 50 mg/mL etanercept, about 120 mM NaCl, about 25 mM L-arginine hydrochloride, and about 1% (w/v) sucrose.

14. The method of claim 13, wherein the pharmaceutical composition maintains stability of the etanercept such that less than 28% of the total amount of etanercept is in a misfolded form as assessed using hydrophobic interaction chromatography after two weeks' storage at approximately 25° C.

15. The method of claim 13, wherein the etanercept consists of a dimer of the amino acid sequence of SEQ ID NO: 1.

16. The method of claim 8, wherein the pharmaceutical composition comprises 0.1 mM or less total additional buffering agent.

17. The method of claim 16, wherein the arginine is L-arginine.

18. The method of claim 17, wherein the etanercept consists of a dimer of the amino acid sequence of SEQ ID NO: 1.

19. The method of claim 17, wherein the pharmaceutical composition comprises about 50 mg/mL etanercept, about 120 mM NaCl, about 25 mM L-arginine hydrochloride, and about 1% (w/v) sucrose.

20. The method of claim 19, wherein the etanercept consists of a dimer of the amino acid sequence of SEQ ID NO: 1.

21. The method of claim 19, wherein said pharmaceutical composition maintains a pH of between about 6.1 and about 6.5 for at least two weeks during storage at approximately 25° C.

22. The method of claim 21, wherein the etanercept consists of a dimer of the amino acid sequence of SEQ ID NO: 1.

23. The method of claim 1, wherein the arginine is L-arginine.

24. The method of claim 23, wherein the L-arginine is L-arginine hydrochloride.

25. The method of claim 23, wherein the L-arginine is L-arginine base.

26. The method of claim 1, wherein the pharmaceutical composition maintains a pH between 6.1 and 6.5 when stored at controlled room temperature (CRT) for 2 weeks.

27. The method of claim 26, wherein the pharmaceutical composition maintains a pH between about 6.2 and about 6.3 when stored at controlled room temperature (CRT) for 2 weeks.

28. The method of claim 1, wherein the pharmaceutical composition maintains a pH of between 5.8 and 6.7 for at least two weeks when stored at approximately 25° C., and wherein less than 6% of the total etanercept is aggregated in a high molecular weight form as assessed using size exclusion chromatography after two weeks' storage at approximately 25° C.

29. The method of claim 1, wherein said pharmaceutical composition maintains a pH of between about 6.1 and about 6.5 for at least two weeks during storage at approximately 25° C.

30. The method of claim 1, wherein said pharmaceutical composition maintains a pH of between about 6.2 and about 6.4 for at least two weeks during storage at approximately 25° C.

31. The method of claim 1, wherein less than 28% of the total amount of etanercept is in a misfolded form as assessed using hydrophobic interaction chromatography after two weeks' storage at approximately 25° C.

32. The method of claim 1, wherein the pharmaceutical composition has an osmolality of about 180 to about 420 milliosmolals.

33. The method of claim 32, wherein the pharmaceutical composition has an osmolality of about 250 to about 350 milliosmolals.

34. The method of claim 33, wherein the pharmaceutical composition has an osmolality of about 290 to about 310 milliosmolals.

35. The method of claim 34, wherein the pharmaceutical composition has an osmolality of about 300 to about 310 milliosmolals.

36. The method of claim 1, wherein the pharmaceutical composition consists essentially of about 50 mg/mL etanercept, about 120 mM NaCl, about 25 mM L-arginine hydrochloride, about 1% (w/v) sucrose and water.

37. The method of claim 36, wherein said pharmaceutical composition maintains a pH of between about 6.1 and about 6.5 for at least two weeks during storage at approximately 25° C.

38. The method of claim 36, wherein the pharmaceutical composition maintains stability of the etanercept such that less than 28% of the total amount of etanercept is in a misfolded form as assessed using hydrophobic interaction chromatography after two weeks' storage at approximately 25° C.

39. The method of claim 36, wherein the etanercept consists of a dimer of the amino acid sequence of SEQ ID NO: 1.

40. The method of claim 1, wherein the pharmaceutical composition consists of about 50 mg/mL etanercept, about 120 mM NaCl, about 25 mM L-arginine hydrochloride, about 1% (w/v) sucrose, and water.

41. The method of claim 40, wherein said pharmaceutical composition maintains a pH of between about 6.1 and about 6.5 for at least two weeks during storage at approximately 25° C.

42. The method of claim 40, wherein the pharmaceutical composition maintains stability of the etanercept such that less than 28% of the total amount of etanercept is in a misfolded form as assessed using hydrophobic interaction chromatography after two weeks' storage at approximately 25° C.

43. The method of claim 40, wherein the etanercept consists of a dimer of the amino acid sequence of SEQ ID NO: 1.

44. The method of claim 1, wherein the pharmaceutical composition further comprises polysorbate 20.

45. The method of claim 44, wherein the polysorbate 20 concentration (w/v) is between about 0.001% and about 0.1%.

46. The method of claim 45, wherein the polysorbate 20 concentration (w/v) is about 0.005%, about 0.01%, or about 0.015%.

47. The method of claim 1, wherein the etanercept consists of a dimer of the amino acid sequence of SEQ ID NO: 1.

48. The method of claim 1, wherein said pharmaceutical composition maintains a pH of between about 6.1 and about 6.5 for at least two weeks during storage at approximately 25° C., and wherein the pharmaceutical composition maintains stability of the etanercept such that less than 28% of the total amount of etanercept is in a misfolded form as assessed using hydrophobic interaction chromatography after two weeks' storage at approximately 25° C.

* * * * *

UNITED STATES PATENT AND TRADEMARK OFFICE
CERTIFICATE OF CORRECTION

Page 1 of 3

PATENT NO. : 12,214,013 B2
APPLICATION NO. : 17/933055
DATED : February 4, 2025
INVENTOR(S) : Monica Goss et al.

It is certified that error appears in the above-identified patent and that said Letters Patent is hereby corrected as shown below:

On the Title Page

Page 3, Column 2 (Other Publications), Line 40, delete "Treated", Physcians' Desk" and insert --Treated", Physicians' Desk--.

Page 3, Column 2 (Other Publications), Line 57, delete "AbbVie Biotechology Ltd.," and insert --AbbVie Biotechnology Ltd.,--.

Page 4, Column 1 (Other Publications), Line 63, delete "AvvVie" and insert --AbbVie--.

Page 6, Column 2 (Other Publications), Line 4, delete "targeted Immuconjugate of Calichemicin for" and insert --targeted immunoconjugate of calicheamicin for--.

Page 6, Column 2 (Other Publications), Line 15, delete "EMBERL (etamercept)" and insert --ENBREL (etanercept)--.

Page 6, Column 2 (Other Publications), Line 16, delete "EMBERL (etamercept)" and insert --ENBREL (etanercept)--.

Page 7, Column 2 (Other Publications), Line 46, delete "Gokarn Oppostion to" and insert --Gokarn Opposition to--.

Page 8, Column 1 (Other Publications), Line 31, delete "Factor Receptorexpressing Tumours" and insert --Factor Receptor expressing Tumours--.

Page 8, Column 2 (Other Publications), Line 5, delete "to Diptheria, Tetanus," and insert --to Diphtheria, Tetanus,--.

Page 9, Column 2 (Other Publications), Line 30, delete "Etannercept Therapy" and insert --Etanercept Therapy--.

Signed and Sealed this
Third Day of June, 2025

Coke Morgan Stewart
*Acting Director of the United States Patent and Trademark Office*

CERTIFICATE OF CORRECTION (continued)
U.S. Pat. No. 12,214,013 B2

Page 11, Column 1 (Other Publications), Line 65, delete "Antibody, Pharmacuetial Research," and insert --Antibody, Pharmaceutical Research,--.

Page 12, Column 1 (Other Publications), Line 50, delete "Pulmozyne® (dronase alfa)," and insert --Pulmozyme® (dornase alfa),--.

Page 12, Column 2 (Other Publications), Line 7, delete "Remicade® (iflizimab)" and insert --Remicade® (infliximab)--.

Page 12, Column 2 (Other Publications), Line 8, delete "Remicade® (iflizimab)" and insert --Remicade® (infliximab)--.

Page 12, Column 2 (Other Publications), Line 13, delete "Inyrtlrukin-1" and insert --Interleukin-1--.

Page 13, Column 2 (Other Publications), Line 52, delete "concentration soultions." and insert --concentration solutions.--.

Page 14, Column 1 (Other Publications), Line 46, delete "Human Prethombin-2 and" and insert --Human Prothrombin-2 and--.

Page 15, Column 1 (Other Publications), Line 27, delete "by lonic Strength" and insert --by Ionic Strength--.

Page 15, Column 2 (Other Publications), Line 25, delete "Artificial Organd 21(6)," and insert --Artificial Organs 21(6),--.

In the Specification

Column 2, Line 5, delete "Tris HCL, 4%" and insert --Tris HCI, 4%--.

Column 5, Line 47 (approx.), delete "Pro-G!u-" and insert --Pro-Glu- --.

Column 13, Line 25, delete "of poly sorbate 20" and insert --of polysorbate 20--.

Column 13, Line 37, delete "Agilent 1100)" and insert --Agilent 1100--.

Column 14, Line 33 (approx.) (TABLE 4), delete "3,2" and insert --3.2--.

Column 14, Line 37 (approx.) (TABLE 4), delete "3 9" and insert --3.9--.

Column 17, Line 28 (approx.) (TABLE 10), delete "28,.7" and insert --28.7--.

Column 17, Line 29 (approx.) (TABLE 10), delete "23 5" and insert --23.5--.

Column 19, Line 52, delete "(Peak B≤56%) after" and insert --(Peak B≤6%) after--.

Column 26, Line 28 (approx.) (TABLE 24), delete "5.9" and insert --6.9--.

Column 27, Line 16 (approx.), delete "Materials. Enbrel" and insert --Materials: Enbrel--.

Column 27, Line 65, delete "mg/ml samples" and insert --mg/mL samples--.

Column 28, Line 2, delete "line i6th historical" and insert --line with historical--.

Column 29, Line 16, delete "Materials. Etanercept" and insert --Materials: Etanercept--.

Column 32, Line 11 (approx.), delete "results w % ben stored" and insert --results when stored--.

SEQUENCE LISTING

```
Sequence total quantity: 1
SEQ ID NO: 1              moltype = AA  length = 467
FEATURE                   Location/Qualifiers
REGION                    1..467
                          note = Fusion
source                    1..467
                          mol_type = protein
                          organism = synthetic construct
SEQUENCE: 1
LPAQVAFTPY APEPGSTCRL REYYDQTAQM CCSKCSPGQH AKVFCTKTSD TVCDSCEDST    60
YTQLWNWVPE CLSCGSRCSS DQVETQACTR EQNRICTCRP GWYCALSKQE GCRLCAPLRK   120
CRPGFGVARP GTETSDVVCK PCAPGTFSNT TSSTDICRPH QICNVVAIPG NASMDAVCTS   180
TSPTRSMAPG AVHLPQPVST RSQHTQPTPE PSTAPSTSFL LPMGPSPPAE GSTGDEPKSC   240
DKTHTCPPCP APELLGGPSV FLFPPKPKDT LMISRTPEVT CVVVDVSHED PEVKFNWYVD   300
GVEVHNAKTK PREEQYNSTY RVVSVLTVLH QDWLNGKEYK CKVSNKALPA PIEKTISKAK   360
GQPREPQVYT LPPSREEMTK NQVSLTCLVK GFYPSDIAVE WESNGQPENN YKTTPPVLDS   420
DGSFFLYSKL TVDKSRWQQG NVFSCSVMHE ALHNHYTQKS LSLSPGK                 467
```